(12) United States Patent
Heo

(10) Patent No.: US 8,729,047 B2
(45) Date of Patent: May 20, 2014

(54) COMPOSITIONS FOR INHIBITING REDOX-SENSITIVE GTPASES

(75) Inventor: Jongyun Heo, Arlington, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 13/332,858

(22) Filed: Dec. 21, 2011

(65) Prior Publication Data

US 2012/0171302 A1 Jul. 5, 2012

Related U.S. Application Data

(60) Provisional application No. 61/426,643, filed on Dec. 23, 2010.

(51) Int. Cl.
*A61K 31/70* (2006.01)

(52) U.S. Cl.
USPC .......................................................... 514/45

(58) Field of Classification Search
USPC .......................................................... 514/45
See application file for complete search history.

(56) References Cited

U.S. PATENT DOCUMENTS

2004/0023994 A1 2/2004 Elfarra et al.

OTHER PUBLICATIONS

Heo et al., "Ras-Targeting Action of Thiopurines in the Presence of Reactive Nitrogen Species", Biochemistry, vol. 49, No. 18, pp. 3965-3976 (May 2010).*
Langmuir et al., Acute myeloid leukaemia in children, Best Pract. Res. Clin. Haematol., 14: 77-93 (2001).
Elion, G.B., The Purine Path to Chemotherapy, Bioscience Reports, 9: 509-529 (1989).
Gearry et al., Azathioprine and 6-mercaptopurine pharmacogenetics and metabolite monitoring in inflammatory bowel disease, J. Gastroenterol. Hepatol., 20: 1149-1157 (2005).
Tiede et al., CD28-dependent Rac1 activation is the molecular target of azathioprine in primary human CD4+T lymphocytes, J. Clin. Invest., 111: 1133-1145 (2003).
Poppe et al., Azathioprine Suppresses Ezrin-Radixin-Moesin-Dependent T Cell-APC Conjugation through Inhibition of Vav Guanosine Exchange Activity on Rac Proteins, J. Immunol., 176: 640-651 (2006).
Lage et al, Involvement of the DNA mismatch repair system in antineoplastic drug resistance, J. Cancer Res. Clin. Oncol., 125: 156-165 (1999).
Yan et al., DNA Mismatch Repair (MMR) Mediates 6-Thioguanine Genotoxicity by Introducing Single-strand Breaks to Signal a G2-M Arrest in MMR-proficient RKO Cells, Clin. Cancer Res., 9: 2327-2334 (2003).
Karran, P., Thiopurines, DNA damage, DNA repair and therapy-related cancer, Br. Med. Bull., 79-80: 153-170 (2006).
Karran et al., Thiopurines in current medical practice: molecular mechanisms and contributions to therapy-related cancer, Nat. Rev. Cancer, 8: 24-36 (2008).
Heo, J., Redox Control of GTPases: From Molecular Mechanisms to Functional Significance in Health and Disease, Antioxid. Redox Signaling, 14: 689-724 (Nov. 2011).
Stenmark et al., The Rab GTPase family, Genome Biol., 2: 3007.1-3007.7 (2001).
Jordens et al., Rab Proteins, Connecting Transport and Vesicle Fusion, Traffic, 6: 1070-1077 (2005).
Sandilands et al., Endosomal trafficking of Src tyrosine kinase, Trends Cell Biol., 18: 322-329 (2008).
Stenmark, H., Rab GTPases as coordinators of vesicle traffic, Nat. Rev. Mol. Cell Biol., 10: 513-525 (2009).
Stein et al., Rab proteins and endocytic trafficking: potential targets for therapeutic intervention, Adv. Drug Deliv. Rev., 55: 1421-1437 (2003).
Chia et al., Emerging roles for Rab family GTPases in human cancer, Biochim. Biophys. Acta 1795, 110-116 (2009).
Cuffari et al., Quantitation of 6-thioguanine in peripheral blood leukocyte DNA in Crohn's disease patients on maintenance 6-mercaptopurine therapy, Can. J. Physiol. Pharmacol, 74: 580-585 (1996).
Maltzman et al., Azathioprine: old drug, new actions, J Clin. Invest., 111: 1122-1124 (2003).
Quemeneur et al., Differential Control of Cell Cycle, Proliferation, and Survival of Primary T Lymphocytes by Purine and Pyrimidine Nucleotides, J. Immunol., 170: 4986-4995 (2003).
Heo et al., Ras-Targeting Action of Thiopurines in the Presence of Reactive Nitrogen Species, Biochemistry, 49: 3965-3976 (Apr. 2010).
Heo et al., Mechanism of Redox-mediated Guanine Nucleotide Exchange on Redox-active Rho GTPases, J. Biol. Chem., 280: 31003-31010 (2005).
Heo et al., Redox Regulation of RhoA, Biochemistry, 45: 14481-14489 (2006).
Heo et al., Mechanism of p21Ras S-Nitrosylation and Kinetics of Nitric Oxide-Mediated Guanine Nucleotide Exchange, Biochemistry, 43: 2314-2322 (2004).
Heo et al., Mechanism of Free Radical Nitric Oxide-mediated Ras Guanine Nucleotide Dissociation, J. Mol. Biol., 346: 1423-1440 (2005).
Heo et al., Superoxide Anion Radical Modulates the Activity of Ras and Ras-related GTPases by a Radical-based Mechanism Similar to That of Nitric Oxide, J. Biol. Chem., 280: 12438-12445 (2005).
Heo, J., Ras Regulation by Reactive Oxygen and Nitrogen Species, Biochemistry, 45: 2200-2210 (2006).
Heo, J., Redox regulation of Ran GTPase, Biochem. Biophys. Res. Commun., 376: 568-572 (2008).
Dias et al., X-ray Crystal Structures Reveal Two Activated States for RhoC, Biochemistry, 46: 6547-6558 (2007).
Heo et al., Insight into the 6-Thiopurine-Mediated Termination of the Invasive Motility of Tumor Cells Derived from Inflammatory Breast Cancer, Biochemistry, 50: 5731-5742 (May 2011).
Gunnarsdottir et al., Novel Glutathione-Dependent Thiopurine Prodrugs: Evidence for Enhanced Cytotoxicity in Tumor Cells and for Decreased Bone Marrow Toxicity in Mice, The Journal of Pharmacology and Experimental Therapeutics, 301: 77-86 (2002).
Napoli et al., Nitric Oxide-Releasing Drugs, Annu. Rev. Pharmacol. Toxicol., 43: 97-123 (2003).

* cited by examiner

*Primary Examiner* — Kevin E Weddington
(74) *Attorney, Agent, or Firm* — Nevrivy Patent Law Group P.L.L.C.

(57) ABSTRACT

The invention provides compositions for inhibiting a redox-sensitive GTPase protein, including a Rho or Rab family GTPase, comprising an effective amount of a redox-sensitive purine compound and an effective amount of a redox agent. The invention further provides methods of inhibiting a redox-sensitive GTPase protein, including a Rho or Rab family GTPase, by administering compositions of the invention. Methods of screening for compounds that inhibit a redox-sensitive GTPase protein, including compounds that target and inhibit Rho or Rab family GTPases, are further provided.

5 Claims, 29 Drawing Sheets

FIG. 2

| | | |
|---|---|---|
| Rac1 | -GSPQAIKCVVVGDGAVGKTCLLISYTTNAFPGEYIPTVFDNYSANVMV | 49 SEQ ID NO:5 |
| Cdc42 | ---XQTIKCVVVGDGAVGKTCLLISYTTNKFPSEYVPTVFDNYAVTVXIG | 47 SEQ ID NO:6 |
| RhoG | --MQSIKCVVVGDGAVGKTCLLICYTTNAFPKEYIPTVFDNYSAQSAV | 47 SEQ ID NO:7 |
| RhoA | SMAAIRKKLVIVGDVACGKTCLLIVFSKDQFPEVYVPTVFENYVADIEV | 50 SEQ ID NO:8 |
| RhoC | -MAAIRKKLVIVGDGACGKTCLLIVFSKDQFPEVYVPTVFENYIADIEV | 49 SEQ ID NO:9 |
| RhoB | -MAAIRKKLVVVGDGACGKTCLLIVSKERPEVYVPTVFENYVADIEV | 49 SEQ ID NO:10 |
| H-Ras | --MTEYKLVVVGAGGVGKSALTIQLIQNHFVDEYDPTIEDSYRKQVVI | 47 SEQ ID NO:11 |
| K-Ras | --MTEYKLVVVGAGGVGKSALTIQLIQNHFVDEYDPTIEDSYRKQVVI | 47 SEQ ID NO:12 |
| ruler | 1....+....10....+....20....+....30....+....40....+....50 | |

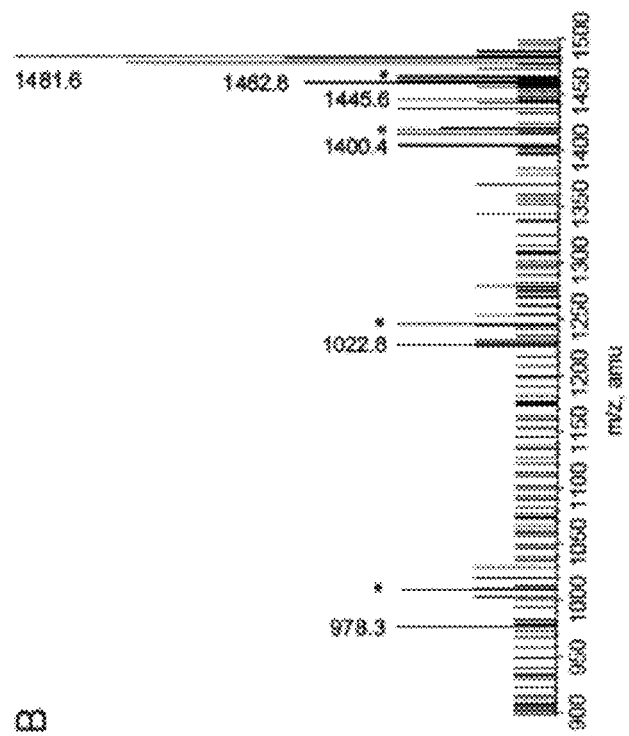
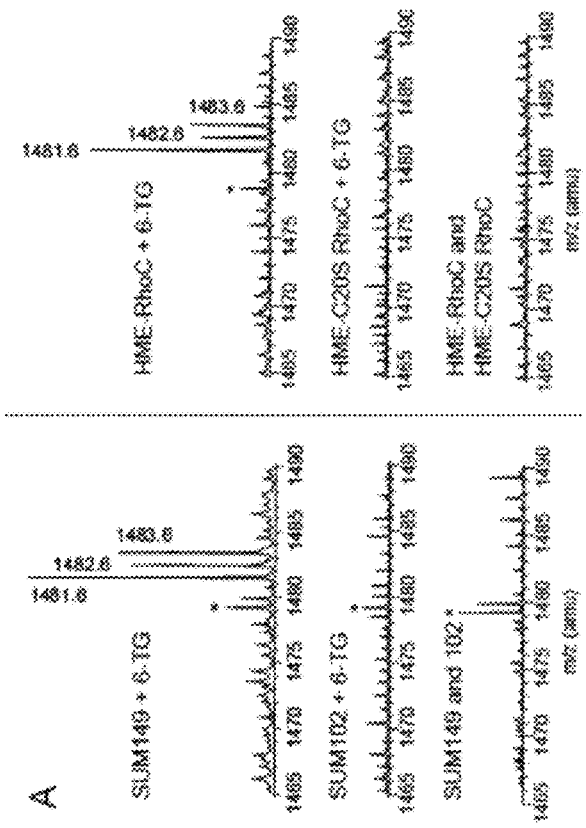
FIG. 15

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: redox sensitive motif
<220> FEATURE:
<221> NAME/KEY: Misc_Feature
<222> LOCATION: (2)..(5)
<223> OTHER INFORMATION: Xaa is an unspecified amino acid
<220> FEATURE:
<221> NAME/KEY: Misc_Feature
<222> LOCATION: (8)..(8)
<223> OTHER INFORMATION: Xaa is Serine or Threonine

<400> SEQUENCE: 1

Gly Xaa Xaa Xaa Xaa Gly Lys Xaa Cys
1               5

<210> SEQ ID NO 2
<211> LENGTH: 9
<212> TYPE: PRT
<213> ORGANISM: Artificial Sequence
<220> FEATURE:
<223> OTHER INFORMATION: redox sensitive motif
<220> FEATURE:
<221> NAME/KEY: Misc_Feature
<222> LOCATION: (2)..(4)
<223> OTHER INFORMATION: Xaa is an unspecified amino acid
<220> FEATURE:
<221> NAME/KEY: Misc_Feature
<222> LOCATION: (8)..(8)
<223> OTHER INFORMATION: Xaa is Serine or Threonine

<400> SEQUENCE: 2

Gly Xaa Xaa Xaa Cys Gly Lys Xaa Cys
1               5

<210> SEQ ID NO 3
<211> LENGTH: 4
<212> TYPE: PRT
<213> ORGANISM: Artificial Sequence
<220> FEATURE:
<223> OTHER INFORMATION: Redox sensitive motif
```

-continued

```
<400> SEQUENCE: 3

Asn Lys Cys Asp
1

<210> SEQ ID NO 4
<211> LENGTH: 9
<212> TYPE: PRT
<213> ORGANISM: Artificial Sequence
<220> FEATURE:
<223> OTHER INFORMATION: mass spectrometry fragment
<220> FEATURE:
<221> NAME/KEY: Binding
<222> LOCATION: (2)..(2)
<223> OTHER INFORMATION: Binding to 6-TGDP

<400> SEQUENCE: 4

Thr Cys Leu Leu Ile Val Phe Ser Lys
1               5

<210> SEQ ID NO 5
<211> LENGTH: 49
<212> TYPE: PRT
<213> ORGANISM: Artificial Sequence
<220> FEATURE:
<223> OTHER INFORMATION: Rac1 peptide sequence

<400> SEQUENCE: 5

Gly Ser Pro Gln Ala Ile Lys Cys Val Val Gly Asp Gly Ala Val
1               5                   10                  15

Gly Lys Thr Cys Leu Leu Ile Ser Tyr Thr Thr Asn Ala Phe Pro Gly
            20                  25                  30

Glu Tyr Ile Pro Thr Val Phe Asp Asn Tyr Ser Ala Asn Val Met Val
        35                  40                  45

Asp

<210> SEQ ID NO 6
<211> LENGTH: 47
<212> TYPE: PRT
<213> ORGANISM: Artificial sequence
<220> FEATURE:
<223> OTHER INFORMATION: cdc42 peptide sequence
<220> FEATURE:
<221> NAME/KEY: Misc_Feature
<222> LOCATION: (1)..(1)
<223> OTHER INFORMATION: Unspecified amino acid
<220> FEATURE:
<221> NAME/KEY: Misc_Feature
<222> LOCATION: (45)..(45)
<223> OTHER INFORMATION: Unspecified amino acid

<400> SEQUENCE: 6

Xaa Gln Thr Ile Lys Cys Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Xaa Ile Gly
        35                  40                  45

<210> SEQ ID NO 7
<211> LENGTH: 47
<212> TYPE: PRT
<213> ORGANISM: Artificial Sequence
<220> FEATURE:
<223> OTHER INFORMATION: RhoG peptide sequence
```

-continued

```
<400> SEQUENCE: 7

Met Gln Ser Ile Lys Cys Val Val Val Gly Asp Gly Ala Val Gly Lys
1               5                   10                  15

Thr Cys Leu Leu Ile Cys Tyr Thr Thr Asn Ala Phe Pro Lys Glu Tyr
                20                  25                  30

Ile Pro Thr Val Phe Asp Asn Tyr Ser Ala Gln Ser Ala Val Asp
                35                  40                  45

<210> SEQ ID NO 8
<211> LENGTH: 50
<212> TYPE: PRT
<213> ORGANISM: Artificial Sequence
<220> FEATURE:
<223> OTHER INFORMATION: RhoA peptide sequence

<400> SEQUENCE: 8

Ser Met Ala Ala Ile Arg Lys Lys Leu Val Ile Val Gly Asp Val Ala
1               5                   10                  15

Cys Gly Lys Thr Cys Leu Leu Ile Val Phe Ser Lys Asp Gln Phe Pro
                20                  25                  30

Glu Val Tyr Val Pro Thr Val Phe Glu Asn Tyr Val Ala Asp Ile Glu
                35                  40                  45

Val Asp
    50

<210> SEQ ID NO 9
<211> LENGTH: 49
<212> TYPE: PRT
<213> ORGANISM: Artificial Sequence
<220> FEATURE:
<223> OTHER INFORMATION: RhoC peptide sequence

<400> SEQUENCE: 9

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
                20                  25                  30

Val Tyr Val Pro Thr Val Phe Glu Asn Tyr Ile Ala Asp Ile Glu Val
                35                  40                  45

Asp

<210> SEQ ID NO 10
<211> LENGTH: 49
<212> TYPE: PRT
<213> ORGANISM: Artificial Sequence
<220> FEATURE:
<223> OTHER INFORMATION: RhoB peptide sequence

<400> SEQUENCE: 10

Met Ala Ala Ile Arg Lys Lys Leu Val Val Val Gly Asp Gly Ala Cys
1               5                   10                  15

Gly Lys Thr Cys Leu Leu Ile Val Phe Ser Lys Asp Glu Phe Pro Glu
                20                  25                  30

Val Tyr Val Pro Thr Val Phe Glu Asn Tyr Val Ala Asp Ile Glu Val
                35                  40                  45

Asp

<210> SEQ ID NO 11
<211> LENGTH: 47
<212> TYPE: PRT
<213> ORGANISM: Artificial Sequence
```

```
-continued

<220> FEATURE:
<223> OTHER INFORMATION: H-Ras peptide sequence

<400> SEQUENCE: 11

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp
        35                  40                  45

<210> SEQ ID NO 12
<211> LENGTH: 47
<212> TYPE: PRT
<213> ORGANISM: Artificial Sequence
<220> FEATURE:
<223> OTHER INFORMATION: K-Ras peptide sequence

<400> SEQUENCE: 12

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp
        35                  40                  45

<210> SEQ ID NO 13
<211> LENGTH: 9
<212> TYPE: PRT
<213> ORGANISM: Artificial Sequence
<220> FEATURE:
<223> OTHER INFORMATION: mass spectrometry fragment
<220> FEATURE:
<221> NAME/KEY: Binding
<222> LOCATION: (2)..(2)
<223> OTHER INFORMATION: Binding to 6-TGTP

<400> SEQUENCE: 13

Thr Cys Leu Leu Ile Val Phe Ser Lys
1               5
```

COMPOSITIONS FOR INHIBITING REDOX-SENSITIVE GTPASES

CROSS REFERENCE TO RELATED APPLICATIONS

This application claims the benefit of U.S. Provisional Appl. No. 61/426,643, filed Dec. 23, 2010. The content of the aforesaid application is relied upon and incorporated by reference in its entirety.

REFERENCE TO A SEQUENCE LISTING SUBMITTED ELECTRONICALLY VIA EFS-WEB

The content of the sequence listing (Name: SEQ LISTING ST25.txt, Size: 5,828 bytes; and Date of Creation: Mar. 19, 2012) electronically submitted via EFS-Web is incorporated by reference in its entirety.

BACKGROUND OF THE INVENTION

1. Field of the Invention

The field of the invention relates to therapeutics. In particular, the field of the invention relates to the use of a redox-sensitive purine compound in combination with a redox agent to inhibit redox-sensitive GTPases, including Rho or Rab family GTPases.

2. Description of the Related Art

Small GTPases, including the Rho and Rab family GTPases, are involved in various cellular signaling events. Rho and Rab family GTPases belong to the Ras superfamily of GTPases. Rho and Rab GTPases, like all members of the Ras superfamily, function by cycling between inactive GDP-bound and active GTP-bound states (FIG. 1). Heo, J. (2011) *Antioxid. Redox Signaling* 14, 689-724. Various protein regulators such as guanine nucleotide exchange factors (GEFs) and GTPase-activating proteins control this GDP/GTP cycling. GEFs enhance the guanine nucleotide exchange (GNE) of these GTPases. Bos et al. (2007) *Cell* 129, 865-877. Dbl's big sister (Dbs), one of the Rho-specific GEFs, has been shown to be a RhoC GEF. Dietrich et al. (2009) *Biol. Chem.* 390, 1063-1077. Because cells contain relatively higher concentrations of GTP than GDP (Traut, T. W. (1994) *Mol. Cell. Biochem.* 140, 1-22), the GEF-mediated GNE of these GTPases populates the GTP-loaded active GTPases in cells. GTPase-activating proteins stimulate hydrolysis of the γ-phosphate of the bound GTP to produce inactive GDP-bound GTPases and free phosphates. Bos et al. (2007) *Cell* 129, 865-877.

Several Rho family proteins have been identified thus far, including RhoA, RhoB, RhoC, RhoG, Rac1, Rac2, Rac3, Cdc42, $TC^{10}$, TCL. Rho family members modulate various cellular processes, including cell morphology, movement and proliferation by mediating distinct cytoskeletal changes. Etienne-Manneville et al. (2002) *Nature* 420, 629-635. Misregulation of Rho GTPases has been implicated in many disorders, including cancer, heart and lung diseases, vascular diseases and diseases of the immune system. See e.g., van Leeuwen et al. (1995) *Oncogene* 11, 2215-2221; Fritz et al. (1999) *Int. J. Cancer* 81, 682-687; Boettner et al. (2002) *Gene* 286, 155-174; Benitah et al. (2003) *Rev. Oncol.* 5, 70-78; Numaguchi et al. (1999) *Circ. Res.* 85, 5-11; Laufs et al. (2000) *Circ. Res.* 87, 526-528; Satoh et al. (2006) *Proc. Natl. Acad. Sci. U.S.A.* 103, 7432-7437; Faried et al. (2006) *Eur. J. Cancer.* 42, 1455-1465; Touge et al. (2007) *Int. J. Oncol.* 30, 709-715.

RhoA has increasingly attracted clinical interest because of the emerging evidence of its role in the pathogenesis of several blood vessel diseases, including hypertension and atherosclerosis. Rabinovitch, M. (1991) *Toxicol. Pathol.* 19, 458-469; Numaguchi, K. (1999) *Circ. Res.* 85, 5-11; Laufs et al. (2000) *Circ. Res.* 87, 526-528; Alvarez de Sotomayor et al. (2001) *Eur. J. Pharmacol.* 415, 217-224; Kuzuya et al. (2004) *J. Cardiovasc. Pharmacol.* 43, 808-814; Kontaridis et al. (2008) *Circulation* 117, 1423-1435. Accordingly, it is considered an important target for future therapeutic agents. Budzyn et al. (2006) *Trends Pharmacol. Sci.* 27, 97-104; Shimokawa et al. (2007) *Trends Pharmacol. Sci.* 28, 296-302. Activation of RhoA results in downregulation of the myosin light chain phosphatase (MLCP) via upregulation of Rho kinase (ROCK). Halka et al. (2008) *Cardiovasc. Pathol.* 17, 98-102; Barman et al. (2009) *Vasc. Health Risk Manag.* 5, 663-671. Inactivation of the MLCP in turn populates its downstream MLC target in its dephosphorylated state, resulting in induction of vasorelaxation.

RhoC has increasingly attracted clinical interest because of the emerging evidence of its metastatic role in inflammatory breast cancer (IBC), which is the most lethal form of locally advanced breast cancer and annually accounts for approximately 6% of the new breast cancer cases in the United States. Jaiyesimi et al. (1992) *J. Clin. Oncol.* 10, 1014-1024. RhoC has been shown to be overexpressed in ~90% of human IBC lesions. van Golen et al. (1999) *Clin. Cancer. Res.* 5, 2511-2519; Clark, E. A., et al. (2000) *Nature* 406, 532-535. RhoC may also play a role in metastasis of various other tumors including hepatocellular and colon carcinomas. Wang et al. (2003) *World J. Gastroenterol.* 9, 1950-1953; Bellovin et al. (2006) *Oncogene* 25, 6959-6967.

Rab GTPases function via their specific effectors (Stenmark et al. (2001) *Genome. Biol.* 2, reviews 3007.3001-.3007; Jordens et al. (2005) *Traffic* 6, 1070-1077; Sandilands et al. (2008) *Trends Cell Biol.* 18, 322-329; Stenmark, H. (2009) *Nat. Rev. Mol. Cell Biol.* 10, 513-525) as regulators of distinct steps in membrane traffic pathways, including regulation of vesicle formation and movement. As with various Ras GTPases, misregulation of Rab GTPases results in development of a variety of cancers. Stein et al. (2003) *Adv. Drug Deliv. Rev.* 55, 1421-1437; Chia et al. (2009) *Biochim. Biophys. Acta* 1795, 110-116.

When small GTPases are redox sensitive, a cellular redox agent functions as their regulator. Heo, J. (2011) *Antioxid. Redox Signaling* 14, 689-724. Most Rho proteins, including Rac1 and Cdc42, are redox sensitive because they possess a single redox-sensitive cysteine ($Cys^{18}$, Rac1 numbering) in the GXXXXGK(S/T)C (SEQ ID NO:1) motif (monothiol). Heo, J., et al. (2005) *J. Biol. Chem.* 280, 31003-31010. A subset of the GXXXXGK(S/T)C (SEQ ID NO:1) motif is found in RhoA and RhoB. Heo et al. (2006) *Biochemistry* 45, 14481-14489. This subset contains a secondary cysteine ($Cys^{16}$, RhoA numbering) in addition to the primary redox-sensitive cysteine ($Cys^{20}$, RhoA numbering, which is equivalent to the Rac1 $Cys^{18}$) termed the GXXXCGK(S/T)C (SEQ ID NO:2) motif (dithiol). Although both the GXXXXGK(S/T)C (SEQ ID NO:1) and GXXXCGK(S/T)C (SEQ ID NO:2) motifs have the same redox sensitivity (Heo, J. (2005) *J. Biol. Chem.* 280, 31003-31010) the latter has an additional redox modulation function. Heo et al. (2006) *Biochemistry* 45, 14481-14489. An analysis of the RhoC crystal structure PDB 2GCO (Dias et al. (2007) *Biochemistry* 46, 6547-6558) in conjunction with a sequence analysis indicates that RhoC also possesses the GXXXCGK(S/T)C motif (SEQ ID NO:2). Ras GTPases contain a distinct redox-sensitive NKCD (SEQ ID NO:3) motif. Lander, H. M. (1997) *FASEB J.* 11, 118-124.

Furthermore, the RhoC Cys[20] site (the RhoC numbering is the same as the RhoA numbering) is located at the Rho nucleotide-binding site (Dias et al. (2007) *Biochemistry* 46, 6547-6558), but Ras Cys[118] (Harvey Ras numbering) is remote from the Ras nucleotide-binding site. Pai et al. (1989) *Nature* 341, 209-214. Various Rab family GTPases also possess the GXXXXGK(S/T)C (SEQ ID NO:1) motif (e.g., Rab1, Rab1A, Rab1B, Rab2, Rab2A/B, Rab4, Rab4A/B, Rab8, Rab8A/B, Rab10, Rab13, Rab14, Rab15, Rab19, and Sec4). See Heo, J. (2011) *Antioxid. Redox Signal.* 14, 689-724.

6-Thiopurine (6-TP) prodrugs, including 6-thioguanine (6-TG), 6-mercaptopurine, and azathioprine, are antimetabolites. They are widely used to treat cancers such as acute lymphoblastic leukemia, acute myeloid leukemia and adenocarcinomas, and autoimmune disorders such as inflammatory bowel disease, Crohn's disease and rheumatoid arthritis, as well as to treat organ transplant recipients. Elion, G. B. (1989) *Science* 244, 41-47; Langmuir et al. (2001) *Best Pract. Res. Clin. Haematol.* 14, 77-93; Gearry et al. (2005) *J. Gastroenterol. Hepatol.* 20, 1149-1157.

In cells, cellular enzymes convert inactive prodrug 6-TPs into the pharmacologically active 6-thioguanine nucleotide that can be grouped into deoxy-6-thioguanosine phosphate (6-TdGNP) and the 6-thioguanosine phosphate (6-TGNP). Elion, G. B. (1989) *Science* 244, 41-47; Langmuir et al. (2001) *Best Pract. Res. Clin. Haematol.* 14, 77-93; Gearry et al. (2005) *J. Gastroenterol. Hepatol.* 20, 1149-1157; McDonald et al. (1996) *Cancer Res.* 56, 2250-2255; Tiede et al. (2003) *J. Clin. Invest.* 111, 1133-1145; de Boer et al. (2007) *Nat. Clin. Pract. Gastroenterol. Hepatol.* 4, 686-694. Furthermore, depending on the number of ribose phosphates, 6-TGNP can be further classified as 6-thioguanosine diphosphate (6-TGDP) and triphosphate (6-TGTP). 6-TdGNP can be incorporated into the de novo synthesis of DNA as a form of 6-TG. 6-TG in DNA can then be recognized as a DNA lesion by the mismatch repair system, which results in induction of the mismatch repair-mediated cell apoptosis. Lage et al. (1999) *J. Cancer Res. Clin. Oncol.* 125, 156-165; Yan et al. (2003) *Clin. Cancer Res.* 9, 2327-2334; Karran, P. (2006) *Br. Med. Bull.* 79-80, 153-170. This 6-TG-mediated induction of mismatch repair is believed to be the main mechanism for the action of 6-TPs in the treatment of acute lymphoblastic leukemia.

In contrast to 6-TdGNP, neither the metabolic path of 6-TGNP nor its therapeutic activity and/or cytotoxicity has been clearly established. A few recent studies have addressed the action of 6-TGNP on small GTPases. It was recently shown that long-term treatment of Ras-activated tumor cells, such as bladder carcinoma (cell-line, T24) and fibrosarcoma (cell-line, HT1080), with 6-TG results in production of cellular 6-TGNP that targets Ras GTPase. Heo et al. (2010) *Biochemistry* 49, 3965-3976. This Ras-targeting action of 6-TGNP results in downregulation of Ras, which in turn terminates the tumorous growth of these cells. This Ras-targeting action of 6-TGNP extends beyond its effect on tumor cells and is considered cytotoxic because it deregulates the Ras GTP/GDP cycle.

It also has been shown that 6-TGNP targets and inactivates Rho GTPases such as Rac1. Tiede et al. (2003) *J. Clin. Invest.* 111, 1133-1145; Poppe et al. (2006) *J. Immunol.* 176, 640-651. This Rho GTPase-targeting action of 6-TGNP may be attributable to the therapeutic effect of 6-TPs on the immune system as well as on inflammatory bowel disease. Cuffari et al. (1996) *Can. J. Physiol. Pharmacol.* 74, 580-585; Maltzman et al. (2003) *J. Clin. Invest.* 111, 1122-1124; Quemeneur et al. (2003) *J. Immunol.* 170, 4986-4995. The therapeutic action of 6-TP in inflammatory bowel disease correlates with the Rac1-targeting 6-TGNP that blocks Rac1 GNE by its GEF Vav (Poppe et al. (2006) *J. Immunol.* 176, 640-651), although the details of the molecular mechanism by which this occurs are unknown.

Various hormone-related agents and Rho GTPase-downstream effector blockers, as anti-breast tumor drugs, are available. These available drugs are not Rho specific, and thus they also perturb many noncancer-related cellular signaling transductions. However, because these cellular signaling events are vital for cell survival, inhibition/deregulation of these signaling cascades is normally cytotoxic. A desirable chemotherapeutic agent for RhoC-overexpressed IBC is needed that would target RhoC directly and inhibit it. Direct targeting of tumorigenic RhoC by such an agent could reduce cytotoxicity while maximizing the antitumor effect. Similarly, therapeutic agents that directly target and inhibit RhoA and Rac1 activity for treating disorders including blood vessel diseases and autoimmune diseases, respectively, also are needed Inhibitors of various Rab family GTPases are also needed.

BRIEF SUMMARY OF THE INVENTION

In one aspect, the present invention provides compositions and methods for treating diseases or conditions associated with a redox-sensitive GTPase, such as a Rho or Rab family GTPase, in a subject, including diseases characterized by overexpression and/or misregulation of a Rho or Rab family GTPase. In accordance with the present invention, various diseases can be treated by inhibiting a Rho or Rab family GTPase using effective amounts of a redox-sensitive purine compound and an effective amount of a redox agent that enhances the inhibition of the Rho or Rab GTPase by the redox-sensitive purine compound.

In another aspect, the invention provides a composition for inhibiting a redox-sensitive GTPase protein, including a Rho or Rab family GTPase. The composition comprises an effective amount of a redox-sensitive purine compound and an effective amount of a redox agent. In some embodiments, the redox-sensitive purine compound is selected from the group consisting of a 6-thiopurine compound, including 6-thioguanine, and an 8-thiopurine compound, including 8-thioguanine. In some embodiments, the redox-sensitive purine is selected from the group of compounds having the general structure of formula I, wherein:

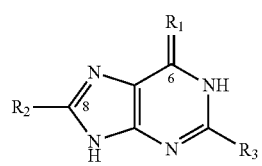

$R_1$ is selected from the group consisting of C6-thioxo (C6=S; in combination with C6 of the purine base); C6-thiol (C6-SH; in combination with C6 of the purine base); C6-selenal (C6=Se; in combination with C6 of the purine base); C6-selenol (C6-SeH; in combination with C6 of the purine base); C1-4 straight chain or branched chain alkyl, alkenyl, or alkynyl, wherein C1-4 are unsubstituted, singly substituted or multiply substituted, wherein the substituents are selected from the group consisting of thiol, thioxo, selenal, selenol, hydroxyl, halogen, amino, ketone, alkoxy, aldehyde and carboxylic acid; OH; and O;

wherein $R_2$ is selected from the group consisting of H; thiol (SH); selenol (SeH); C1-4 straight chain or branched chain alkyl, alkenyl, or alkynyl, wherein C1-4 are unsubstituted, singly substituted or multiply substituted, wherein the substituents are selected from the group consisting of thiol, thioxo, selenal, selenol, hydroxyl, halogen, amino, ketone, alkoxy, aldehyde and carboxylic acid; $NH_2$; and OH; wherein $R_3$ is selected from the group consisting of H, $NH_2$ and OH; with the proviso that at least one of $R_1$ or $R_2$ is a moiety that comprises a redox-sensitive functional group selected from the group consisting of thioxo, thiol, selenal and selenol.

The redox agent may be selected from any number of possible agents, including, for example, nitric oxide, nitrogen dioxide, dinitrogen trioxide, superoxide anion radical, hydrogen peroxide, and carbonate radical. The redox agent may also be produced indirectly by another agent that stimulates the production of the redox agent.

In another aspect, the invention provides a method for treating a disease associated with a redox-sensitive GTPase protein, including a Rho or Rab family GTPase protein, in a subject. The method comprises administering to the subject an effective amount of a redox-sensitive purine compound and an effective amount of a redox agent. In some embodiments, the redox-sensitive purine compound is selected from the group consisting of a 6-thiopurine compound, including 6-thioguanine, and an 8-thiopurine compound, including 8-thioguanine. Other redox-sensitive purine compounds may be selected from one of the groups of compounds of formula I above. The administration of the redox-sensitive purine compound with the redox agent inhibits the redox-sensitive GTPase protein (e.g., the Rho or Rab family GTPase) and the disease is treated.

Various diseases may be treated with the present invention. For example, various types and forms of cancer are treatable, including breast cancer and prostate cancer. In some embodiments, the invention provides a method of treating prostate cancer, comprising administering an effective amount of the redox-sensitive purine compound and an effective amount of the redox agent to the subject, wherein a redox-sensitive GTPase is inhibited. In some embodiments, the redox-sensitive GTPase is a Rho family GTPase. In one embodiment, the Rho family GTPase is a Rac protein. In some embodiments, the redox-sensitive GTPase is a Rab family GTPase. In some embodiments, the invention provides methods for treating cancer metastasis in a subject, comprising administering an effective amount of a redox-sensitive purine compound and an effective amount of a redox agent, wherein a Rho family GTPase is inhibited to treat the metastasis. In one embodiment, the Rho family GTPase is RhoC. The invention further provides methods for treating various blood vessel diseases, comprising administering an effective amount of a redox-sensitive purine compound and an effective amount of a redox agent to a subject, wherein a Rho or Rab family GTPase is inhibited to treat the blood vessel disease. In one embodiment, the Rho family GTPase is RhoA. In some blood vessel diseases, for example, hypertension, inhibiting RhoA promotes vasorelaxation of blood vessels. The invention further provides methods of treating immune related disorders, such as autoimmune disorders, comprising administering an effective amount of a redox-sensitive purine compound and an effective amount of a redox agent, wherein a Rho or Rab family GTPase is inhibited to treat the immune related disorder. In one embodiment, the Rho family GTPase is Rac1.

It is to be understood that both the foregoing general description and the following detailed description are exemplary, and thus do not restrict the scope of the invention.

BRIEF DESCRIPTION OF THE FIGURES

The skilled artisan will understand that the drawings, described below, are for illustration purposes only. The drawings are not intended to limit the scope of the present teachings in any way.

FIG. 2. Sequence alignment of Rho GTPases. A software ClustalX (version 1.83) was used for multiple sequence alignment of Rho GTPases. Sequence alignments longer than #49 (Rac1 numbering) were omitted for convenience, but the H and KRas sequences were shown for comparison.

FIG. 15. Detection of unusual 6-TGNP adduct from SUM and HME-RhoC cells. The ESI-MS and MS/MS methods to detect and identify a chemically modified RhoC residue are described elsewhere herein. (A) A mass peak of 1481.6 Da. was detected when SUM149 or HME-RhoC cells were treated with 6-TG. Given that the ESI-MS sample was prepared with co-IP using the RhoC antibody from the 6-TG treated SUM149 or HME-RhoC cells followed by trypsin digestion, the best candidate to give rise to the spectrum of the mass peak at 1481.6 Da. is a RhoC fragment TC[20]LLIVFSK crosslinked to 6-TGDP (TC[20]LLIVFSK-6-TGDP disulfide adduct) (SEQ ID NO:4). The left and right columns, respectively, denote any of the RhoC samples taken from SUM and HME cells. As indicated, a mixture of samples taken from untreated SUM149 and SUM102 cells was used as a control for the experiment shown in the left column. For the right column, a mixture of samples taken from HME-RhoC and HME-C205 RhoC cells was used as a control. (B) A MS/MS analysis was performed with the ESI-MS sample of 6-TG-treated SUM149 cells to identify a biomolecule that have a mass of 1481.6 Da. Major MS/MS peaks shown were best fit to the masses of ion fragments of the TC[20]LLIVFSK-6-TGDP adduct (SEQ ID NO:4): (i) the 1462.8 Da. fragment, formed upon loss of a $H_2O$ from the β-phosphate of the 6-TGDP moiety of TC[20]LLIVFSK-6-TGDP adduct (SEQ ID NO:4); (ii) the 1445.6 Da. fragment, formed by losing a $H_2O$ and a OH from the β- and α-phosphate of the 6-TGDP moiety of TC[20]LLIVFSK-6-TGDP adduct (SEQ ID NO:4); (iii) the 1400.4 Da. fragment, formed upon loss of COOH from the C-terminus of TC[20]LLIVFSK-6-TGDP adduct (SEQ ID NO:4) as well as a $H_2O$ and a OH from the β- and α-phosphate of the 6-TGDP moiety of TC[20]LLIVSK-6-TGDP adduct (SEQ ID NO:4); (iv) the 1022.8 Da. fragment, formed upon loss of the 6-TGDP moiety from TC[20]LLIVFSK-6-TGDP adduct (SEQ ID NO:4); and (v) the 978.3 Da. fragment, formed by losing the peptide C-terminus COOH and the 6-TGDP moiety from TC[20]LLIVFSK-6-TGDP adduct (SEQ ID NO:4). Taking into consideration the MS/MS result under our experimental conditions (e.g., SUM149 cells treated with 6-TG), the 1481.6 Da. molecule detected in the ESI-MS analysis is assigned to be the TC[20]LLIVFSK-6-TGDP disulfide adduct (SEQ ID NO:4). *Unassigned mass peaks.

DETAILED DESCRIPTION

Figure 1:
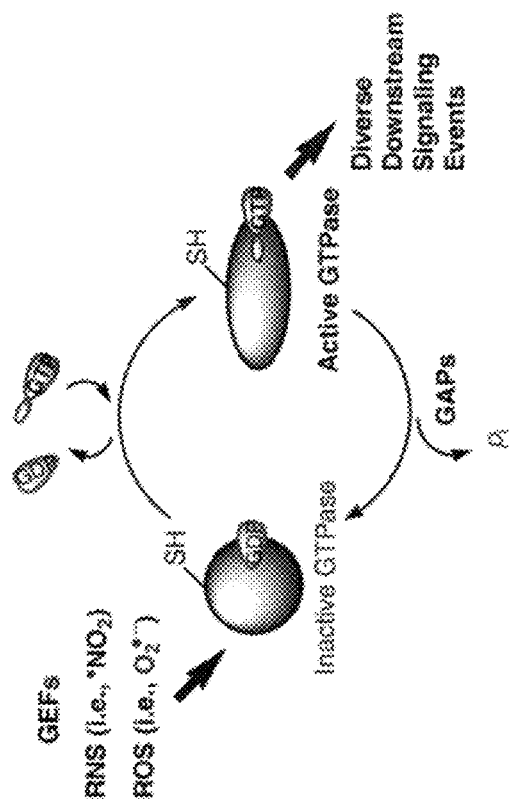
FIG. 1. (A) Classification of the Ras superfamily. (B) Small GTPase activity regulation cycle.

The present invention is based on the discovery that redox-sensitive purine compounds are capable of inhibiting the activity of Rho or Rab family GTPases in a redox-dependent manner. The Rho or Rab-targeting action of the redox-sensitive purine compounds is enhanced by the presence of a redox agent. Without being bound by theory, it is believed that the purine compound forms an adduct with the Rho or Rab GTPase, preventing GTP binding and thereby inactivating the Rho or Rab GTPase. In accordance with some of the embodiments as described herein, compositions comprising an effective amount of a redox-sensitive purine compound in combination with an effective amount of a redox agent are provided for administration and use in inhibiting Rho or Rab GTPases. In some embodiments, the compositions can be used to treat diseases associated with redox-sensitive GTPases such as Rho or Rab family GTPases, including cancer, blood vessel diseases, and immune related diseases.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the exemplary methods, devices, and materials are now described.

Unless otherwise noted, technical terms are used according to conventional usage. Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar technical references.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein "about" means±10% of the indicated value.

The terms "Rho GTPases" or "Rho family" refer to a subfamily of the Ras superfamily and are small, membrane-bound, Ras-related GTP-binding proteins that function by binding and hydrolyzing GTP. Rho GTPases function as molecular switches, cycling between an inactive GDP-bound conformation and an active GTP-bound conformation and includes, at least RhoA, RhoB, RhoC, RhoG, Rac1, Rac2, Rac3, Cdc42, TC$^{10}$, TCL. The term "Rab GTPase" also refers to a subfamily of the Ras superfamily and includes, at least Rab1, Rab1A, Rab1B, Rab2, Rab2A/B, Rab4, Rab4A/B, Rab8, Rab8A/B, Rab10, Rab13, Rab14, Rab15, Rab19 and Sec4.

The terms "Rac GTPase" or "Rac" refer to Rac1, Rac2, and/or Rac3.

Purines are a class of heterocyclic aromatic organic compounds comprising a pyrimidine ring fused to an imidazole ring. Purines include such compounds as purine, adenine, guanine, xanthine, hypoxanthine, isoguanine and uric acid. In accordance with the present invention, a "redox-sensitive purine" is a purine compound that is capable upon administration of inhibiting a Rho or Rab family protein in a redox dependent-manner.

Without being bound by theory, it is believed that the redox-sensitive purine is converted to an active compound, perhaps inside the cell, which in turn reacts with a redox-sensitive cysteine residue of the Rho or Rab family member, forming an adduct and inhibiting nucleotide exchange of the Rho or Rab family protein. A redox-sensitive cysteine residue (C) is found in the following motif of various Rho and Rab family proteins: GXXXXGK(S/T)C (SEQ ID NO:1) (FIG. 2). Rho proteins can be classified into two groups: (i) GXXXXGK(S/T)C (SEQ ID NO:1) motif-containing Rho GTPases (e.g., Rac1, Cdc42 and RhoG) (monothiol), which possess only one redox-active cysteine (Cys$^{18}$, Rac1 numbering; equivalent to RhoA Cys$^{20}$); and (ii) GXXXCGK(S/T)C (SEQ ID NO:2) motif-containing Rho GTPases (RhoA, RhoB, and RhoC), which have two redox-active cysteines (Cys$^{20}$, the primary; and Cys$^{16}$, the secondary cysteine; RhoA numbering) (dithiol). The redox-sensitive purine that can be used in accordance with the present invention is not limiting. In some embodiments, the redox-sensitive purine compound is a thiopurine compound (TP). In some embodiments, the redox-sensitive purine is a guanine analog. In some embodiments, the redox-sensitive purine is substituted at the C6 position of the purine base with a moiety that comprises a redox-sensitive functional group. In some embodiments, the redox-sensitive purine is substituted at the C8 position of the purine base with a moiety comprising a redox-sensitive functional group. In some embodiments, the redox-sensitive functional group is selected from the group consisting of thiol, thioxo, selenal and selenol and combinations thereof. In some embodiments, the redox-sensitive purine is a 6-thiopurine compound, such as 6-thioguanine. In some embodiments, the redox-sensitive purine is an 8-thiopurine compound, such as 8-thioguanine. In some embodiments, the redox-sensitive purine is selected from the group of compounds having the general structure of formula I, wherein:

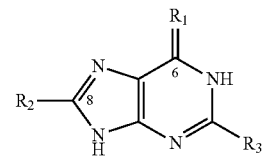

$R_1$ is selected from the group consisting of C6-thioxo (C6=S; in combination with C6 of the purine base); C6-thiol (C6-SH; in combination with C6 of the purine base); C6-selenal (C6=Se; in combination with C6 of the purine base); C6-selenol (C6-SeH; in combination with C6 of the purine base); C1-4 straight chain or branched chain alkyl, alkenyl, or alkynyl, wherein C1-4 are unsubstituted, singly substituted or multiply substituted, wherein the substituents are selected from the group consisting of thiol, thioxo, selenal, selenol, hydroxyl, halogen, amino, ketone, alkoxy, aldehyde and carboxylic acid; OH; and O;

wherein $R_2$ is selected from the group consisting of H; thiol (SH); selenol (SeH); C1-4 straight chain or branched chain alkyl, alkenyl, or alkynyl, wherein C1-4 are unsubstituted, singly substituted or multiply substituted, wherein the substituents are selected from the group consisting of thiol, thioxo, selenal, selenol, hydroxyl, halogen, amino, ketone, alkoxy, aldehyde and carboxylic acid; $NH_2$; and OH;

wherein $R_3$ is selected from the group consisting of H, $NH_2$ and OH;

with the proviso that at least one of $R_1$ or $R_2$ is a moiety that comprises a redox-sensitive functional group selected from the group consisting of thioxo, thiol, selenal and selenol.

In some embodiments, the redox-sensitive purine can include 8-thioguanine (2-amino-8-mercapto-1H-purin-6

(9H)-one), 8-methylthioguanine (2-amino-8-(mercaptomethyl)-1H-purin-6(9H)-one), 7-methylthioguanine (2-amino-7-(mercaptomethyl)-8,9-dihydro-1H-purin-6(H)-one), and 7-thioguanine (2-amino-7-mercapto-8,9-dihydro-1H-purin-6(H)-one). 7- and 8-thioguanines and other purine analogs are commercially available (Azopharma Drug Development Services, Miramar, Fla.). 8-thiopurines including 8-thioguanine is commercially available from USBiological: http://www.usbio.net/item/A1378-06.

In some embodiments, the redox-sensitive purine can include 6-thiopurine, 8-thiopurine, and analogs thereof. Commercially available 6-thiopurines include azathioprine (AZA) (Imuran® sold by GlaxoSmithKline and available as a generic); 6-mercaptopurine (6-MP) (Purinethol® sold by Teva and available as a generic); 6-thioguanine (6-TG) (Tabloid® sold by GlaxoSmithKline and available as a generic). AZA and 6-MP are prodrugs converted into 6-thioguanine in cells, which is then converted into its active form 6-thioguanine nucleotide (6-TGNP). 8-thiopurine can be cellularly converted into its active form 8-thioguanine nucleotide (8-TGNP)

Also included within the scope of the redox-sensitive purine compounds are pharmaceutically acceptable derivatives. By "a pharmaceutically acceptable derivative" is meant any pharmaceutically or pharmacologically acceptable salt, ester or salt of such ester of a compound according to the invention. The redox-sensitive purine compounds may be converted into a pharmaceutically accepted ester by reaction with an appropriate esterifying agent, e.g. an acid halide or anhydride. The redox-sensitive purine compounds including esters thereof, may be converted into pharmaceutically acceptable salts thereof in conventional manner, e.g. by treatment with an appropriate acid. An ester or salt of an ester may be converted into the parent compound, e.g. by hydrolysis.

In some embodiments, the redox-sensitive purine is capable of inhibiting a Rho family member selected from the group consisting of RhoA, RhoB, RhoC, RhoG, Rac1, Rac2, Rac3, Cdc42, TC$^{10}$, TCL, and combinations thereof. In other embodiments, the redox-sensitive purine is capable of inhibiting a Rab family member selected from the group consisting of Rab1, Rab1A, Rab1B, Rab2, Rab2A/B, Rab4, Rab4A/B, Rab8, Rab8A/B, Rab10, Rab13, Rab14, Rab15, Rab19, Sec4 and combinations thereof.

The redox agent that can be used in accordance with the invention is not limiting, provided, however, that it is capable of enhancing the inhibition of a Rho or Rab family protein when used in conjunction with a redox-sensitive purine. In some embodiments, the redox agent is selected from a reactive oxygen species (ROS) or a reactive nitrogen species (RNS). In some embodiments, the redox agent is selected form the group consisting of nitric oxide (NO), nitrogen dioxide ($.NO_2$), nonradical higher oxides such as dinitrogen trioxide ($N_2O_3$), superoxide anion radical ($O_2.^-$), carbonate radical, hydrogen peroxide, hydroxyl radical and combinations thereof. The redox agent also may be produced indirectly by another agent that stimulates the production of the redox agent. Accordingly, these other agents are also construed as "redox agents" as used herein. Generally, any redox agent is useful in the invention that facilitates formation of a disulfide bond or adduct between Rho or Rab proteins and the active form of the redox-sensitive purine compound, including 6- and 8-thioguanine compounds.

In some embodiments, nitric oxide releasing agents are used, either directly or indirectly by administering compounds that stimulate cellular nitric oxide releasing agents. Direct nitric oxide releasing agents (also called NO donors) include: peroxynitrite; sodium nitroprusside (SNP) (brand name: Nitropress); diethylenetriamine nitric oxide adduct (DETA/NO); S-Nitrosoglutathione (GSNO); S-nitrosothiols such as S-nitroso-glutathione, S-nitroso-N-acetylpenicillamine, S-nitroso-albumin, S—NO—N-acety-L-cysteine, S—NO-diclofenac; nitric oxide-releasing aspirins; S-nitroso nonsteroidal antiinflammatory drugs (S-NITROSO NSAIDs); nitric oxide releasing NSAIDs; 2-acetoxybenzoate 2-(2-nitroxy-methyl)-phenyl ester (NCX-4016) and 2-acetoxybenzoate 2-(2-nitroxy)-butyl ester; phosphodiesterase inhibitors (e.g., sildenafil); and organic nitrate and nitrite esters, such as nitroglycerin, amyl nitrite, isosorbide dinitrate, isosorbide 5-mononitrate, and nicorandil. See also Napoli et al. (2003) *Annu. Rev. Pharmacol. Toxicol.* 43, 97-123, describing nitric oxide-releasing drugs. Indirect drugs that stimulate cellular nitric oxide releasing agents include: drugs such as 1,4-dihydropyridine calcium channel blockers (CCBs) that stimulate nitric oxide synthase (NOS) to produce cellular nitric oxide; ACE inhibitors; ANGII Type 1 receptor antagonists; statins; and drugs that stimulate cyclooxygenase-1 (COX-1) and/or cyclooxygenase-2 (COX-2) to produce cellular superoxide anion radical, which also facilitates disulfide bond formation.

In some embodiments, the invention provides compositions comprising an effective amount of a redox-sensitive purine compound and an effective amount of a redox agent. As used herein an "effective amount" of a redox-sensitive purine is any amount which, when administered, inhibits Rho or Rab family GTPase activity. The activity can be modulated in a cell, a tissue, a whole organism, in situ, in vitro (test tube, a solid support, etc.), in vivo, or in any desired environment. As used herein, an "effective amount" of a redox agent is any amount which, when used in conjunction with a redox-sensitive purine, enhances the inhibition of Rho or Rab family GTPase activity.

In some embodiments, the composition comprises an effective amount of a redox-sensitive purine compound and an effective amount of a redox agent in further combination with one or more therapeutic agents for the treatment of the diseases or conditions as described herein.

The redox-sensitive purine compound according to the invention in combination with the redox agent may be administered for therapy by any suitable route including oral, rectal, nasal, topical (including transdermal, buccal and sublingual), vaginal and parenteral (including subcutaneous, intramuscular, intravenous and intradermal). It will be appreciated that the preferred route will vary with the condition and age of the recipient, the nature of the disease to be treated and the redox-sensitive purine and redox agent.

In some embodiments, a suitable dose of the redox-sensitive purine compound for each of the conditions described herein will be in the range of about 0.01 to about 250 mg per kilogram body weight of the recipient (e.g. a human) per day. In some embodiments, the dose is in the range of about 0.1 to about 100 mg per kilogram body weight per day and in other embodiments, in the range of about 1.0 to about 20 mg per kilogram body weight per day. In some embodiments, the dose is in the range of about 0.5±5.0 mg/kg/day, about 0.5±2.5 mg/kg/day, or about 0.5±1.5 mg/kg/day. Unless otherwise indicated, all weights of the redox-sensitive purine are calculated as the parent compound; for salts or esters thereof, the weights would be increased proportionally. In some embodiments, the desired dose is presented as two, three, four, five, six or more sub-doses administered at appropriate intervals throughout the day. These sub-doses may be administered in unit dosage forms, for example, containing 5 to 150 mg, 10 to 100 mg, or 25 to 50 mg of redox-sensitive purine per unit dosage form.

In some embodiments, the redox-sensitive purine is administered to achieve peak plasma concentrations of from about 0.025 to about 100 µM, in some embodiments, about 0.1 to about 70 µM, or about 0.25 to about 50 µM. In some embodiments, this may be achieved, for example, by the intravenous injection of a 0.1 to 5% solution of the redox-sensitive purine, optionally in saline, or orally administered as a bolus containing about 0.1 to about 250 mg/kg of the redox-sensitive purine. In some embodiments, desirable blood levels may be maintained by a continuous infusion to provide about 0.01 to about 5.0 mg/kg/hour or by intermittent infusions containing about 0.1 to about 15 mg/kg of the redox-sensitive purine.

The redox agent may be administered at any suitable dosage, and in some embodiments may be administered at a dosage such that a cellular concentration of from about 0.5 µM to about 10 µM is achieved. In some embodiments, the cellular concentration of redox agent is about 3 µM.

While it is possible for the redox-sensitive purine and the redox agent to be administered alone it is preferable that they be administered as a pharmaceutical formulation. In some embodiments, the formulations of the present invention comprise the redox-sensitive purine in combination with the redox agent, as defined above, together with one or more acceptable carriers thereof and optionally other therapeutic agents. In some embodiments, each carrier must be "acceptable" in the sense of being compatible with the other ingredients of the formulation and not injurious to the patient. Formulations include those suitable for oral, rectal, nasal, topical (including transdermal buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredients with the carrier which constitutes one or more accessory ingredients. In general, the formulations are prepared by uniformly and intimately bringing into association the active ingredient with liquid carriers or finely divided solid carriers or both, and then if necessary shaping the product.

Compositions suitable for transdermal administration may be presented as discrete patches adapted to remain in intimate contact with the epidermis of the recipient for a prolonged period of time. Such patches suitably contain the redox-sensitive purine in combination with the redox agent 1) in an optionally buffered, aqueous solution or 2) dissolved and/or dispersed in an adhesive or 3) dispersed in a polymer. A suitable concentration of the active compounds is about 1% to 25%, or about 3% to 15%.

Formulations of the present invention suitable for oral administration may be presented as discrete units such as capsules, cachets or tablets each containing a predetermined amount of the active ingredient(s); as a powder or granules; as a solution or a suspension in an aqueous or non-aqueous liquid; or as an oil-in-water liquid emulsion or a water-in-oil liquid emulsion. The active ingredient(s) may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient(s) in a flavored basis, usually sucrose and acacia or tragacanth; pastilles comprising the active ingredient in an inert basis such as gelatin and glycerin, or sucrose and acacia; and mouthwashes comprising the active ingredient(s) in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient(s) such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient(s).

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further provides methods of inhibiting a redox-sensitive GTPase, including a Rho or Rab family GTPase, comprising administering an effective amount of a redox-sensitive purine compound and an effective amount of a redox agent. In some embodiments, the GTPase is present inside a cell, including in a whole organism, tissue, organ or cell culture system. In some embodiments, the GTPase is inhibited in vitro or in a cell-free system.

The present invention further provides methods of treating certain diseases or conditions which are associated with redox-sensitive GTPases, including Rho or Rab family GTPases, in a subject, including conditions characterized by overexpression and/or misregulation of Rho or Rab family GTPases.

As used herein, "treatment," "treating" or "treat" includes both therapeutic and prophylactic treatments. Accordingly, the compounds and compositions can be used at very early stages of a disease, or before early onset, or after significant progression.

For example, in some embodiments, the invention provides methods of treating a disease or condition associated with a Rho or Rab family GTPase in a subject in need of treatment, comprising administering to the subject one or more compositions of the invention.

In some embodiments, the diseases or conditions to be treated are associated with a Rho family GTPase selected from the group consisting of RhoA, RhoB, RhoC, RhoG, Rac1, Rac2, Rac3, Cdc42, TC[10], TCL and combinations thereof. In other embodiments, the diseases or conditions to be treated are associated with a Rab family GTPase selected from the group consisting of Rab1, Rab1A, Rab1B, Rab2, Rab2A/B, Rab4, Rab4A/B, Rab8, Rab8A/B, Rab10, Rab13, Rab14, Rab15, Rab19, Sec4, and combinations thereof.

In some embodiments, the invention provides methods of treating a disease or condition associated with a Rho or Rab family GTPase in a subject in need of treatment, comprising administering to the subject an effective amount of a redox-sensitive purine compound and an effective amount of a redox agent. In some embodiments, the redox agent enhances the formation of an adduct between a redox-sensitive residue of a Rho or Rab family GTPase and the active form of the redox-sensitive purine compound, thereby inhibiting the Rho or Rab GTPase. In some embodiments, the Rho or Rab GTPase harbors a GXXXXGK(S/T)C (SEQ ID NO:1) motif that is redox-sensitive. In some embodiments, the Rho or Rab GTPase harbors a GXXXCGK(S/T)C (SEQ ID NO:2) motif that is redox-sensitive.

In some embodiments, the subject to be treated is a mammal. Mammals that can be treated in accordance with the invention, include, but are not limited to humans, dogs, cats, horses, mice, rats, guinea pigs, sheep, cows, pigs, monkeys, apes and the like.

The redox-sensitive purine compound and the redox agent can be administered simultaneously, in either separate or combined compositions, or at different times, e.g. sequentially such that a combined effect is achieved.

In some embodiments, the disease or condition to be treated is cancer. In some embodiments, the disease or condition to be treated is cancer metastasis. In some embodiments, the cancer or cancer metastasis is selected from the group consisting of prostate cancer, such as high-grade prostatic intraepithelium neoplasia (HG-PIN), breast cancer, including inflammatory breast cancer (IBC), ovarian cancer, pancreatic cancer, lung cancer, gastric cancer, hepatocellular carcinoma, bladder cancer, colorectal cancer and cutaneous melanoma. In some embodiments of the methods for treating cancer, the Rho family GTPase that is inhibited is RhoC. For example, RhoC has been shown to be overexpressed in several tumors such as prostate, breast, ovarian, lung, pancreas, and gastric cancer as well as in bladder, colorectal and cutaneous melanoma, although other cancer-generating Ras GTPases are not overexpressed. cDNA array analyses have also implicated overexpress ion of RhoC in a melanoma model of metastasis.

In some embodiments, various thiopurine drugs and a redox agent effectively inhibit cancer metastasis, as exemplified by their effects on the motility of SUM cells derived from human inflammatory breast cancer (IBC) cells and RhoC-overexpressed human mammary epithelium (HME-RhoC) cells as described herein in the Examples. Without being bound by theory, it is believed that the thiopurine-mediated inhibition of cell motility occurs because the thiopurine targets and inhibits RhoC. A molecular mechanism for the thiopurine mediated RhoC inhibition also has been shown in which 6-TPs are converted in cells into the 6-thioguanosine phosphate (6-TGNP), which in turn reacts with the Cys[20] side chain of the RhoC GXXXXGK(S/T)C (SEQ ID NO:1) motif to produce a 6-TGNP-RhoC disulfide adduct. A redox agent enhances this disulfide formation process. The adduct formed impedes RhoC guanine nucleotide exchange, which populates an inactive RhoC. This result is in contrast to the targeting of Ras by 6-TG-redox agent combinations, which was minimal because the redox-active Ras cysteine is not located at its nucleotide-binding site. In some embodiments, formation of the Rho protein-disulfide adduct occurs in GTPases that possess the GXXXXGK(S/T)C (SEQ ID NO:1) motif such as RhoC, RhoA, and Rac. RhoC therefore is a target for treatment of diseases related to RhoC by using a combination of redox-sensitive purine compounds and a redox agent as an effective chemotherapeutic agent to inhibit or terminate the metastasis of IBC. In some embodiments of treating cancer metastasis, for example, by inhibiting RhoC, the redox-sensitive purine administered is 8-thioguanine (8-TG) and the redox agent is the nitric oxide (NO) donor DETA/NO.

In some embodiments, the disease or condition to be treated is prostate cancer. In some embodiments, the Rho family GTPase that is inhibited is a Rac protein. In some embodiments, high-grade prostatic intraepithelium neoplasia (HG-PIN) is treated. HG-PIN, like prostate cancer, is associated with overexpression of Rac proteins.

In some embodiments, the disease or condition to be treated is a blood vessel disease. In some embodiment, the Rho family GTPase that is inhibited is RhoA. In some embodiments, the blood vessel disease is hypertension, and the methods of the invention promote vasorelaxation of blood vessels, and improvement of the condition.

In some embodiments, the disease or condition to be treated is immune related. In some embodiments, the disease or condition involves T-cells, which includes, but is not limited to, cell-mediated hypersensitivity, such as delayed type hypersensitivity and T-cell-mediated cytotoxicity, and transplant rejection; autoimmune diseases, such as systemic lupus erythematosus, Sjogren syndrome, systemic sclerosis, inflammatory-myopathies, mixed connective tissue disease, and polyarteritis nodosa and other vasculitides, inflammatory bowel disease, ulcerative colitis and rheumatoid arthritis. In some embodiments, the Rho family GTPase that is inhibited is Rac1.

The redox-sensitive purine that can be administered to treat the diseases or conditions described herein is not limiting and includes all of the compounds as described herein. In some embodiments, the redox-sensitive purine is a 6-thiopurine, such as 6-thioguanine. In some embodiments, the redox-sensitive purine is a 8-thiopurine, such as 8-thioguanine. In some embodiments, the redox-sensitive purine is a compound of formula (I).

In some embodiments, the invention further provides methods of screening for compounds that inhibit a redox-sensitive GTPase protein, including a Rho or Rab family GTPase protein. In some embodiments, the methods comprise contacting a composition comprising a Rho or Rab family GTPase with a redox-sensitive compound, optionally in the presence of a redox agent, wherein the Rho or Rab family GTPase and the redox-sensitive compound form an adduct. In some embodiments, the method further comprises detecting the adduct and/or assaying for the activity of the Rho or Rab family GTPase. In some embodiments, the compound is a redox-sensitive purine as described herein. In some embodiments, the compound is not a purine compound, but is redox-sensitive and is capable of forming an inhibitory adduct with a Rho or Rab family GTPase.

The modulation or inhibition of Rho or Rab family GTPases can be measured according to any assay typically used to measure Rho or Rab GTPase activity. In some embodiments, the activity can be measured by analyzing GTP hydrolysis, binding to Rho-GEF or Rab-GEF etc. Various assay methods for monitoring the activation state of a Rho GTPase, for example, are known and can be incorporated into the screening methods of the invention. One assay, the Rho effector pull-down assay, was originally developed for RhoA GTPases (Ren et al. *EMBO J.* 18: 578-585 (1999)) and for Rac1/Cdc42 GTPases (Benard et al. *J. Biol. Chem.* 274: 13198-13204 (1999)) and is a classical and widely used assay. The method involves capture of activated Rho GTPase proteins by effectors bound to beads, release of the GTPase protein from the beads, separation of the beads from the released GTPase protein, followed by SDS-PAGE and analysis of the GTPase protein by western blotting. There are several cell-based assays that use fluorescent bio-probes to detect activated Rho GTPases (Pertz et al. *J. Cell Sci.* 117: 1313-1318 (2004)). Several versions of this type of assay rely on a reporter system to monitor in vivo Rho GTPase activation. These cell-based assays, therefore, do not monitor the actual endogenous levels of the GTPase (Itoh et al. *Mol. Cell Biol.* 22: 6582-6591 (2002); Pertz et al. *Nature* 440: 1069-1072 (2006); Vadim et al. *Science* 290: 333-337 (2000)). Other versions of cell-based assays use effector domains linked directly to an environmental dye to monitor endogenous in vivo GTPase activation. An enzymatic based method to detect Rho activation has been described (Chen et al. *J. Biol. Chem.* 278: 2807 (2003)). The assay utilizes GST-effector-GBD to affinity precipitate active GTP-Rho. GTP is eluted and converted to ATP in a coupled enzymatic assay. ATP is then measured by the firefly luciferase method.

Figure 14:
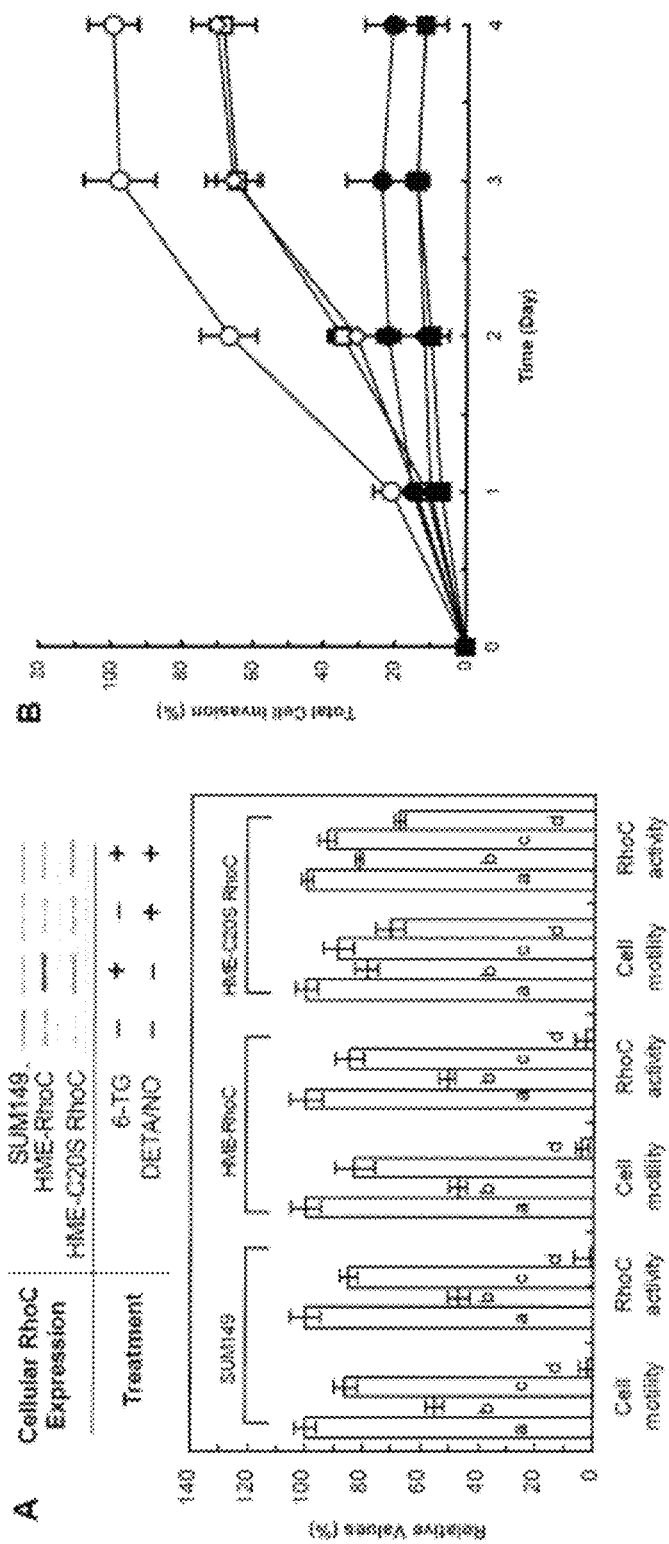
FIG. 14. Determination of cell invasiveness in the presence and absence of thiopurines and/or redox agents. (A) Experimental procedures for the determination of cellular RhoC expression in cells treated with 6-TG and/or DETA/NO, as well as for the determination of cell motility using Matrigel and the corresponding RhoC activity of cells treated with 6-TG and/or DETA/NO, are described elsewhere herein. The average number and standard error of triplicate measurements of SUM149 cells from invasion through the Transwell filter pores to the lower chambers in the absence of 6-TG and DETA/NO were determined to be 130±4. All other cell invasion results were normalized against the average value of the SUM149 cell invasion that was set to be 100%, and represent average and standard error values from triplicate measurements: a, cells untreated with 6-TG and DETA/NO; b, cells treated with only 6-TG; c, cells treated with only DETA/NO; and d, cells treated with both 6-TG and DETA/NO. Western blot analysis representing the total expression of RhoC in these cells also is shown. (B) Experimental procedures for the determination of the time-dependent motility of cells using the QCM Cell Invasion Assay kit in the presence and absence of 6-TG and DETA/NO are described elsewhere herein. The determined maximal mean value of the optical density and standard error of triplicate measurements corresponding to the invasion of SUM149 cells from the upper to the lower chamber through filter pores without treatment with 6-TG and DETA/NO at the day four of experiment was estimated to be 1.13±0.16. All colorimetrically determined optical density values associated with cell invasion under these experimental conditions were normalized against the mean value of optical density for the value of the SUM149 cell invasion in the absence of 6-TG and DETA/NO at the day four of experiment that was set to be 100%. All values represent mean and standard error values from triplicate measurements: SUM149 cells untreated (○) or treated (●) with 6-TG and DETA/NO; SW480 cells untreated (□) or treated (■) with 6-TG and DETA/NO; and HCCLM3 cells untreated (◇) or treated (◆) with 6-TG and DETA/NO.

In some embodiments, downstream or biological effects of Rho or Rab proteins can be analyzed to screen for inhibitory Rho or Rab GTPase compounds. In some embodiments, cell invasiveness is assayed as a downstream effect of Rho GTPase proteins (See FIG. 14 and the Example 3, herein). In some embodiments, changes in the cytoskeleton, or vesicular trafficking can be detected in the presence and the absence of the redox-sensitive compound, as an indirect means of detecting Rho or Rab GTPase activity. An automated cell-based Rho activation assay has also been described (Teusch et al., 2006, Assay and Drug Devel., 4: 133) based on the ability of Rho to regulate the actin cytoskeleton. A Rho GTPase activation assay that measures cytoskeletal changes is also discussed in U.S. Application Pub. No.: 20060177816. The disclosures of the above cited documents which pertain to methods for assaying of Rho GTPase activity are incorporated by reference herein.

Various cell types can be screened for Rho or Rab GTPase inhibition in accordance with the above described methods, including cancer cells, such as breast cancer cells, immune cells, such as T-cells, and smooth muscle cells. In addition, specific Rho or Rab GTPases can be screened for inhibition. In some embodiments, Rho GTPase inhibitors can be identified that are more selective for a particular Rho GTPase family member over other family members. The identification of Rho or Rab selective inhibitors will likely improve any toxicity that might be associated with use of inhibitors that target all Rho or Rab family GTPases.

The examples disclosed below illustrate embodiments of the invention and are not intended to limit the scope. It is evident to those skilled in the art that modifications or variations can be made to the embodiments described herein without departing from the teachings of the present invention.

EXAMPLES

Example 1

Small GTPase-Targeting Action of 6-Thioguanine and 8-Thioguanine

This example provides studies on the investigations of the Rho and Ras cellular targeting action of 6-thioguanine and 8-thioguanine with a redox agent.

Actions of 6-thioguanine on Rho.

RhoC-overexpressed mammary epithelium (HME-RhoC) cells were used to examine the effect of 6-TG and/or a redox agent on RhoC. When HME-RhoC cells were treated with 6-TG (1 μM), nearly 80% of the cells underwent apoptosis within a day. A decrease in the cell population of HME-RhoC cells also was observed when other 6-TG analogs such as 6-MP and AZA were used (not shown). This result is consistent with previous observations that 6-TG and its analogs induce cell death for certain tumor cell lines via altering the stability of DNA (Lage et al. *J. Cancer Res. Clin. Oncol.* 125, 156-165 (1999); Yan et al. Clin. Cancer Res. 9, 2327-2334 (2003); Kaba et al. *J. Clin. Oncol.* 15, 1063-1070 (1997); Bae et al. *Cancer Lett.* 126, 97-104 (1998); Matheson et al. *Adv. Exp. Med. Biol.* 457, 579-583 (1999); Liu et al. *Leukemia* 16, 223-232 (2002); Morgan et al. *Cancer Res.* 54, 5387-5393 (1994)). Some cells (20%-25% of the initial cells), however, persistently resisted additional treatments with 6-TG and even slowly regrew in the presence of 6-TG or its analogs such as 6-MP and AZA. It is unclear if the resistance of these cells to 6-TG or its analogs is directly induced by treatment with 6-TG or its analogs. However, this resistance could be a problem for patients over the course of long-term treatment with 6-TG or its analogs (de Boer et al. *Nat. Clin. Pract. Gastroenterol. Hepatol.* 4, 686-694 (2007); Karran et al. *Nat. Rev. Cancer* 8, 24-36 (2008); Cuffari et al. *Can. J. Physiol. Pharmacol.* 74, 580-585 (1996)).

Figure 5:
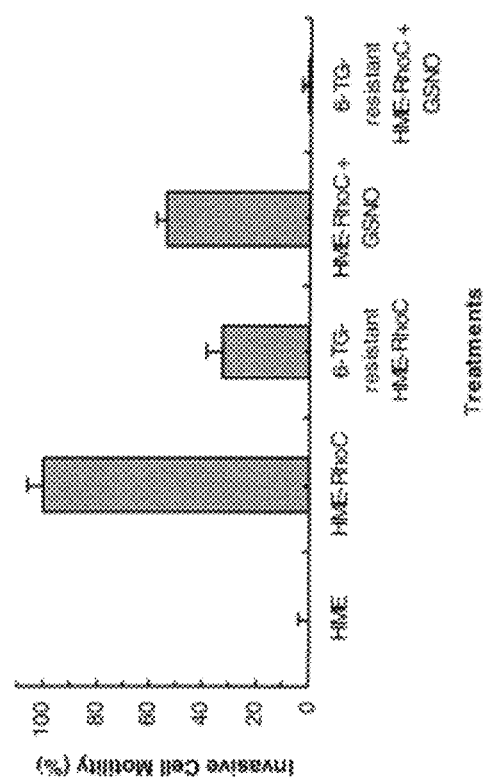
FIG. 5. Determination of cell invasiveness in the presence and absence of 6-thiopurine and/or a redox agent. The top chamber of a Transwell filter (6.5 mm with 8 μm pores, Costar; Corning, N.Y.) was coated with a 10 μL aliquot of 10 mg/mL Matrigel (BD Biosciences, Bedford Mass.), and the lower chamber of the Transwell was filled with either serum-free or serum-containing media. Sample cells (e.g., 6-TG-resistant HME-RhoC cells) were prepared to resuspend cells in a serum-free medium with 0.1% BSA at a concentration of $4 \times 10^5$ cells/mL. At this point, neither 6-thiopurine nor GSNO were added to the cells. The sample cells (0.5 mL) were added to the top chamber of a Transwell filter and were incubated for 24 h at 37° C. in a 10% CO2 incubator. The Transwell filters were fixed with methanol, stained with H&E, and cells in the serum-containing samples were counted. The number of cells that had invaded the serum-free medium-containing lower chambers was used as a control background. Results are given as percent invasion over that seen in HME-RhoC cells (100%) and represent mean and standard error values from triplicate measurements.

When the 6-TG-resistant HME-RhoC cells were further treated with an NO donor (diethylenetriamine/NO, DETA/NO or S-nitrosoglutathione, GSNO; 10 μM), the invasiveness of the 6-TG-resistant HME-RhoC cells drastically declined (retained less than 5% of their original invasiveness; FIG. 5). Because the half-life of redox agents, GSNO and DETA/NO, is ~8 and ~20 h, respectively, at pH 7.4 and 37° C. (Maragos et al. *J. Med. Chem.* 34, 3242-3247 (1991); Mooradian et al. *J. Cardiovasc. Pharmacol.* 25, 674-678 (1995); Floryszak-Wieczorek et al. *Planta* 224, 1363-1372 (2006)), their treatment intervals were 8 and 20 h to ensure the concentration of NO remained for the duration of the experiment at a minimal 50% of the initial concentration of NO in the culture media.

Figure 6:
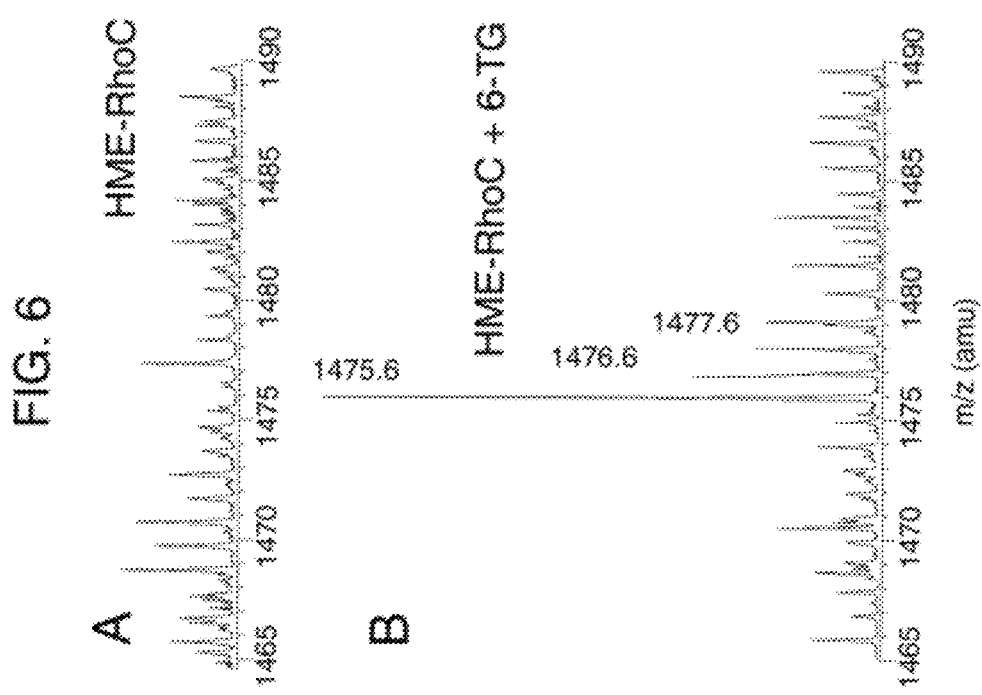
FIG. 6. Detection of unusual 6-TGNP adduct from HME-RhoC cells. HME-RhoC cells were treated with 6-TG (1 μM; every 48 h) for 5 days and were washed twice in phosphate-buffered saline. A monoclonal RhoC antibody (Biocompare, South San Francisco, Calif.) and a "Mammalian Co-Immunoprecipitation Kit" (Pierce) were used for the analyses of the RhoC 6-TGNP interaction in HME-RhoC cells. The immunoprecipitated RhoC sample was suspended in 50% methanol:0.1% formic acid. The protein portion and RhoC-released nucleotide were separated by a brief centrifugation (3000×g for 5 min). The protein portion from the immunoprecipitated RhoC was resuspended in the assay buffer (pH 7.5), digested with trypsin for 10 h, and analyzed with MALDI-TOF tandem mass spectrometry. The MALDI-TOF peak at 1476.6 Da represents peptide-6-TGDP adduct; $TC^{20}$LLIVFSK-6-TGDP (SEQ ID NO:4). (A) and (B), respectively, denote any of the RhoC samples taken from cell culture without and with treatment of 6-TG (1 μM; every 48 h).

To determine if the loss of invasive cell mobility associated with RhoC was attributable solely to either 6-TG (or its analogs) or to the combined effect of 6-TG with a redox agent, RhoC in a complex with 6-TGNP was probed with RhoC antibody, digested with trypsin, and analyzed with Matrix-Assisted Laser Desorption/Ionization time-of-flight (MALDI-TOF) (FIG. 6). An unusual mass peak, 1475.6 Da., was detected that is assigned as an unusual peptide-6-TGDP adduct; TC$^{20}$LLIVFSK-6-TGDP (FIG. 6). Supporting the experiment, the peptide-6-TGDP adduct also was detected in the in vitro sample of the RhoC 6-TGNP complex digested with trypsin, but not from the RhoC C20S mutant in the complex with 6-TGDP (not shown). The results suggest that the 6-TGNP, derived from 6-TG (or its analogs), binds to RhoC and/or covalently links to the redox-active RhoC Cys$^{20}$ side chain.

In view of structural considerations (Ihara et al. *J. Biol. Chem.* 273, 9656-9666 (1998); Dias et al. *Biochemistry* 46, 6547-6558 (2007)) associated with a previous study (Heo et al. *Biochemistry* 45, 14481-14489 (2006)) and the detection of the peptide-6-TGTP chimeric adduct (FIG. 6), a molecular mechanism is proposed that accounts for the 6-TGNP-mediated RhoC inactivation which leads to loss of invasive cell mobility (FIG. 7): (i) 6-TGTP, derived from 6-TG, binds to the RhoC GTP binding site, (ii) a redox agent (i.e., .$NO_2$) reacts with the RhoC Cys$^{20}$ side chain to produce a RhoC-Cys$^{20}$ thiyl radical. This thiyl radical then further reacts with the thiolate moiety of the bound 6-TGNP to produce a RhoC disulfide anionic radical (6-TGNP-RhoC Cys$^{20}$$^{\cdot-}$). The protein disulfide anionic radical can be quenched by a cellular molecule (i.e., glutathione or ascorbic acid) to produce a 6-TGNP-RhoC Cys$^{20}$; (iii) although the γ phosphate moiety of the chemically linked 6-TGTP can be hydrolyzed into 6-TGDP by Rho GAPs, it cannot be released from the RhoC by the action of a Rho GEF (e.g., Dbs) because of its disulfide linkage to RhoC. This linkage halts the Rho GEF Dbs-mediated GTP/GDP cycle, thereby terminating RhoC-dependent cell motility. The mechanism provides an explanation for the 6-TG-induced decline of cell invasiveness associated with RhoC in the presence of a redox agent.

The combined actions of 6-TG and a redox agent have been shown to be very effective for cellular RhoC inactivation (FIG. 5). Notably, a certain type of IBC is caused by the overexpression of RhoC (van Golen et al. *Clin. Cancer. Res.* 5, 2511-2519 (1999); Clark et al. *Nature* 406, 532-535 (2000). Hence, by mass action, a sequential treatment with 6-TG and a redox agent can target cellularly populated RhoC to inactivate RhoC, which ends invasive cell mobility and terminates the propagation of invasive tumors.

Figure 7:
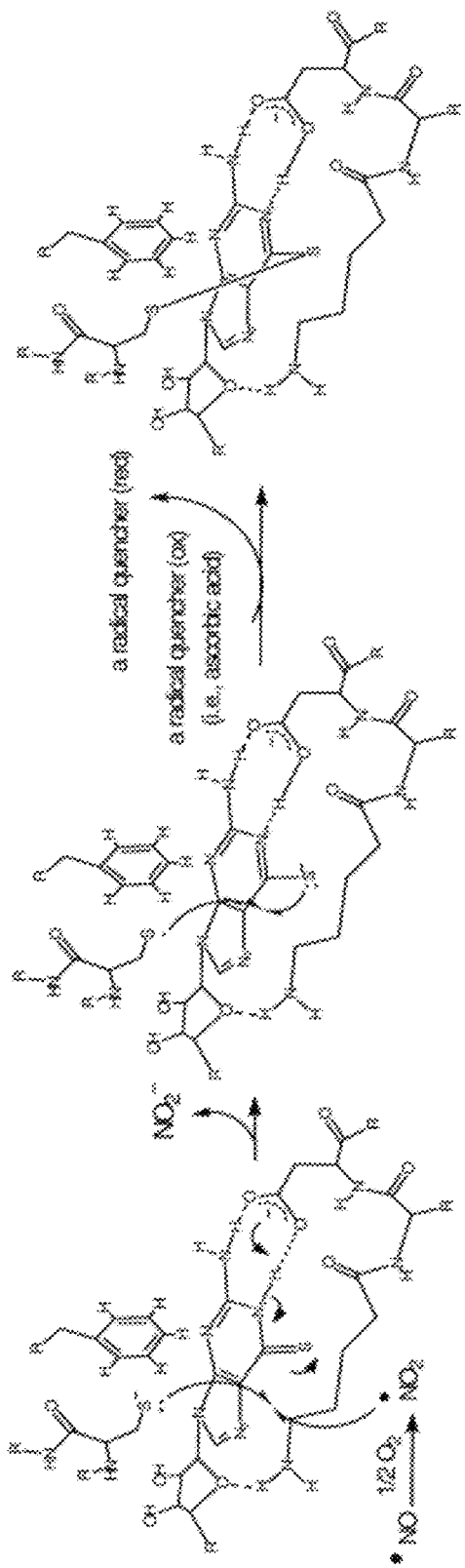
FIG. 7. Proposed mechanisms of the Rho 6-TGNP disulfide adduction formation. 6-TGNP is represented in blue. The dotted lines in black represent putative hydrogen-bond interactions between RhoC residues and 6-TGNP.

Although the molecular mechanism shown in FIG. 7 explains the action of 6-TGNP that targets one of the Rho GTPases, RhoC, the mechanism also is applicable to other GTPases having a redox-active cysteine in their nucleotide-binding GXXXXGK(S/T)C (SEQ ID NO:1) motif. For example, because Rac1 has the GXXXXGK(S/T)C motif, 6-TGNP derived from 6-TG is expected to target Rac1 to produce a 6-TGNP-Rac1 disulfide adduct. Recent in vitro kinetic results show that in the presence of a redox agent, 6-TGNP reacts with Rac1 $Cys^{18}$ (equivalent to RhoC $Cys^{20}$) to produce a 6-TGNP-Rac1 disulfide adduct (not shown). Moreover, other studies conducted without adding a redox agent suggest that 6-TGNP, coupled with the action of Vav, can specifically target Rac1, and result in relatively more inactivation of Rac1 than of other Rho proteins (Tiede et al. *J. Clin. Invest.* 111, 1133-1145 (2003); Poppe et al. *J. Immunol.* 176, 640-651 (2006)). However, as stated, these studies did not consider the action of a redox agent on the 6-TGNP-mediated inactivation of Rho GTPases.

Actions of 6-thioguanine on Ras.

Human bladder carcinoma (T24) and fibrosarcoma (HT1080) cells owe their cancerous properties, respectively, to the constitutively activated H-Ras G12V and N-Ras Q61K (Reddy et al. *Nature* 300, 149-152 (1982); Brown et al. *EMBO J.* 3, 1321-1326 (1984)); these T24 and HT1080 cells were used to examine the effect of 6-TG and/or a redox agent on Ras. Cell viability was examined employing 3-(4,5-dimethylthiazol-2-yl)-2,5-diphenyl tetrazolium bromide (MTT) (Cabello et al. *Int. J. Oncol.* 23, 697-704 (2003)).

Figure 8:
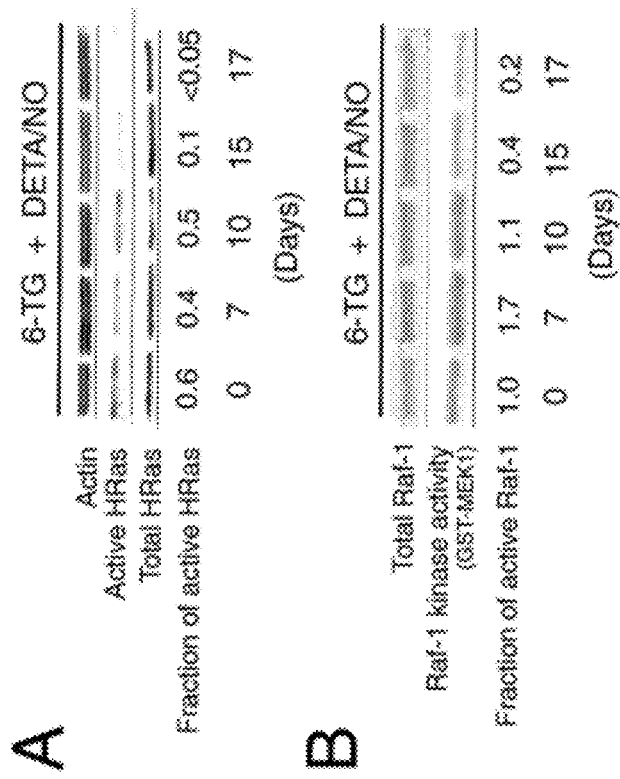
FIG. 8. Examination of Ras and Raf-1 activity in T24 cells treated with various reagents. (A) T24 cells were treated with 6-TG (1 μM, every 48 h) and DETA/NO (10 μM; every 8 h) for 17 days, and total Ras expression and its activity per cell mass was determined using an anti-HRas- and an anti-Raf-1-specific antibody, respectively, at the date indicated. (B) T24 cells were pretreated with 6-TG (1 μM; every 48 h) followed by treatment with DETA/NO (10 μM; every 8 h) for a day at the indicated date and analyzed for a Ras downstream effector Raf-1 activity using GST-MEK1 as a Raf-1 substrate. The total Raf-1 expression also was determined using an anti-Raf-1 antibody. Actin expression in cells was shown as controls.

As with HME-RhoC cells, when T24 or HT1080 cells were treated with 6-TG (1 μM), most cells underwent apoptosis, and thus the cell population drastically declined within a day (not shown). Similar to the situation with HME-RhoC, when cells were treated with 6-TG, ~20% of the initial cells resisted additional treatment with 6-TG and slowly regrew in the presence of 6-TG (not shown). When 6-TG-resisting T24 or HT1080 cells were continuously treated with both 6-TG (1 μM; every 48 h) and DETA/NO or GSNO (10 μM for every 20 and 8 h, respectively) for longer than ~10 days, a decrease in the viability of 6-TG-resisting cells was observed. The decrease in viability of T24 (or HT1080) cells was likely caused by the inactivation of Ras, because a significant amount of Ras (per cell mass) was inactivated by the 6-TG treatment (1 μM; every 48 h) and DETA/NO (10 μM; every 20 h) for longer than 10 days (FIG. 8).

Figure 9:
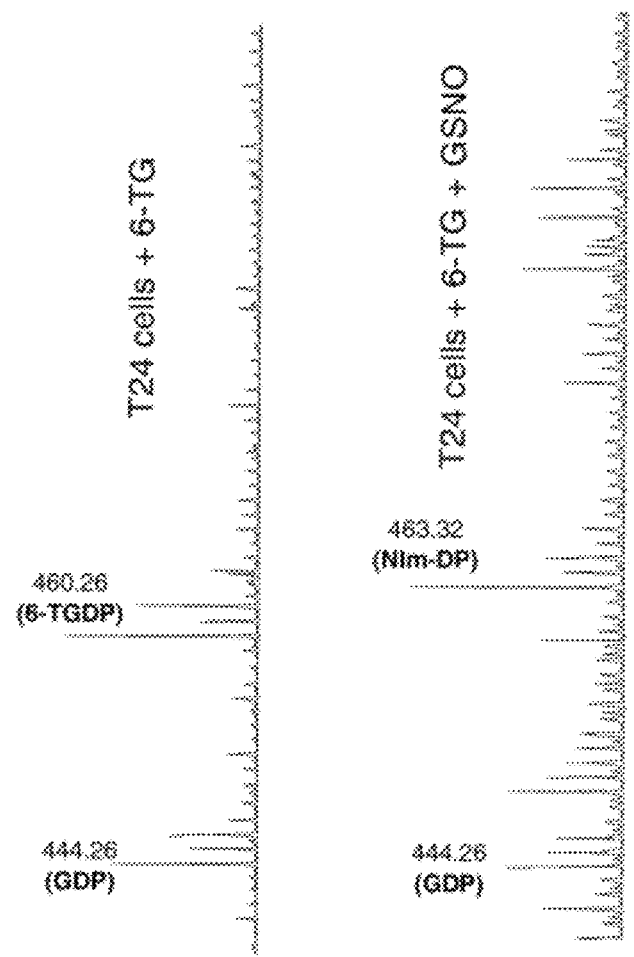
FIG. 9. Molecular weight determination of the .$NO_2$-mediated Ras-bound 6-TGNP dissociation product by ESI. As noted elsewhere, T24 cells possess oncogenic Ras G12V. Before treating the tumor cells with GSNO (10 μM; every 8 h) or DETA/NO (10 μM; every 20 h), cells treated with 6-TG (1 μM; every 48 h) for 8 days were washed twice in phosphate-buffered saline. A monoclonal antibody for Ras (Sigma) and a "Mammalian Co-Immunoprecipitation Kit" (Pierce) were used for the analyses of the Ras GTPase in T24 cells. The immunoprecipitated Ras sample was suspended in 50% methanol:0.1% formic acid. The protein portion and Ras-released nucleotide were separated by a brief centrifugation (3000×g for 5 min). To determine whether the T24 cell Ras releases chemically modified nucleotide(s), the supernatant containing Ras-released nucleotide(s) from the immunoprecipitated Ras sample was analyzed by ESI-MS.

An Electrospray Mass Spectrometry (ESI-MS) analysis shows that a detectable amount of 6-TGNP bound to Ras in T24 or HT1080 cells was observed after ~8-10 days from the initial treatment with 6-TG (FIG. 9). In the presence of both 6-TG (1 μM; every 48 h) and DETA/NO (2 μM; every 20 h) or GSNO (10 μM; every 8 h), 6-TGNP was barely detectable, but a 463.3 Dalton peak, which is assigned to 5-guanidino-4-nitroimidazole diphosphate (NIm-DP), was clearly present (FIG. 9). NIm-DP was probed only with inactivated Ras, suggesting that formation of NIm-DP couples with Ras inactivation in these cells (FIG. 8). Notably, NIm-DP is identified as a product of the degradation of the GDP-$NO_2$ adduct, which is released from Ras upon treatment with .$NO_2$ (Heo et al. *J. Mol. Biol.* 346, 1423-1440 (2005)).

Figure 3:
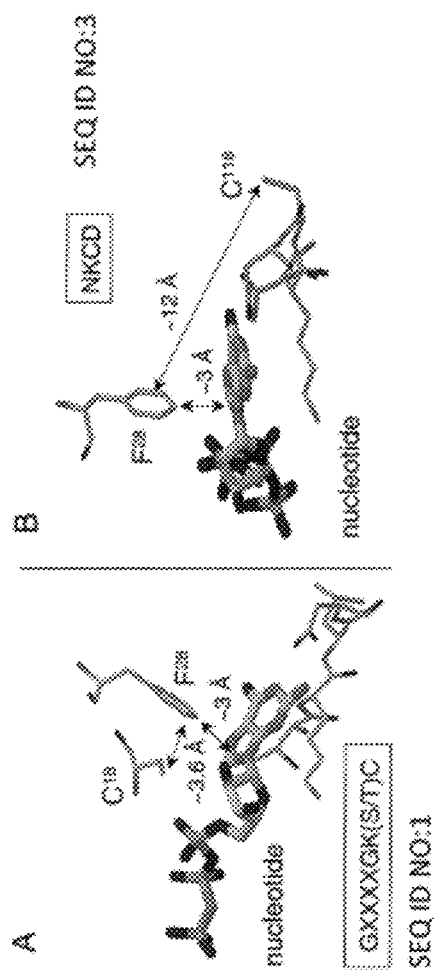
FIG. 3. Spatial architecture of the $Phe^{28}$ side chain and the redox-sensitive motif of GTPases with the bound nucleotide. The redox-active Rho family GTPases possess the GXXXXGK(S/T)C motif (SEQ ID NO:1) (A) instead of the $\overline{NKCD}$ (SEQ ID $\overline{NO}$:3) motif that is found in the redox-active Ras family GTPases (B). The distance and spatial orientation of the $Phe^{28}$ side chain, nucleotide ligand, and redox-active thiol group in the GXXXXGK(S/T)C (SEQ ID NO:1) motif of Rac1 (A) and the NKCD motif of $\overline{Rap}$1A (B) are presented. The Figure was generated by using RASMOL with PDB 1MH1 for the GXXXXGK(S/T)C (SEQ ID NO:1) motif-containing Rac1 GTPase and PDB $\overline{1C1Y}$ for the NKCD (SEQ ID NO:3) motif-containing Rap1A GTPase.

Although T24 or HT1080 cells produce Ras bound NIm-DP in the presence of 6-TG and a redox agent, a 6-TGNP-Ras disulfide adduct was not detectable in these tumor cells. It is believed that this is because, unlike with the GXXXXGK(S/T)C (SEQ ID NO:1) motif-containing Rho proteins such as RhoC, Rac 1, and Cdc42, the 6-TGNP target site of the NKCD (SEQ ID NO:3) motif-containing Ras GTPases is remote from the Ras nucleotide-binding site (See FIGS. 2 and 3) (Nassar et al. *Nature* 375, 554-560 (1995); Dumas et al. *Structure* 7, 413-423 (1999); Pai et al. *Nature* 341, 209-214 (1989); Brunger et al. *Proc. Natl. Acad. Sci. U.S.A.* 87, 4849-4853 (1990); Kraulis et al. *Biochemistry* 33, 3515-3531 (1994); Tong et al. *J. Mol. Biol.* 217, 503-516 (1991); Ito et al. *Biochemistry* 36, 9109-9119 (1997); Scheidig et al. *Structure* 7, 1311-1324 (1999)).

Figure 10:
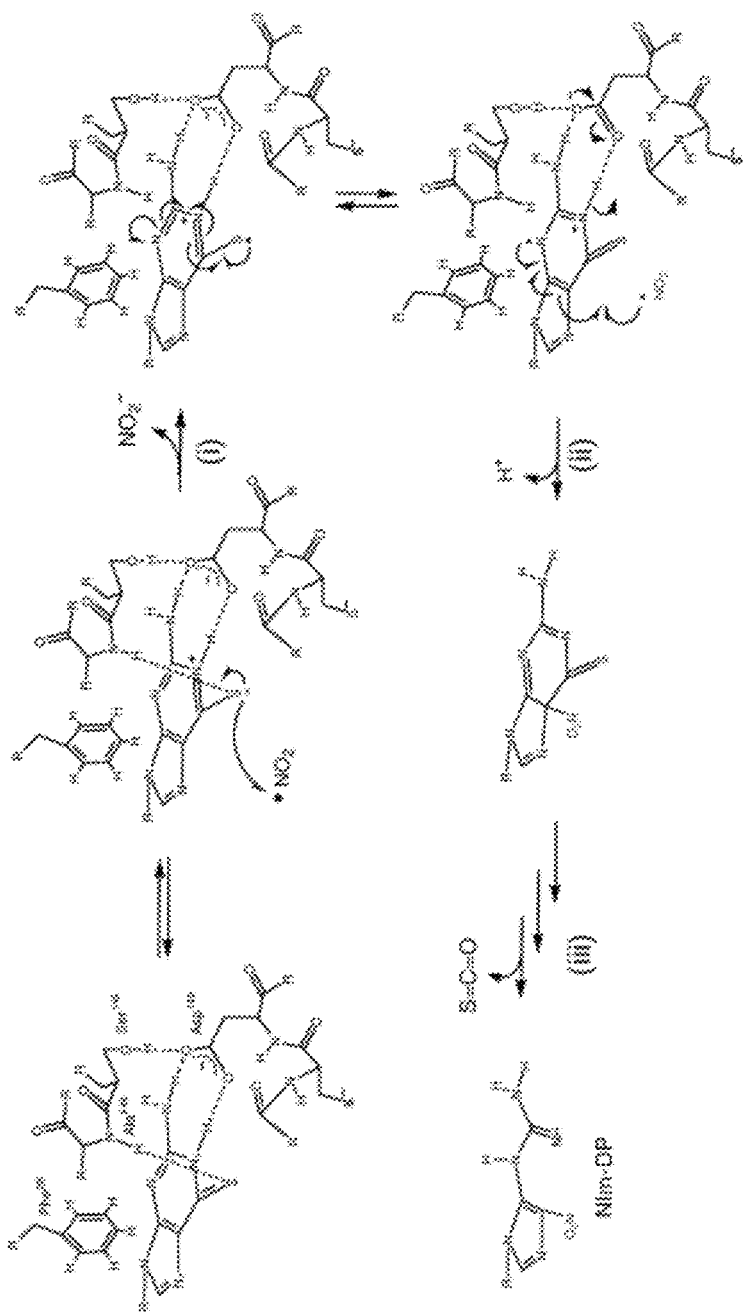
FIG. 10. Proposed mechanism of redox agent-mediated Ras 6-TGNP dissociation. 6-TGNP is represented in blue, and the $NO_2$ moiety of the nucleotide-nitration adduct is shown in red. The ribose phosphate moiety of 6-TGNP is depicted by R. The dotted lines in black represent putative hydrogen-bond interactions between Ras residues and 6-TGNP.

Given that .$NO_2$ can oxidize the sulfur atom of thiolate to produce a thiyl radical, .$NO_2$ may react directly with the sulfur atom of the Ras-bound 6-TGNP to produce a 6-TGNP-thiyl radical (FIG. 10). .$NO_2$ can also target the redox-sensitive Ras $Cys^{118}$ side chain if the sulfur site is available. The Ras $Cys^{118}$ side chain thiyl radical that is formed can produce the 6-TGNP-thiyl radical via the $Phe^{28}$ side chain as suggested in a previous study (Heo et al. *J. Mol. Biol.* 346, 1423-1440 (2005)). Importantly, the 6-TGNP-thiyl radical is equivalent to the oxygen radical in the radical-based Ras GNP dissociation mechanism (FIG. 10). Hence, the 6-TGNP-thiyl radical likely proceeds to perturb the Ras-binding interactions with 6-TGNP and then reacts with another .$NO_2$, resulting in the release of chemically modified 6-TGNP, 6-TGNP-$NO_2$ (FIG. 10). If so, the unstable 6-TGNP-$NO_2$ is degraded into NIm-DP by release of a carbon dioxide sulfide (O=C=S) (FIG. 10). As shown in FIG. 10, the mechanism of NIm-DP formation from the 6-TGNP-$NO_2$ adduct is likely similar to the decarboxylation of GNP-$NO_2$ to produce NIm-DP (Heo et al. *J. Mol. Biol.* 346, 1423-1440 (2005)).

In accounting for the proposed mechanism (FIG. 10), the equilibrium between the cellular 6-TGNP and the 6-TGNP-bound Ras also can be enhanced by .$NO_2$. However, how .$NO_2$ inactivates the 6-TGNP-bound Ras is less clear. Enhancement of the equilibrium between the cellularly free 6-TGNP and the oncogenic Ras-bound 6-TGNP cannot serve to inactivate Ras unless the cellular ratio of 6-TGTP/6-TGDP is <1. Another possibility is that a redox agent (i.e., .$NO_2$) and Ras downstream effector proteins compete for the 6-TGTP-bound Ras. Therefore, somehow the presence of a redox agent serves to reduce some amount of the mechanically stable state of oncogenic Ras that is bound with 6-TGTP and is capable of interacting with its downstream effector proteins.

Cytotoxic effects associated with chronic exposure to 6-TG and its analog drugs are all but inevitable. The 6-TG cytotoxicities associated with the DNA-targeting 6-TdGNP are well-known (Karran, P. *Br. Med. Bull.* 79-80, 153-170 (2006); O'Donovan et al. *Science* 309, 1871-1874 (2005); Hsieh et al. *Mech. Ageing Dev.* 129, 391-407 (2008); Casorelli et al. *Anticancer Agents Med. Chem.* 8, 368-380 (2008); Daehn et al. *Cancer Res.* 69, 2393-2399 (2009)). This study is the first to demonstrate that an accumulation of 6-TGNP over the course of long-term treatment with 6-TG can interfere, in the presence of a redox agent, with cellular protein Ras GTPases. Given that Ras plays a key role in cell signaling events, deregulation and/or misregulation of Ras is detrimental and thus cytotoxic to cells.

Small GTPase-Targeting Action of 8-Thioguanine.

To develop a better agent that targets the GXXXXGK(S/T)C (SEQ ID NO:1) motif of Rho proteins, we have screened the effects of various thiopurine analogs on the invasive cell mobility of HME-RhoC cells. The following is a list of those analogs screened: 8-thioguanine (2-amino-8-mercapto-1H-purin-6(9H)-one), 8-methylthioguanine (2-amino-8-(mercaptomethyl)-1H-purin-6(9H)-one), 7-methylthioguanine (2-amino-7-(mercaptomethyl)-8,9-dihydro-1H-purin-6(H)-one), and 7-thioguanine (2-amino-7-mercapto-8,9-dihydro-1H-purin-6(H)-one). [7- and 8-thioguanines are commercially available. Other analogs were obtained from Azopharma Drug Development Services, Miramar, Fla.] Of these several thiopurine analogs screened, 8-thioguanine (8-TG) most effectively inhibits the invasive cell mobility of HME-RhoC cells in the presence of a NO donor DETA/NO (see details below).

1. RhoC and 8-thioguanine.

On the basis of screening results associated with the inhibitory action of 8-TG on the invasive cell mobility of HME-RhoC cells, the detailed cellular effect of 8-TG on HME-RhoC cells in the presence and absence of a redox agent was further analyzed.

(a) Effects of 8-TG and/or a Redox Agent on HME-RhoC Cells.

Figure 11:
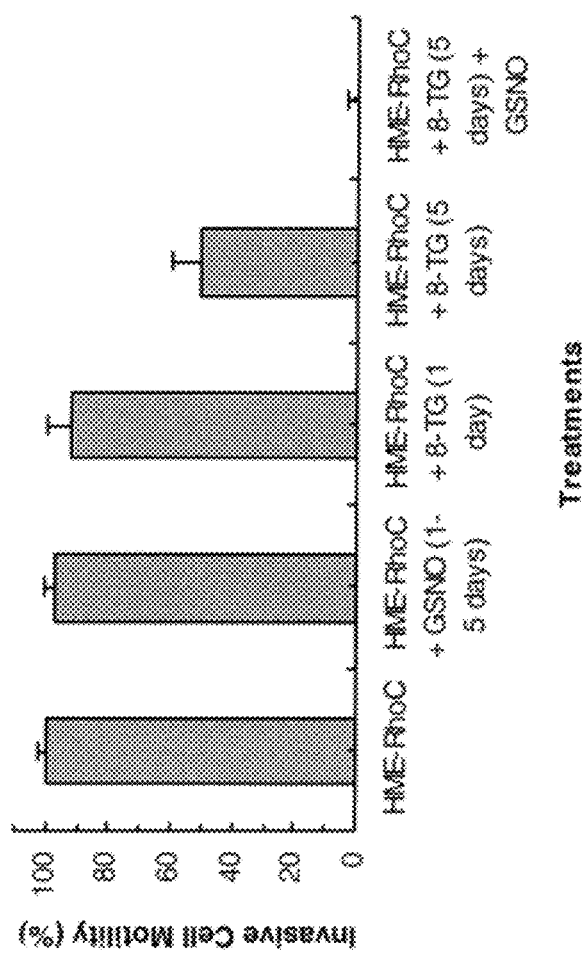
FIG. 11. Determination of cell invasiveness in the presence and absence of 8-thiopurine and/or a redox agent. The invasion motility assay for HME-RhoC cells was performed as described essentially in FIG. 5, except that 8-TG, instead of 6-TG, was used. The number of cells that had invaded the serum-free medium-containing lower chambers was used as a control background. Results are given as percent invasion over that seen in HME-RhoC cells (100%) and represent mean and standard error values from triplicate measurements.

The invasive cell mobility of HME-RhoC cells declined (~10%) within a day after treatment with only 8-TG (1 µM) (FIG. 11). The invasive cell mobility of HME-RhoC cells further declined (~60%) over the course of 5 days of continuous treatment with only 8-TG (1 µM) (FIG. 11). However, unlike with 6-TG, the apoptotic effect of 8-TG on HME-RhoC cells was minimal because less than 5% of HME-RhoC cells treated with 8-TG (1 µM) underwent apoptosis within a day. A delayed minor apoptosis (~5%) was observed in HME-RhoC cells over the course of a week of treatment with 8-TG (1 µM).

When HME-RhoC cells were treated with 8-TG for a week, followed by treatment with an NO donor (DETA/NO or GSNO; 10 µM for every 20 or 8 h, respectively), virtually all of the invasive mobility of HME-RhoC cells was immediately terminated. Intriguingly, despite termination of cell invasiveness, the viability of the HME-RhoC cells treated with an 8-TG-redox agent was almost the same as that of the untreated HME-RhoC cells.

(b) Potential Mechanistic Action of 8-TG and a Redox Agent on the Termination of Cell Mobility of HME-RhoC Cells.

Figure 12:
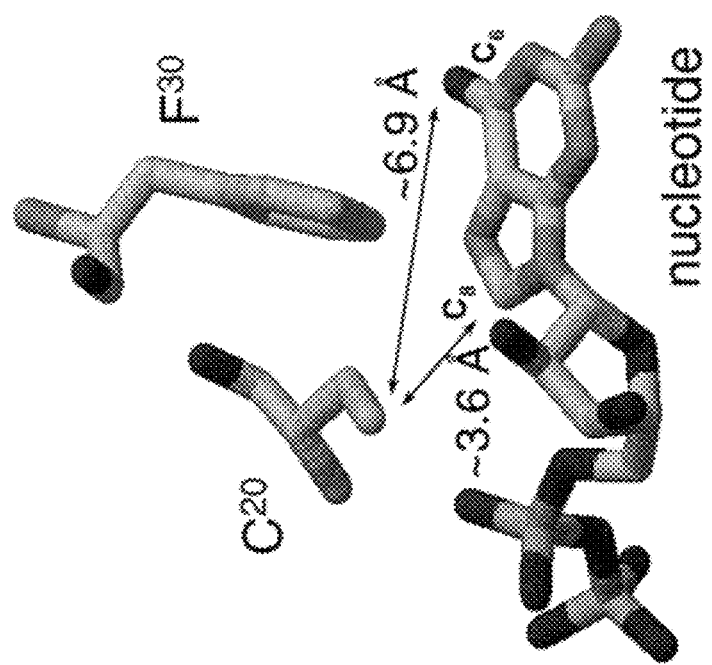
FIG. 12. Spatial architecture of RhoC with the bound nucleotide. The distance and spatial orientation of the $Phe^{30}$ side chain, nucleotide ligand, and the redox-sensitive thiolate group in the GXXXXGK(S/T)C (SEQ ID NO:1) motif of RhoC are shown. The distance between the sulfur atom of the $Cys^{20}$ side chain and the C8 carbon of GDP is estimated to be ~3.6 Å. The distance between the sulfur atom of the $Cys^{20}$ side chain and the sulfur atom of 8-TG base is shown to be ~6.9 Å. Finally, the distance between the sulfur atom of the $Cys^{20}$ side chain and the sulfur atom of 8-TG base is calculated to be ~2.1 Å. The figure was generated by using RAS-MOL with PDB 1GCO.

The structural feature of the nucleotide-binding pocket of RhoC (PDB 1GCO) in conjunction with the proposed molecular mechanism for RhoC (FIG. 7) explains the inhibitory action of 8-TG on the invasive cell mobility of HME-RhoC cells, where the distance between the sulfur atom of the RhoC $Cys^{20}$ side chain and the sulfur atom at the $C_8$ position of base (~2.1 Å; c.f., a direct distance between the RhoC $Cys^{20}$ sulfur atom and the $C_8$ carbon is ~3.6 Å) is shorter than that of the sulfur atom of the RhoC $Cys^{20}$ side chain and the sulfur atom at the $C_6$ position of base (~6.9 Å) (FIG. 12). The putative distance between the sulfur atom of the RhoC $Cys^{20}$ side chain and the sulfur atom at the $C_8$ position of the base (~2.1 Å) is optimal for a disulfide bond distance. In addition, in silico analysis using MM2 and MOPAC energy minimizations performed by 3D Chem (Cambridge software) suggests that the disulfide bonding torsion constraint between the sulfur atom of the RhoC $Cys^{20}$ side chain and the sulfur atom at the $C_8$ position of the base is less than the disulfide bonding torsion constraint between the sulfur atom of the RhoC $Cys^{20}$ side chain and the sulfur atom at the $C_6$ position of 6-TG base.

(c) Implication of the Action of 8-TG and a Redox Agent on Cells Overexpressing RhoC.

These results indicate that the effect of 8-TG in conjunction with a redox agent for the termination of the RhoC-mediated cell invasiveness of HME-RhoC cells was much more effective than a 6-TG-redox combination in terminating the RhoC-mediated cell invasiveness of HME-RhoC cells.

2. Ras and 8-thioguanine.

The cancerous property of T24 and HT1080 cells is because of the presence of constitutively active Ras (Li et al. *Br. J. Cancer.* 92, 80-88 (2005); Rait et al. *Bioconjug. Chem.* 11, 153-160 (2000); Chen et al. *J. Biol. Chem.* 271, 28259-28265 (1996); Liu et al. *Anticancer Res.* 17, 1107-1114 (1997); Plattner et al. *Proc. Natl. Acad. Sci. U.S.A.* 93, 6665-6670 (1996); Gupta et al. *Mol. Cell. Biol.* 21, 5846-5856 (2001)). Hence, as with 6-TG (FIGS. 8 and 9), if 8-TG targets and perturbs Ras GTPase, the cancerous growth of these tumor cells will be altered. However, 8-TG (1 µM) in combination with an NO donor (DETA/NO or GSNO; 10 µM for every 20 or 8 h, respectively) did not affect viability and anchorage-independent growth of T24 and HT1080 cells (not shown). The expression and activity of Ras in these cells also were virtually unchanged (not shown). These results indicate that, unlike with 6-TG, the cytotoxic effect of 8-TG with a redox agent associated with Ras is minimal. Therefore, 8-TG together with a redox agent may not be able to perturb Ras activity in these cells.

Example 2

Examination of the Biochemical Effects of 6-TGNP or 8-TGNP on RhoC GTPase in the Presence and Absence of a Redox Agent and/or Dbs Kinetic Assays on the Role of a Redox Agent in the Formation of a Disulfide Bond Between 6- or 8-TGNP and a RhoC Protein:

To explore the effect and molecular mechanism of the formation of the 6- or 8-TGNP-RhoC adduct via the formation of a 6- or 8-TGNP RhoC disulfide on the RhoC GNE, kinetic analyses were performed.

Figure 13:
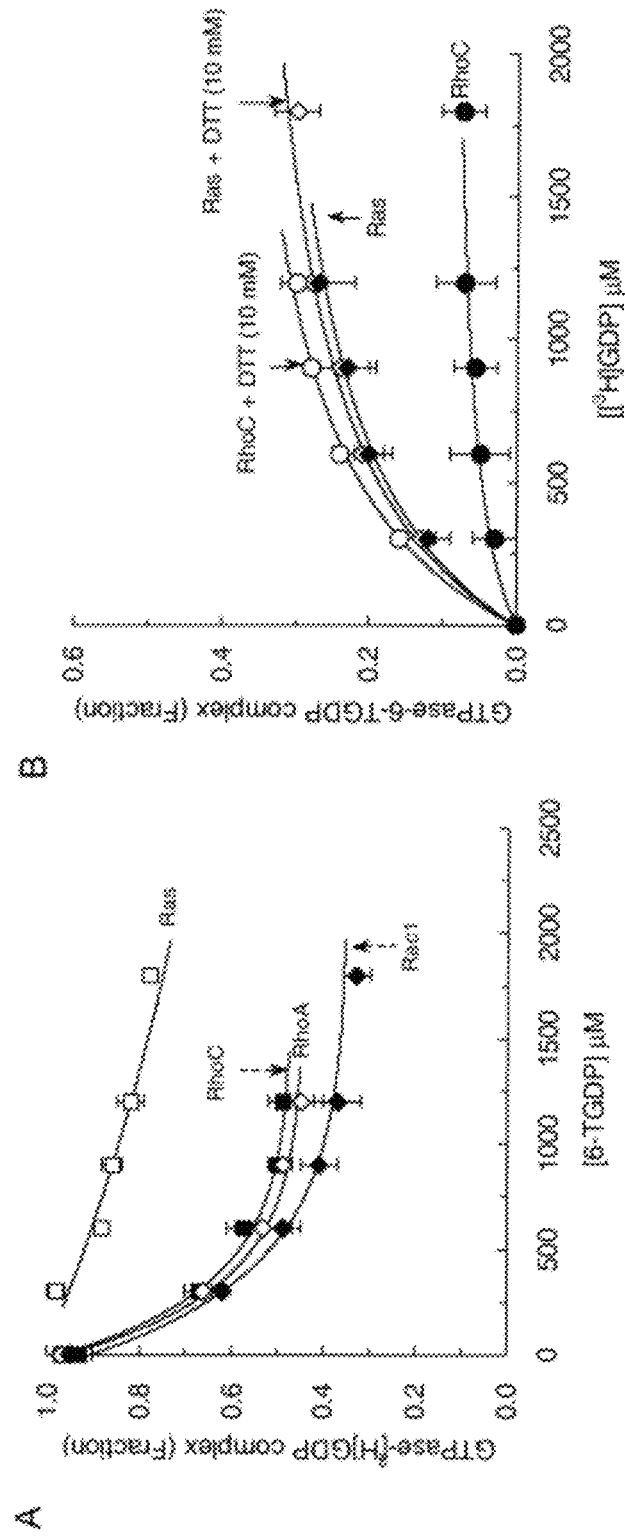
FIG. 13. Guanine nucleotide exchange of small GTPases with 6-TGDP. (A) To monitor 6-TGDP-mediated GTPase GDP dissociation, [$^3$H]GDP-loaded GTPase (1 μM) was incubated with 6-TGDP (0-2000 μM) for 1 h. (B) To monitor GTPase 6-TGDP dissociation by GDP (0-2000 μM) in the presence and absence of dithiothreitol (DTT), 6-TGDP-loaded GTPase (~1 μM) was treated with .$NO_2$ (~3 μM) under anaerobic conditions and was incubated with various concentrations of [$^3$H]GDP (0-2000 μM) in the presence and absence of DTT (10 mM) for 1 h. For all assays, aliquots were withdrawn and spotted onto nitrocellulose filters. The filters were then washed three times with an assay buffer, and radioactivity was determined using a Beckman-Coulter scintillation counter. The resultant radioactivity (dpm) values associated with GTPase-bound [$^3$H]GDP were converted into the fraction of mol nucleotide per mol total GTPase. The data presented represent mean and standard error values from triplicate measurements. The apparent dissociation constants (appKD values) of GTPase 6-TGDP association ([$^3$H]GDP dissociation, A); and 6-TGDP dissociation ([3H]GDP association, B) were obtained by fitting the data to a simple dissociation and association, respectively. (A) The $^{app}KD$ values of Ras, RhoC, RhoA and Rac1 for 6-TGDP, are, respectively, 2300, 230, 224, and 245 μM [6-TGDP]. (B) The appKD values of RhoC with and without DTT are, respectively, 560, and 1000 μM [[$^3$H]GDP], whereas the $^{app}KD$ values of Ras with and without DTT are 530, and 520 μM [[$^3$H]GDP], respectively. The standard errors of each $^{app}KD$ value are less than 10% of their given values, and regression values associated with the fit were $r^2 > 0.9560$.

A kinetic assay method using radiolabeled GDP ([$^3$H]GDP) was established. The apparent dissociation constants ($^{app}K_{D\ 6\text{-}TGDP}$) of Rho GTPases (including RhoA, Cdc42, and Rac1/2/3) and Ras with 6-TGDP were determined (FIG. 13). The results of this preliminary kinetic study provided strong support for the mechanism proposed for the role of 6-TGNP in RhoC inactivation (FIG. 7).

Studies show that binding interactions between Rho GTPases and 6-TGNP were weaker than binding interactions between Ras and 6-TGNP (Tiede et al. *J. Clin. Invest.* 111, 1133-1145 (2003); Poppe et al. *J. Immunol.* 176, 640-651 (2006)) although an $^{app}K_{D\ 6\text{-}TGDP}$ value of RhoC was not determined in these studies. FIG. 13 shows that the $^{app}K_{D\ 6\text{-}TGDP}$ of RhoC [$^3$H]GDP with 6-TGDP is similar to that of RhoA but much smaller than that of Ras. The true dissociation constant ($^{true}K_{D\ 6\text{-}TGDP}$) of Ras, RhoC, RhoA and Rac1 for 6-TGDP was then calculated to be ~20.7 pM, 212 µM, 208 µM, and 158 µM [6-TGDP] by using a compensation equation, $^{true}K_{D\ 6\text{-}TGDP} = {}^{app}K_{D\ 6\text{-}TGDP}/(1+[GDP]/{}^{true}K_{D\ GDP})$ (95), in conjunction with the values given [($^{app}K_{D\ 6\text{-}TGDP}$ of Ras, RhoC, RhoA, and Rac1=2300, 230, 224, and 245 µM (FIG. 13) and $^{true}K_{D\ GDP}$=9 pM, 12 µM, 13

μM and 1.8 μM, respectively. The $^{true}K_{D\ GDP}$ of Ras, RhoA and Rac1 was determined previously (Lenzen et al. *Biochemistry* 37, 7420-7430 (1998); Heo et al. *Biochemistry* 44, 6573-6585 (2005)) and the $^{true}K_{D\ GDP}$ of RhoC was further determined. Example: $^{true}K_{D\ 6\text{-}TGDP}$ for Ras=2300 μM/(1+1 μM GDP/~9 μM)=−20.7 μM [6-TGDP]]. The results suggest that the binding interaction of Rho GTPases with 6-TGDP is ~15-fold weaker than with GDP.

FIG. 13B shows that the $^{app}K_D$ of RhoC 6-TGDP with [$^3$H]GDP in the absence of DTT was much larger than that of RhoC with GDP in the presence DTT. The $^{app}K_{D\ [3H]GDP}$ was converted into $^{true}K_{D\ [3H]GDP}$ by using a compensation equation, $^{true}K_{D\ [3H]GDP}=^{app}K_{D\ [3H]GDP}/(1+[6\text{-}TGDP]/^{true}K_{D\ GDP})$ (Segel, I. H. (1993) *Enzyme kinetics*, A Wiley-Interscience publication, New York) (see above)). The calculated $^{true}K_{D\ [3H]GDP}$ values of RhoC in the presence and absence of DTT were estimated to be 516 μM and 923 μM, respectively. However, the $^{app}K_{D\ [3H]GDP}$ values of Ras in the presence and absence of DTT were not significantly changed when they were converted into $^{true}K_{D\ [3H]GDP}$ values ($^{true}K_{D\ [3H]GDP}$ values of Ras=4.7 and 4.8 nM, respectively). Unlike with Ras, such a large $^{true}K_{D\ [3H]GDP}$ value of RhoC estimated in FIG. 13B (923 μM) in the absence of DTT suggests that [$^3$H]GDP cannot compete with the RhoC bound 6-TGDP. The smaller $^{true}K_{D\ [3H]GDP}$ value of RhoC in the presence of DTT suggests that [$^3$H]GDP was able to drive out 6-TGNP from RhoC in the presence of DTT. One possible explanation for these results is that the chemical modification of RhoC with 6-TGDP to produce the 6-TGNP-RhoC adduct blocks release of 6-TGDP from RhoC (see FIG. 7). Treatment with DTT, a reducing agent, disrupts the disulfide bond between RhoC and 6-TGDP, liberating 6-TGDP from RhoC, and thereby permitting [$^3$H]GDP to bind to RhoC.

Example 3

Insight into the Termination of the Invasive Motility of Tumor Cells Derived from Inflammatory Breast Cancer by 6-Thiopurines Cell Culture and Treatments.

SUM cells were cultured according to the cell culture protocol provided by the vendor (Asterand, Detroit Mich.). Transfection of human mammary epithelial cells with wild type RhoC and mutant C20S RhoC to produce HME-RhoC and HME-C20S RhoC, respectively, as well as culturing of these HME-RhoC and HME-C20S RhoC cells were performed according to known procedures (van Golen et al., *Mol. Cancer Ther.* 1, 575-583 (2002)). Human colon adenocarcinoma (cell-line, SW480) and hepatocellular carcinoma (cell-line, HCCLM3) cells were cultured according to the cell culture protocol provided by the vendor (American Type Culture Collection, Manassas, Va.). Cells were treated with 6-TG (1 μM) and/or a NO-releasing agent diethylenetriamine/nitric oxide (DETA/NO) (10 μM) or S-nitrosoglutathione (GSNO) (10 μM) at every ~24 and/or ~20 or ~8 h, respectively, for three days to maintain a minimal 50% of the initial concentration of NO in the culture media (Heo et al., *Biochemistry* 49, 3965-3976 (2010)). The treatment time interval for 6-TG is based on empirical reasoning that three consecutive treatments with 6-TG for up to four days will not result in an overdose of 6-TG, but will ensure that the level of 6-TG is higher than 1 μM in the culture media. The established cell treatment time interval for DETA/NO or GSNO is because the half-life of DETA/NO and GSNO is ~20 and ~8 h, respectively, at pH 7.4 and 37° C. (Maragos et al. *J. Med. Chem.* 34, 3242-3247 (1991); Mooradian et al. *J. Cardiovasc. Pharmacol.* 25, 674-678 (1995); and Floryszak-Wieczorek et al. *Planta* 224, 1363-1372 (2006)).

Cell Motility Assay.

An invasion assay using Matrigel (BD Biosciences, Bedford Mass.), performed as described previously except for minor modification (van Golen et al. *Clin. Exp. Metastasis* 14, 95-106 (1996)), was the major method used in examining the effect of 6-TG and/or a redox agent on SUM149, HME-RhoC, or HME-C20S RhoC cells. The top chamber of a Transwell filter (6.5 mm with 8 μm pores, Costar; Corning, N.Y.) was coated with a 10 μL aliquot of 10 mg/mL Matrigel, and the lower chamber of the Transwell was filled with either serum-free or serum-containing media. Sample cells were prepared to resuspend cells in a serum-free medium with 0.1% BSA at a concentration of 4×10$^5$ cells/mL. The sample cells (0.5 mL) were added to the top chamber of a Transwell filter, overlaid with a solution (0.1 mL) containing 6-TG and/or DETA/NO or GSNO, and then incubated for three days at 37° C. in a 10% CO$_2$ incubator. When necessary, the top chamber was repeatedly overlaid with the solution (0.1 mL) containing 6-TG and/or DETA/NO or GSNO as indicated above. The Transwell filters were fixed with methanol, stained with haematoxylin and eosin, and cells in the serum-containing samples were counted. The number of cells that had invaded the serum-free, medium-containing lower chambers was used as a control background.

The Colorimetric-based QCM Cell Invasion Assay kit (Millipore, Billerica, Mass.) was used for the time-dependent cell migration assay of SUM149, SW480, and HCCLM3 cells. Serum-free sample cells (2×10$^5$ cells/mL) were prepared as indicated in the section of the matrigel invasion assay. The serum-free sample cells (0.25 mL) were loaded to the rehydrated upper chamber. The cell-containing upper chamber was then overlaid with a solution (0.05 mL) containing 6-TG and/or DETA/NO or GSNO. Serum-free or serum-containing media (0.5 mL) was added to the lower chamber. The plate covered was then incubated for one to four days at 37° C. in a 10% CO$_2$ incubator. Like with the matrigel invasion assay, the upper chamber was repeatedly overlaid with the solution (0.05 mL) containing 6-TG and/or DETA/NO to maintain the desired level of 6-TG and NO in the upper chamber. The fraction of cells migrated from the upper chamber to the lower chamber was then measured colorimetrically according to the procedure provided by the manufacture.

Clonogenic, Viability, and Apoptotic Assays.

When necessary, various other assays such as a soft agar-based clonogenic assay (Yamashita et al. Oncogene 18, 4777-4787 (1999); Ghatak et al. *J. Biol. Chem.* 277, 38013-38020 (2002)), a cell viability assay employing 3-(4,5-dimethylthiazol-2-yl)-2,5-diphenyl tetrazolium bromide (Vistica et al. *Cancer Res.* 51, 2515-2520 (1991); Sato et al. *Cancer Letters* 112, 181-189 (1997)), and an apoptosis assay using the ApoAlert Caspase-3/8 Colorimetric Assay Kit (Takara, Japan) also were performed to examine the effect of a NO donor and/or 6-TG on HME-RhoC or HME-C20S RhoC cells.

RhoC Activity Assay in Cells.

Cells were lysed in an extraction buffer containing 50 mM NaCl, 5 mM MgCl$_2$, 1 mM ethylenediaminetetraacetic acid (EDTA), 0.1 mM diethylenetriaminepentaacetic acid (DTPA), and 0.1% NP40 in 150 mM TrisHCl (pH 8.0). The content of active RhoC in cells then was determined by using Western analysis that relies on a monoclonal anti-RhoC antibody (Biocompare, South San Francisco, Calif.). To determine RhoC activity, the colorimetric RhoA activation assay Biochem Kit (Cytoskeleton, Denver, Colo.) was used essentially as described in the previous study (Hall et al. *Neoplasia*

10, 797-803 (2008)) except that the RhoC specific antibody (vide supra), instead of the RhoA antibody included in the assay kit, was used for this analysis.

Mass Spectrometric Analysis.

Cell lysates in an extraction buffer were incubated with a monoclonal anti-RhoC antibody precoupled to glutathione-agarose beads. The beads were collected by centrifugation and washed three times with the extraction buffer. RhoC proteins on beads were then eluted with a solution containing 50% methanol, 0.1% formic acid, 0.1 mM $MgCl_2$ 1 mM EDTA, and 0.1 mM DTPA. The protein portion and RhoC-released nucleotide were separated by brief centrifugation (3,000×g for 5 min). The protein portion from the immuno-precipitated RhoC was resuspended in a buffer containing 1 mM EDTA and 0.1 mM DTPA in 50 mM TrisHCl (pH 7.4), then digested with trypsin for 10 h, and analyzed with electrospray mass spectrometry (ESI-MS) and tandem mass spectrometry (MS/MS) in the positive ion mode ([molecular mass+H]$^+$).

Kinetic Assays.

Transition metal-free assay buffer and vials as described in a previous study (Heo et al. *Biochemistry* 49, 3965-3976 (2010)) were used for all kinetic assays. The kinetic assay buffer contains the highest grade of 50 mM NaCl, 10 mM $MgCl_2$, 1 mM EDTA, and 0.1 mM DTPA in 50 mM TrisHCl (pH 7.4). Before performance of any of the assays, all protein samples also were dialyzed with a metal-free buffer under anaerobic conditions. As with RhoA and Rac1 (Heo et al. *J. Biol. Chem.* 280, 31003-31010 (2005)), C20S RhoC were expressed in *E. coli* and purified using anionic and size exclusion columns.

(a) A competitive binding assay was performed to determine the binding affinity of Rho GTPase and 6-TGDP. The radiolabeled [$^3$H]GDP-loaded Rho protein (1 μM) was titrated with various concentrations of 6-TGDP. The titrated Rho protein sample then was spotted onto a nitrocellulose membrane. Each membrane was washed three times with the assay buffer, and radioactivity was determined using a Beckman-Coulter scintillation counter. The radioactivity of the sample (Rho protein-bound [$^3$H]GDP) was converted into, and thus plotted, as the fraction of mol GDP per mol total Rho protein. The apparent dissociation constant ($^{app}K_D$) of the Rho protein with [$^3$H]GDP in the presence of 6-TGDP was determined by using Prism software to fit the titration curve to a hyperbola.

(b) The effect of redox agents such as NO, .$NO_2$, and $N_2O_3$ on the binding interaction between RhoC proteins and GDP or 6-TGDP was examined under $N_2$-filled serum-stoppered anaerobic experimental conditions ($O_2$<3 ppm). These anaerobic experimental conditions were necessary to block the reaction of NO or .$NO_2$ with $O_2$ to produce higher oxides. The contents of NO and .$NO_2$, respectively, in the sealed assay vials were determined by using a hemoglobin assay and $NO_2^-/NO_3^-$ Assay Kit-C II (Dojindo) under anaerobic conditions (Heo et al. *J. Biol. Chem.* 280, 31003-31010 (2005); Heo et al. Biochemistry 43, 2314-2322 (2004)). $N_2O_3$ was generated by mixing NO and .$NO_2$ 1:1 stoichiometrically. However, because the $N_2O_3$ thus formed can be decomposed into NO and .$NO_2$, the content of $N_2O_3$ need not be at 100%. To examine the redox property of RhoC with GDP, the [$^3$H] GDP-loaded RhoC protein (1 μM) was treated with redox agents (~3 μM) in the presence of free GDP (10 μM). The fraction of the redox agent-mediated release of the bound [$^3$H]GDP per Rho protein over time was determined as noted above, and the result was plotted against time. The rates of RhoC GDP dissociation in the presence of redox agents were determined by using Prism software to fit the result to a one-phase exponential decay.

(c) To test the Rho 6-TGDP-binding interaction in the presence of redox agents, the 6-TGDP-loaded RhoC protein was treated with redox agents in the presence of free [$^3$H]6-TGDP (10 μM). An association of RhoC protein with [$^3$H] GDP to produce a RhoC-[$^3$H]GDP complex will occur proportionally after RhoC releases 6-TGDP through the action of redox agents. Therefore, the fraction of the redox agent-mediated release of the bound 6-TGDP per Rho protein over time can be deduced by determination of the RhoC-bound [$^3$H]GDP, where the quantity of RhoC-bound 6-TGDP equals 1 minus the determined fraction of the RhoC-bound [$^3$H]GDP as described in Section (b). The estimated data associated with the quantity of RhoC-bound 6-TGDP then was fitted to a one-phase exponential decay; Prism software was used to derive the rate of 6-TGDP dissociation from RhoC.

(d) The effect of .$NO_2$ on the dissociation of 6-TGDP from RhoC was determined by treating the RhoC-6-TGDP complex titration with various concentrations of [$^3$H]GDP in the presence and absence of a reducing agent of either dithiothreitol (DTT) or β-mercaptoethanol. The data were fitted to a hyperbola with Prism Software to estimate the $^{app}K_D$ of RhoC with 6-TGDP in the presence of [$^3$H]GDP.

Effects of Thiopurines on SUM and RhoC-Overexpressed HME Cells in the Presence and Absence of a Redox Agent.

SUM149 cells and HME-RhoC have exhibited an invasive cell motility (FIG. 14A). Unlike with SUM149 and HME-RhoC cells, SUM102 and HME cells that are not overexpressed with RhoC do not exhibit cell motility. The observed RhoC-dependent cell motility of these SUM149 and HME-RhoC cells is consistent with a previous study (van Golen et al. *Mol. Cancer. Ther.* 1, 575-583 (2002)). Unlike the action of 6-TG on fast growing tumor cells (Heo et al. Biochemistry 49, 3965-3976 (2010)), the apoptotic effect of 6-TG on SUM149 and HME-RhoC cells was minimally affected by treatment with 6-TG for 3 days (FIG. 25A). The apoptotic effect of 6-TG on SUM149 and HME-RhoC cells also was minimal (FIG. 25B). This result is similar to the effect of 6-TG on primary breast carcinoma in which treatment with 6-TG concentrations of less than ~2 μM for 3 days has minimal effect on the survival of primary breast carcinoma cells (Yamane et al. *Cancer Res.* 67, 6286-6292 (2007)).

However, continuous treatment of SUM149 and HME-RhoC cells with 6-TG for three or more consecutive days resulted in a gradual but significant diminution of cell motility (FIG. 14A). Despite the diminution of this activity, the level of total RhoC expression in these SUM149 and HME-RhoC cells was not changed (FIG. 14A). Because cell motility is coupled with the activity of RhoC but not the level of RhoA expression, this diminution of cell motility is likely correlated with the 6-TG-mediated deregulation of RhoC activity.

Invasive cell motility also can be achieved by an overexpression of the mutant RhoC C20S in HME (i.e., HME-C20S RhoC) cells (FIG. 14A). However, the effect of 6-TG on the motility of HME-C20S RhoC cells was insignificant compared with the effect of 6-TG on the motility of SUM149 and HME-RhoC cells (FIG. 14A). The activity of, and total expression of, RhoC C20S also were unchanged by the treatment of HME-C20S RhoC with 6-TG for three days (FIG. 14A). This result suggests the possibility that the RhoC residue Cys[20] somehow plays a role in the action of the 6-TG-mediated diminution of the motility of SUM149 and HME-RhoC cells.

Figure 25:
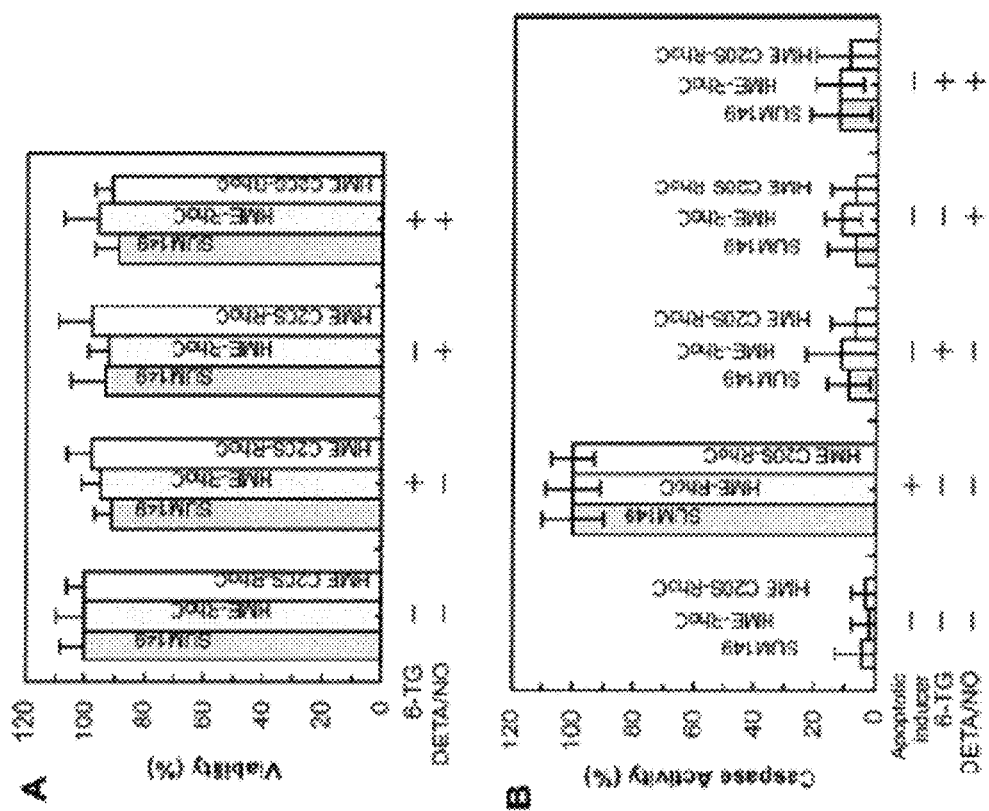
FIG. 25. Effect of 6-TG in combination with DETA/NO on the viability and caspase activity of cells. MTT and caspase assays for cells treated with 6-TG (1 µM at every 24 h) and/or DETA/NO (10 µM at every 20 h) were performed as described elsewhere herein. (A) MTT assay: for each cell line, the determined values of cell viability in the presence of 6-TG and/or DETA/NO were normalized against the mean value of cell viability in the absence of 6-TG and DETA/NO (set to be 100%). (B) Caspase-3/8 assay: the apoptotic activity of sample cells treated with the apoptotic inducer was set to be 100%, and other results were then expressed as normalized values against the mean value associated with the treatment with the apoptotic inducer. For both (A) and (B), all values represent the mean values and standard error values from triplicate measurements.

The cell viability and caspase activity of these SUM149, HMERhoC, and HME-C20S RhoC cells were minimally changed by treatment with the NO donor alone (FIG. 25). A minor effect of the NO donor DETA/NO on the viability of head and neck squamous cell carcinoma (cell-line HNSCC) was also observed; however, this effect may depend on the type of cell involved (Azizzadeh et al. *Laryngoscope* 111, 1896-1900 (2001)). The effect of three days of continuous treatment with a NO donor—DETA/NO or GSNO—on the invasive cell motility and RhoC activity of these SUM149, HME-RhoC or HME-C20S RhoC cells was minimal (FIG. 14A). The motility of both SUM149 and HME-RhoC cells treated with a NO donor DETA/NO or GSNO initially increased (10-30%) within 5 h, but after 10 h this enhanced motility declined slightly below the original level. This initial activation may be due to the redox response of RhoC because this protein possesses the GXXXXGK(S/T)C (SEQ ID NO:1) motif (Heo et al. *J. Biol. Chem.* 280, 31003-31010 (2005); Heo et al. *Biochemistry* 45, 14481-14489 (2006)).

This notation is supported because the cellular activity of C20S RhoC was unchanged after treatment of HME-C20S RhoC cells with a NO donor; the initial stimulatory effect of a NO donor on HME-C20S RhoC cells was not observed. Although the expression of RhoC was unchanged at the cellular level, essentially no RhoC activity was detected and complete termination of the invasive cell motility of SUM149 and HME-RhoC cells was observed when these cells were treated for three days with both 6-TG and DETA/NO (or GSNO) (FIG. 14A). The viability and caspase activity of SUM149 and HME-RhoC cells were minimally affected by treatment with 6-TG and DETA/NO (FIG. 25). This means that the 6-TG mediated termination of the invasive motility of these cells in the presence of the NO donor cannot be attributed to a change in the viability and/or induction of apoptosis of these cells by 6-TG and DETA/NO. Just as with the single treatment with 6-TG or a NO donor, the combined effect of 6-TG and a NO donor is likely linked to the redox-sensitive GXXXXGK(S/T)C (SEQ ID NO:1) motif of RhoC. This reflects the comparative lack of a significant effect of 6-TG with a NO donor on either the mutant C20S RhoC activity or the invasive cell motility of HME-C20S RhoC cells compared with the effect of either 6-TG or a NO donor alone on the C20S RhoC or on these same HME-C20S RhoC cells, respectively (FIG. 14A).

Like with SUM149 cells, most of the invasive motility of SW480 and HCCLM3 tumor cells associated with RhoC (Wang et al. *World J. Gastroenterol.* 9, 1950-1953 (2003); Fiordalisi et al. *Cancer Res.* 66, 3153-3161 (2006)) was terminated by treatment with 6-TG in combination with a NO donor for 3 days (FIG. 14B). Like with SUM149 cells (FIG. 14A), the expression level of RhoC in these cells was unchanged, but the activity of RhoC was drastically diminished when these cells were treated with 6-TG and a NO donor (not shown). This result suggests that, regardless of tumor types, the RhoC-mediated invasive cell motility can commonly be terminated by the action of 6-TG with a NO donor.

Analysis of RhoC 6-TGNP Adduct from Cells Treated with 6-TG and/or a Redox Agent.

To explore the underlying mechanism of the 6-TG-mediated inhibition of the motility of SUM149 and HME-RhoC cells in the presence of a redox agent, RhoC protein was isolated from these cells treated with or without 6-TG in the presence or absence of a redox agent; this protein then was digested and peptides were analyzed with ESI-MS. A mass peak 1481.6 Da., assigned to be a RhoC-derived peptide-6-TGDP disulfide adduct (TC[20]LLIVFSK-6-TGDP) (SEQ ID NO:4) (FIG. 15B), was commonly exhibited in co-immuno-precipitated (co-IPed) RhoC samples isolated from both SUM149 cells (FIG. 15A, upper panel of the left column) and HME-RhoC cells treated with 6-TG (FIG. 15A, upper panel of the right column). In the presence of a NO donor, the peak assigned to be a RhoC-6-TGDP adduct also was increased, suggesting that a NO donor enhances the formation of the RhoC-6-TGDP adduct. However, this 1481.6 Da. mass peak was not found in control cell samples that were untreated with 6-TG (FIG. 15A, lower panel of the left and right columns). This result suggests that 6-TGDP, which is derived from treated 6-TG, targets the Cys[20] side chain of the redox sensitive GXXXXGK(S/T)C (SEQ ID NO:1) motif of RhoC in SUM149 and HME-RhoC cells to produce a RhoC-6-TGDP adduct.

Distinctive to SUM149, RhoC mRNA expression in SUM102 cells has been shown to be low (van Golen et al. *Clin. Cancer. Res.* 5, 2511-2519 (1999)). However, the minimally expressed RhoC in SUM102 cells also could react with 6-TGDP to produce the 1481.6 Da. peak (FIG. 15A, middle panel of the left column). Additionally, other Rho GTPases, such as RhoA and RhoB, possess the redox-sensitive GXXXXGK(S/T)C (SEQ ID NO:1) motif with an identical sequence of TC[20]LLIVFSK (SEQ ID NO:4). Hence, it also is possible that the origin of the 1481.6 Da. peak from the SUM102 sample can be derived from the reaction between 6-TGDP and the endogenously present RhoA and/or RhoB. Because C20S RhoC lacks the redox-sensitive Cys[20] residue, the RhoC-peptide adduct was not expected to be detected in HME-C20S RhoC cells. However, a low intensity but definite 1481.6 Da. peak was also observed when HME-C20S RhoC cells were treated with 6-TG (FIG. 15A, middle panel of the right column). As with SUM102 cells, the endogenously expressed RhoA and RhoB in HME-C20S RhoC cells may be a target of 6-TGDP and subsequently produce a RhoA- and/or RhoB-6-TGDP adduct.

Because cells maintain a ratio of GTP/GDP larger than 1 (Traut, T. W. *Mol. Cell. Biochem.* 140, 1-22) (1994)), the cellular concentration of 6-TGTP also is likely to exceed that of 6-TGDP. However, ESI-MS analysis has detected a RhoC fragment TC[20]LLIVFSK with 6-TGDP (TC[20]LLIVFSK-6-TGDP) (SEQ ID NO:4) but not with 6-TGTP (TC[20]LLIVFSK-6-TGTP) (SEQ ID NO:13) (FIG. 15A). This is likely because the γ phosphate of 6-TGTP is so unstable that during preparation of the ESI-MSI sample, particularly the digestion at room temperature of the co-IPed RhoC fraction with trypsin, results in conversion of the 6-TGTP into 6-TGDP that was covalently attached to the RhoC Cys[20] side chain.

Kinetic Properties of Rho GTPases with 6-TGNP in the Presence or Absence of a Redox Agent.

To better understand the 6-TGNP-mediated inactivation mechanism of RhoC with or without a redox agent, a redox-based biochemical analysis was performed for Rho GTPases, including RhoC and RhoA with 6-TGDP.

A competitive binding study shows that GDP bound to RhoA and RhoC can be displaced with 6-TGDP (FIG. 16A), similar to that of the Ras GDP with 6-TGDP (Heo et al. *Biochemistry* 49, 3965-3976 (2010)). The RhoC and mutant RhoC bound GDP also can be competitively displaced with 6-TGDP (FIG. 16A). The binding affinities that 6-TGDP has for all of these examined Rho proteins are ~2-fold weaker than that of GDP for Rho proteins (FIG. 16A). However, the range of the determined values of the true dissociation constant ($^{true}K_D$) of Rho proteins for 6-TGDP, including C20S RhoC (FIG. 16A), nevertheless indicates that 6-TGDP has a high affinity for binding to Rho GTPases.

None of the redox agents tested was able to enhance GDP dissociation from C20S RhoC (FIG. 16B). Rates of the NOor $N_2O_3$-mediated GDP dissociation from RhoC were minimal (FIG. 16B). However, $.NO_2$ enhances dissociation of GDP from RhoC (FIG. 16B). These results were consistent with a previous study suggesting that $.NO_2$, but neither NO nor $N_2O_3$, targets the GXXXXGK(S/T)C (SEQ ID NO:1) motif of the redox-sensitive Rho GTPases to enhance Rho GDP dissociation (Heo et al. *J. Biol. Chem.* 280, 31003-31010 (2005)). $.NO_2$, but neither NO nor $N_2O_3$, enhances dissociation of 6-TGDP from the redox inert C20S RhoC (FIG. 16C). A previous study (Heo et al. *J. Biol. Chem.* 280, 31003-31010 (2005)) provides an explanation for this result in which $.NO_2$ targets the sulfur atom of the bound 6-TGDP, rather than the redox inert C20S RhoC protein, to produce the 6-TGDP-$NO_2$ adduct that can be degraded into 5-guanidino-4-nitroimidazole diphosphate. Dissociation of 6-TGDP from RhoC and mutant RhoC C20S by NO or $N_2O_3$ was minimal (FIG. 16C).

Because of the result associated with the action of $.NO_2$ on the GDP-bound RhoC combined with the 6-TGDP-bound C20S RhoC, it is predictable that the target action of $.NO_2$ on a RhoC-6-TGDP complex would be more effective; this is because both the ligand and receptor of the RhoC-6-TGDP complex, 6-TGDP and RhoC, are redox sensitive. Unexpectedly, however, a much slower rate of $.NO_2$-mediated 6-TGDP dissociation from RhoC was observed compared with that of 6-TGDP dissociation from C20S RhoC or GDP dissociation from RhoC (FIG. 16C). To better understand this enigmatic result, the 6-TGDP-loaded RhoC was pretreated with $.NO_2$, and a competitive displacement of the preloaded 6-TGDP with GDP was performed. Only a minimal fraction of the preloaded 6-TGDP was dislodged with GDP (FIG. 16D). Dbs, the RhoC GEF, also was unable to displace the bound 6-TGDP with GDP. This blockage of dissociation of the bound 6-TGDP from RhoC was not observed when the RhoC-6-TGDP complex was untreated or pretreated with NO or $N_2O_3$. The mass peak 1481.6 Da. identified in cell samples treated with 6-TG (FIG. 15A) also was found in this in vitro kinetic study sample of RhoC-6-TGDP that was treated with $.NO_2$ and trypsin but not with either NO or $N_2O_3$. The 6-TGDP in the $.NO_2$-treated 6-TGDP C20S RhoC complex can be displaced with GDP (FIG. 16D). The kinetic results with RhoC and mutant RhoC in conjunction with MS data suggests that the $.NO_2$-mediated formation of the RhoC $Cys^{20}$-6-TGDP disulfide adduct is linked to blockage of the dissociation of the 6-TGDP from RhoC in the presence and absence of Dbs.

A treatment of the $.NO_2$ pretreated-RhoC-6-TGDP complex with a reducing agent DTT enables the competitive displacement of RhoC-bound 6-TGDP with GDP (FIG. 16D). Another reducing agent, β-mercaptoethanol, also enhances displacement of RhoC bound 6-TGDP with GDP. This is likely because DTT or β-mercaptoethanol reduces and thus disrupts the disulfide bond between 6-TGDP and the RhoC $Cys^{20}$ side chain. This unlinked 6-TGDP can then be liberated from the RhoC protein, which is consistent with disulfide blockage.

Potential Mechanism for the Formation of the RhoC-6-TGDP Adduct.

A hypothesis that the formation of the RhoC $Cys^{20}$-6-TGDP disulfide adduct results in the blockage of the dissociation of the bound 6-TGDP from RhoC is quite possible because the sulfur atom of the bound 6-TGDP is vicinal to the sulfur atom of the RhoC $Cys^{20}$ side chain (Dias et al. *Biochemistry* 46, 6547-6558 (2007)).

Figure 17:
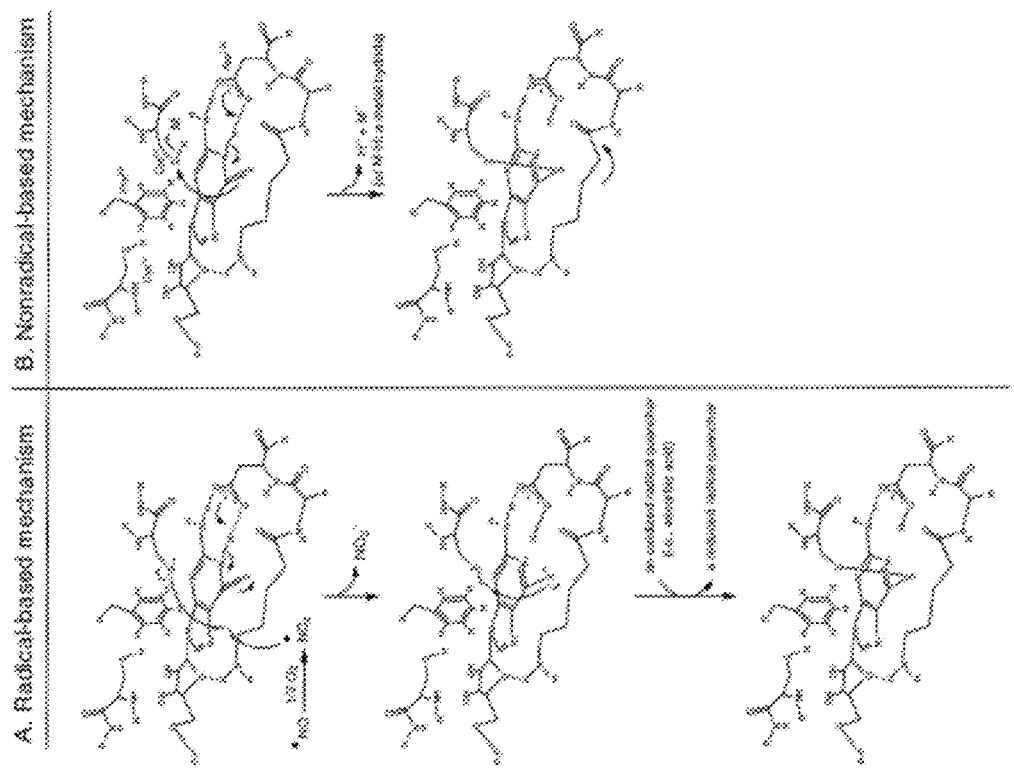
FIG. 17. Proposed mechanisms of the Rho 6-TGNP disulfide adduction formation. A symbol M in red represents a transition metal, serving for an electron acceptor. The dotted lines represent putative hydrogen-bond interactions between RhoC residues and 6-TGNP.
Figure 18:
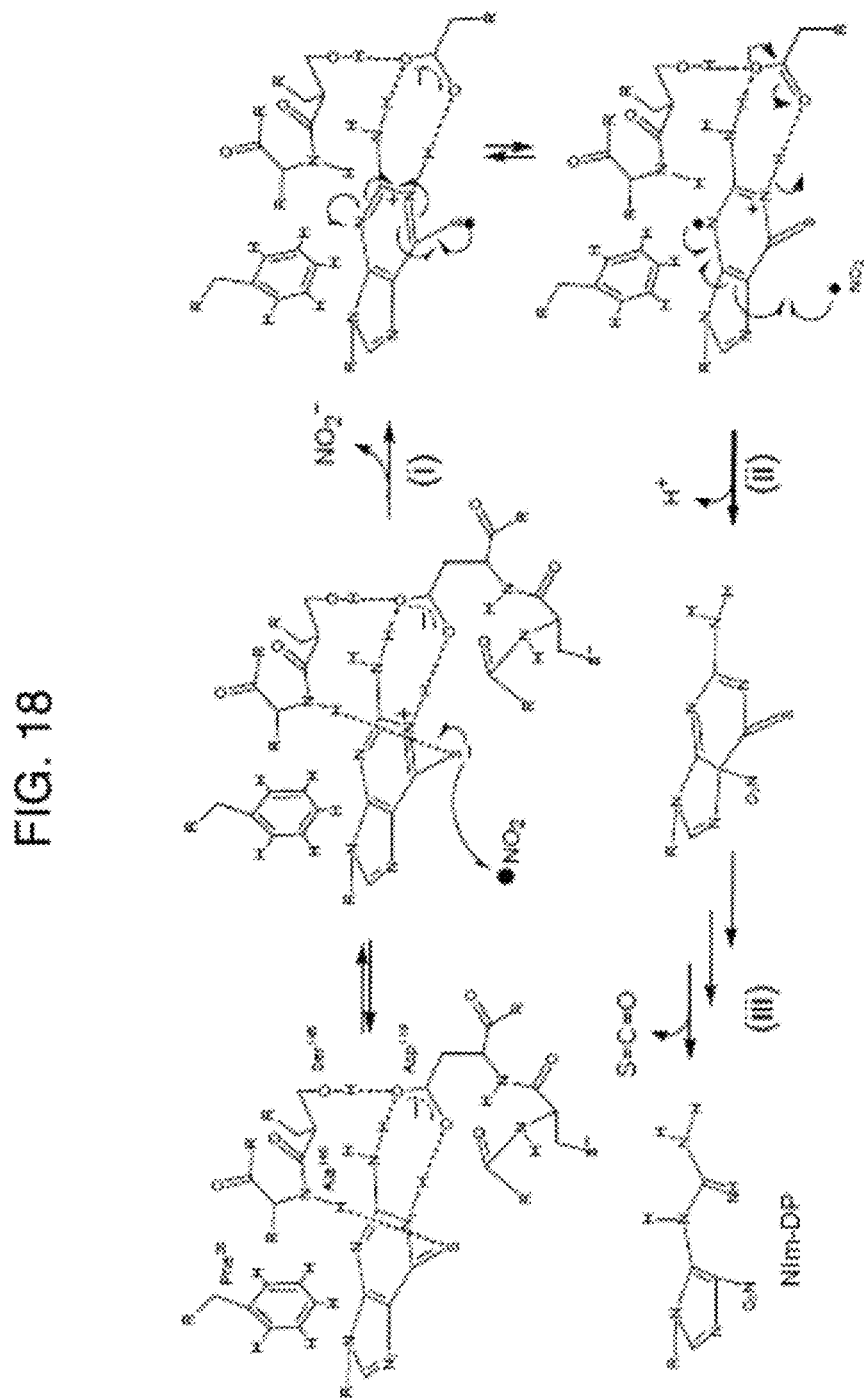
FIG. 18. Proposed mechanisms of action of 6-TGNP and a redox agent on Ras GTPases.
Figure 19:
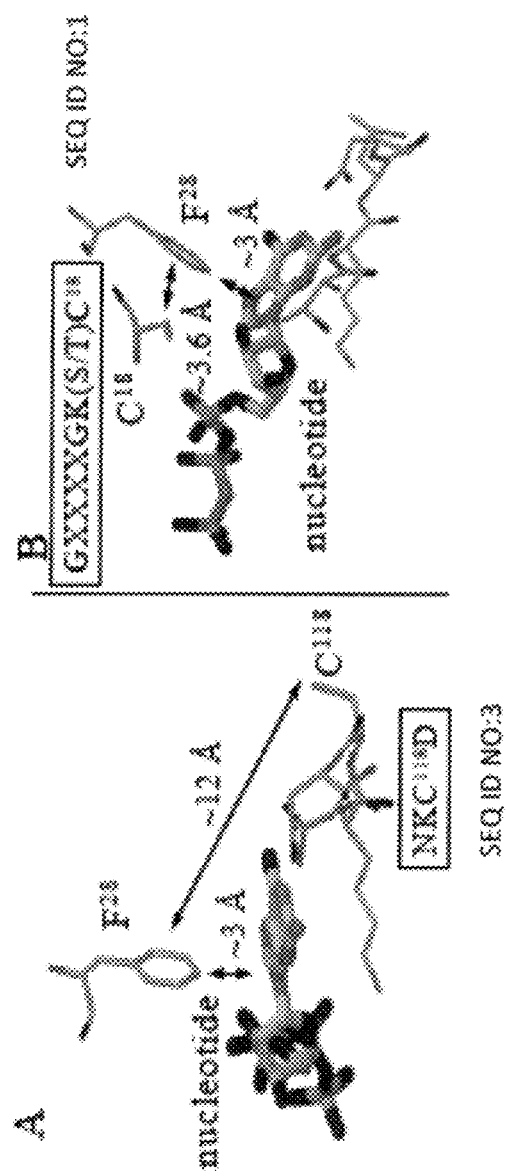
FIG. 19. Spatial architecture of the Phe[28] side chain and the NKCD motif of GTPases with the bound nucleotide. The redox-active Rho family GTPases possess the GXXXXGK(S/T)C (SEQ ID NO:1) motif (B) instead of the NKCD (SEQ ID NO:3) motif that is found in the redox-active Ras family GTPases (A). The distance and spatial orientation of the Phe[28] side chain, nucleotide ligand, and redox-active thiol group in the NKCD and GXXXXGK(S/T)C (SEQ ID NO:1) motif of Rap1A (A) and Rac1 (B), respectively, are presented. The Figure was generated by using RASMOL with PDB 1C1Y for the NKCD (SEQ ID NO:3) motif-containing Rap1A GTPase and PDB 1MH1 for the TKLD motif-containing Rac1 GTPase.

The results of an in vitro kinetic study also show that $.NO_2$ only enhances formation of the RhoC $Cys^{20}$-6-TGDP disulfide adduct. This is consistent with previous studies showing that $.NO_2$ reacts with a thiolate to produce a thiyl radical (Ford et al. *Free Radic. Biol. Med.* 32, 1314-1323 (2002); Jourd'heuil et al. *J. Biol. Chem.* 278, 15720-15726 (2003)). The thiyl radical formed also can react with a thiolate to produce a disulfide radical anion (Xu et al. *Chem. Rev.* 107, 3514-3543 (2007)). Because a disulfide radical anion is a strong reductant, it predominantly reacts with $O_2$ to produce $O_2.^-$ and a disulfide. On the basis of these previous studies, a molecular mechanism is proposed for the formation of the RhoC-6-TGDP disulfide adduct in the presence of $.NO_2$ (FIG. 17A). $.NO_2$ reacts with the RhoC $Cys^{20}$ side chain to produce a RhoC $Cys^{20}$ side chain thiyl radical. This RhoC radical then reacts with the sulfur of the RhoC-bound 6-TGDP in a 6-thioxo form to give a RhoC $Cys^{20}$ disulfide radical anion. This protein radical anion can be quenched by $O_2$ to produce a superoxide anion radical and the RhoC-6-TGDP disulfide adduct. It is also possible that the thiyl radical formed can further react with another thiyl radical to produce a disulfide molecule. Therefore, alternatively, if the 6-TGDP that possesses thiolate (a 6-sulfido form) is dominant, the sulfur atom of the bound 6-TGDP will be a target of $.NO_2$ to produce a 6-TGDP thiyl radical. This 6-TGDP radical then reacts with the RhoC $Cys^{20}$ side chain thiyl radical to produce the RhoC-6-TGDP disulfide adduct. However, because the $^{true}K_D$ value of RhoC for 6-TGDP deviated insignificantly from the value of RhoC for GDP, the state of the bound 6-TGDP is likely to be in a 6-thioxo form. Thus, formation of RhoC-6-TGDP disulfide via a direct targeting of the bound 6-TGDP is unlikely.

The nonradical-based process (FIG. 17B) also is possible. However, because formation of a disulfide bond was not detected between RhoC and the bound 6-TGDP in the presence of a transition metal (i.e., $Fe^{2+}$ or $Cu^{2+}$) but absence of $.NO_2$ under in vitro experimental conditions, this nonradical-based mechanism is unlikely to occur.

Figure 16:
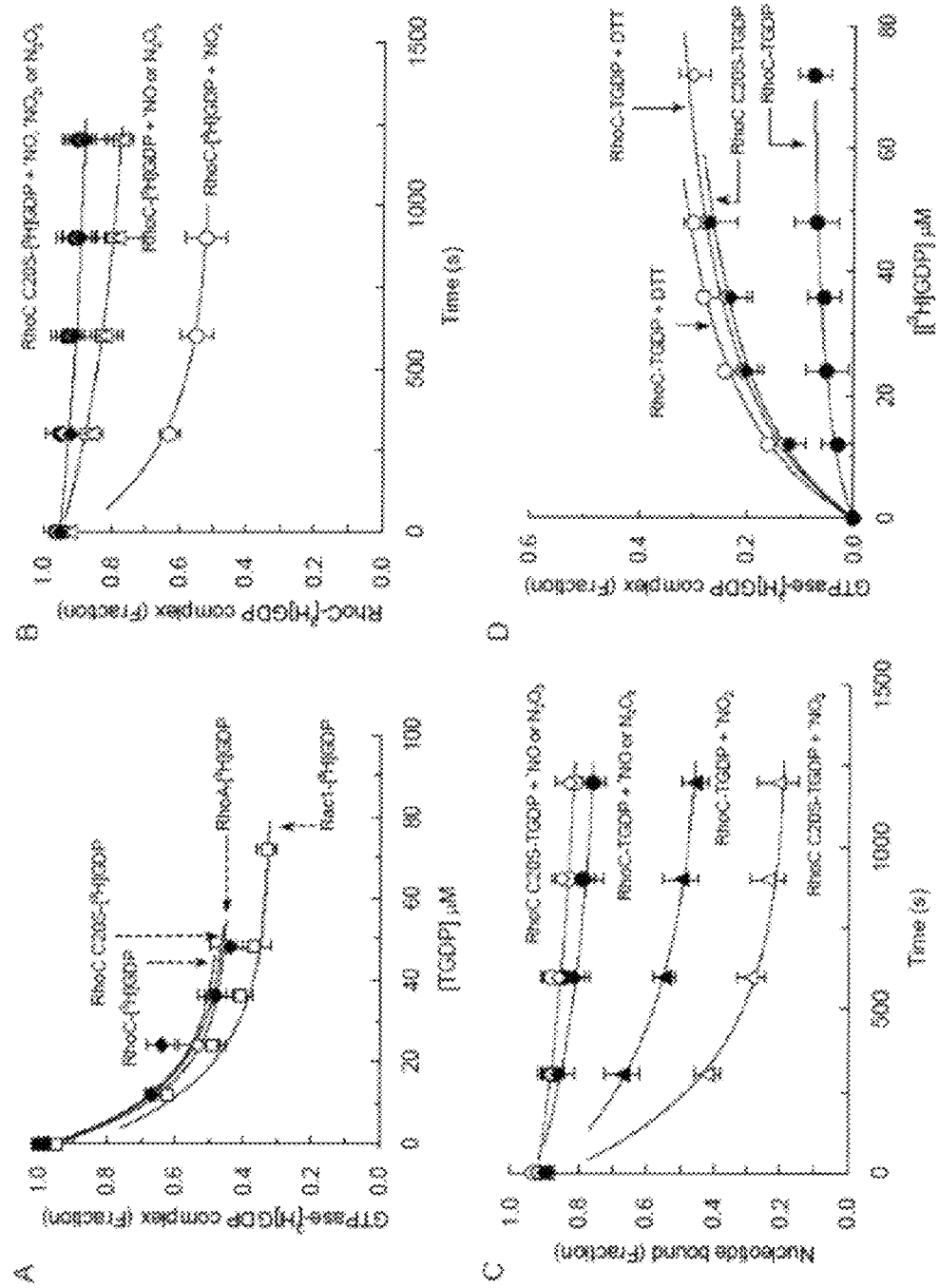
FIG. 16. Kinetic properties of RhoC with 6-TGDP in the presence or absence of a redox agent. All kinetic analyses are described elsewhere herein. (A) $^{app}K_D$ values of Rac1, RhoA, RhoC, and RhoC C20S for 6-TGDP were estimated to be 7.9, 11.6, 11.8, and 11.2 μM, respectively. $^{true}K_D$ values of Rac1, RhoA, and RhoC for 6-TGDP were then calculated to be 5.1, 10.8, 11.1, and 10.5 μM, respectively, by using a compensation equation, $^{true}K_D$ for 6-TGDP=$^{app}K_D$ for 6-TGDP/(1+ [[$^3$H]GDP]/$^{true}K_D$ for GDP) (Heo, J., and Hong, I. (2010) *Biochemistry* 49, 3965-3976), in conjunction with the values given. (The $^{true}K_D$ values of Rac1 and RhoA for GDP were known to be 1.8 μM and 13.0 μM (Morgan et al. *Cancer Res.* 54, 5387-5393 (1994)). Within this study, the $^{true}K_D$ value of RhoC and RhoC C20S for GDP was determined to be 15.0±8 μM and 14.2±8 μM, respectively.) (B) The rates of GDP dissociation from RhoC by NO, .$NO_2$, and $N_2O_3$ (a mixture of NO and .$NO_2$) were determined to be $0.19\times10^{-3}$, $6.04\times10^{-3}$, and $0.21\times10^{-3}$ s$^{-1}$, respectively. The GDP dissociation rates from RhoC C20S by NO, .$NO_2$, and $N_2O_3$ were estimated to be $0.02\times10^{-3}$, $0.05\times10^{-3}$, and $0.04\times10^{-3}$ s$^{-1}$, respectively. (C) The NO-, .$NO_2$-, and $N_2O_3$-mediated rates of 6-TGDP dissociation from RhoC by NO, .$NO_2$, and $N_2O_3$ were determined to be $0.08\times10^{-3}$, $2.65\times10^{-3}$, and $0.16\times10^{-3}$ s$^{-1}$, respectively. The rates of 6-TGDP dissociation from RhoC C20S in the presence of NO, .$NO_2$, and $N_2O_3$ were estimated to be $0.04\times10^{-3}$, $6.27\times10^{-3}$, and $0.12\times10^{-3}$ s$^{-1}$, respectively. (D) $^{app}K_D$ values of RhoC for [$^3$H]GDP in the presence or absence of DTT were estimated to be 22.4 μM and 103.7 nM, respectively. $^{app}K_D$ values of C20S RhoC for [$^3$H]GDP in the presence or absence of DTT were determined to be 24.8 μM and 25.2 μM, respectively. The regression values associated with these fits were >0.8595. All data points associated with vertical standard error bars shown in this figure are the mean values of triplicate measurements.

All forms of 6-TGNP, such as 6-TGDP and 6-TGTP, have the same 6-TG moiety; they differ from each other only in the number of phosphates linked to the thio-nucleotide ribose. The proposed mechanism suggests that the results of kinetic analysis of 6-TGDP with RhoC shown in this study are intrinsic to the chemical properties of the thiolate moiety of 6-TG of 6-TGDP coupled with the RhoC $Cys^{20}$ side chain. Hence, the biochemical features of other 6-TGNPs, such as 6-TGTP, with RhoC will not differ significantly from those of 6-TGDP with RhoC (FIG. 16).

Example 4

Inhibitory Action of Thiopurine Drugs on RhoA GTPase and its Implication in Smooth Muscle Cells Underlying Blood Vessels Although misregulation of RhoA seems linked to major blood vessel diseases (Rabinovitch, M. *Toxicol. Pathol.* 19, 458-469 (1991); Numaguchi et al. *Circ. Res.* 85, 5-11 (1999); Laufs et al. *Circ. Res.* 87, 526-528 (2000); Alvarez de Sotomayor et al. *Eur. J. Pharmacol.* 415, 217-224 (2001); Kuzuya et al. *J. Cardiovasc. Pharmacol.* 43, 808-814 (2004); Kontaridis et al. *Circulation* 117, 1423-1435 (2008)), no therapeutic agent exists that directly targets and inhibits RhoA activity (Oka et al. *Br. J. Pharmacol.* 155, 444-454 (2008)). 6-TGNP is shown to also target and inhibit RhoA in A7r5 cells derived from rat aortic Vascular Smooth Muscle Cells (VSMCs). This 6-TG-mediated inhibition of RhoA may induce vasorelaxation in blood vessels, because inactivation of RhoA was shown to be coupled with the dephosphorylation of the myosin light chain (MLC) in A7r5 cells. Dephosphorylation of MLC is known to cause vasorelaxation. The mechanism of action of TP drugs (as a form of 6-TGNP) on RhoA inactivation likely is the same as that for TP drugs on Rac1 inactivation; although 6-TGNP can target any known redox-sensitive Rho protein, such as Rac1 or RhoA, it specifically targets and inhibits Rac1 or RhoA via formation of a Rac1-6-TGNP adduct or RhoA-6-TGNP adduct, respectively, in T and A7r5 cells. Other findings with regard to the action of TP drugs on Rac1 and RhoA GTPases include: (i) a novel analog of 6-TP, 8-TP (i.e., 8-TG), can be converted into 8-thioguanosine phosphate (8-TGNP), which also targets and inhibits RhoA in A7r5 cells via formation of a RhoA-8-TGNP disulfide adduct; (ii) a redox agent, nitric oxide (NO), enhances the 6- or 8-TP-mediated blocking of Rho GTPase guanine nucleotide exchange (GNE). This enhancement may occur by facilitating formation of the Rho protein-6- or 8-TGNP adduct; and (iii) finally, 6- or 8-TP aids dephosphorylation of the MLC and causes vasorelaxation in A7r5 cells.

Effects of 6-TPs on RhoA in A7r5 and T Cells.

Figure 20:
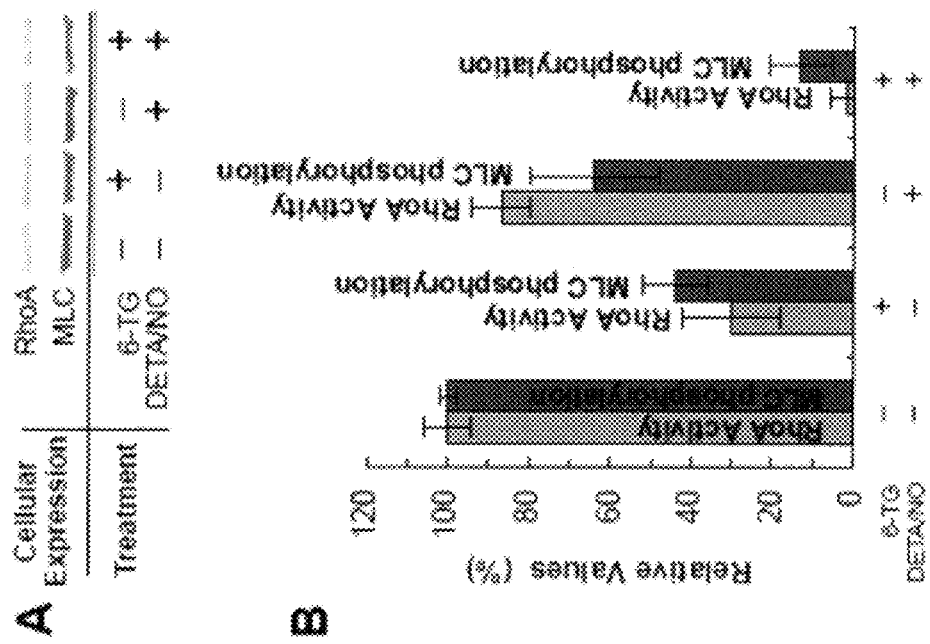
FIG. 20. Determination of RhoA activity and MLC phosphorylation. A7r5 cells treated with 6-TG (1 μM) and/or DETA/NO (10 μM) for 3 days. Cell lysates in a buffer containing 1% NP-40, 10 mM EDTA, and 20 mM TrisHCl (pH 7.4) were centrifuged (50,000×g, 20 min) to remove solid matter. (A) The soluble cell extract was then used to perform Western blot analyses for RhoA and the MLC. This cell extract also was used for the co-IP-based ESI-MS analysis (FIG. 6). (B) A RhoA activity assay was colorimetrically determined using cell extract; the assay was performed with the RhoA G-LISA Activation Assay Kit (Cat. No. BK124) (Denver, Colo.). To examine the level of phosphorylation of the MLC, cells were cultured with ~5 μCi of $^{32}$P in 1 mL of phosphate-free DMEM. The collected cell extract was nutated with resin coupled with a macrophage myosin II antibody at 4° C. for 5 h. Resin was collected by centrifugation, and proteins bound to the resin were washed and eluted with a buffer (80° C.) containing 25% SDS, 5 mM DTT, and 10 mM TrisHCl (pH 6.8). The immunoprecipitates were then analyzed by SDS-PAGE and autoradiographed. The values of RhoA activity and the MLC phosphorylation determined from untreated cells were set at 100%. All data obtained from cells treated with 6-TG and/or DETA/NO were then expressed as normalized values against the standards initially established. The data represented in the figure represent the mean values of triplicate measurements, and the vertical error bar indicates standard errors.
Figure 21:
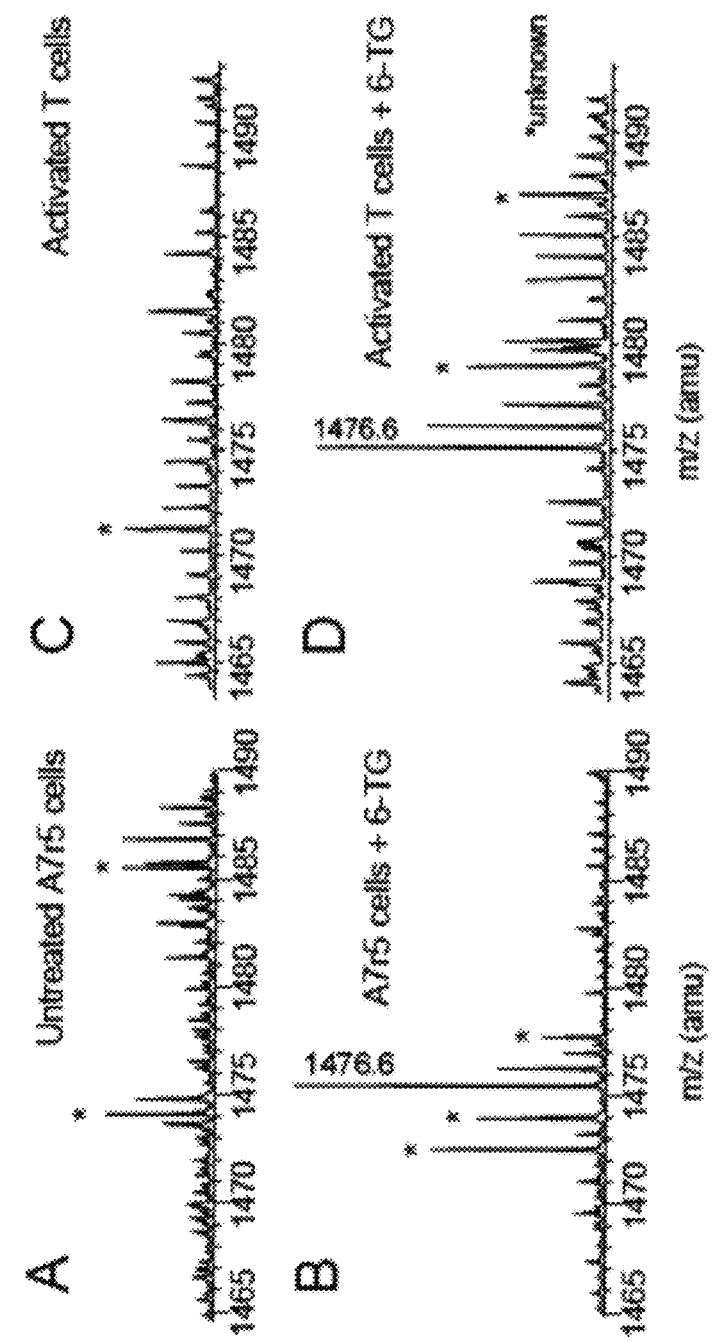
FIG. 21. Detection of 6-TGNP adduct from A7r5 and T cells. Experimental procedures using A7r5 (A and B) and T (C and D) cells, respectively, were identical to those of the experiments described in FIG. 19 and previous studies (Tiede et al. *J. Clin. Invest.* 111, 1133-1145 (2003); and Poppe et al. *J. Immunol.* 176, 640-651 (2006)). The cell extract was incubated with a monoclonal RhoA antibody (A and B) or a Rac1 antibody (C and D) coupled with resin. Resin was collected by centrifugation (5,000×g, 10 min), which was suspended in 50% methanol:0.1% formic acid. The protein portion was separated by brief centrifugation (3,000×g for 5 min), resuspended in a buffer containing 10 mM EDTA and 5 mM phosphate (pH 7.5), digested with trypsin for 10 h, and analyzed with MS. The MS peak at 1476.6 Da represents peptide-6-TGDP adduct; TC[20]LLIVFSK-6-TGDP.
Figure 23:
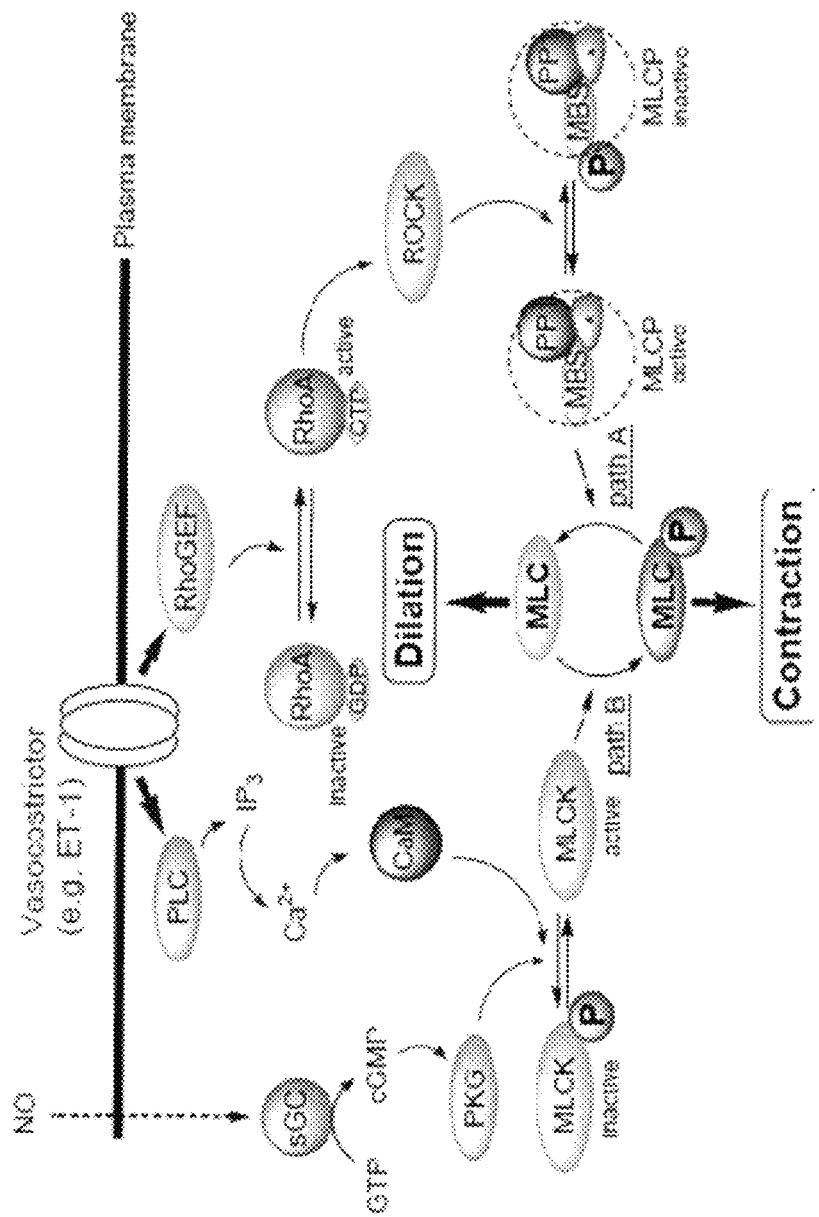
FIG. 23. Mechanism of pulmonary vasocontraction and dilation. The solid arrows indicate the paths of activation, as well as show activation and inactivation of cellular proteins. A dotted arrow shows an NO mediated stimulation path of sGC. Abbreviations: ET-1, endothelin-1; PLC, phospholipase C; IP3, inositol trisphosphate; CaM, Calmodulin; NO, nitric oxide; sGC, soluble guanylyl cyclase; cGMP, cyclic GMP; PKG, cGMP dependent protein kinase; MLCK, myosin light chain kinase; ROCK, RhoGEF, Rho guanine nucleotide exchange factor; Rho kinase; MLCP, myosin light chain phosphatase; and MLC, myosin light chain. MLCP consists of three domains as indicated with a dotted line: MBS (also known as MYPY-1), a myosin-binding subunit; PP1, a catalytic domain; and an *unknown noncatalytic domain.

The cellular expression levels of RhoA and of the MLC in A7r5 cells in the presence or absence of 6-TG was not changed (FIG. 20A). However, a significant portion of RhoA was inactivated within 3 days when A7r5 cells were treated with 6-TG (FIG. 20B). A large portion of the MLC in A7r5 cells was observed to have been dephosphorylated after 3 days following treatment with 6-TG (FIG. 20B). Analyses using co-IP-based ESI-MS (FIG. 21) suggest that this result occurs because the thiol moiety of 6-TGNP (cellularly converted from the treated 6-TG) reacts with the thiolate side chain $Cys^{20}$ of the RhoA GXXXXGK(S/T)C (SEQ ID NO:1) motif to produce a biologically inactive 6-TGNP-RhoA disulfide adduct. Taking these results into consideration, along with the RhoA/ROCK signaling associated with vasocontraction and dilation (FIG. 23, Path A), and without being bound by theory, it is hypothesized that 6-TPs target and inactivate RhoA. In turn, this results in dephosphorylation of the MLC via a cascade of downregulation and thus upregulation of ROCK and the MLCP. Using co-IP-based ESI-MS, a 6-TGNP-Rac1 disulfide adduct has been identified in activated T cells treated with 6-TG (FIG. 21). This result in conjunction with previous studies (Tiede et al. *J. Clin. Invest.* 111, 1133-1145 (2003); Poppe et al. *J. Immunol.* 176, 640-651 (2006)) suggests that the 6-TP mediated inactivation of Rac1 in T cells is due to the formation of a 6-TGNP-Rac1 disulfide adduct.

Examination of the Potential Target Specificity of 6-TPs on RhoA in A7r5 Cells.

To examine whether the cellular targeting action of 6- or 8-TG on RhoA depends on the action of Dbs and its target specificity, A7r5 cells were treated with small interfering RNA directly against Dbs (Dbs siRNA) in the presence and absence of 6- or 8-TG. The results show that the fraction of inactive RhoA and dephosphorylated form of the MLC in A7r5 cells treated with both Dbs siRNA and 6- or 8-TG was smaller than the fraction of inactive RhoA and dephosphorylated form of the MLC in untreated A7r5 cells. However, the fraction of inactive RhoA and dephosphorylated form of the MLC in A7r5 cells treated with both Dbs siRNA and 6- or 8-TG was similar to that treated with only 6- or 8-TG (data not shown). The interpretation of these results is that the elimination of Dbs mRNA by siRNA results in loading failure of not only 6- or 8-TGNP but also of regular GNP onto RhoA; the result is the inhibition of RhoA and dephosphorylation of the MLC regardless of the presence of 6- or 8-TG. Hence, the current cell results using Dbs siRNA do not constitute evidence of the role of Dbs in the action of 6- or 8-TGNP on RhoA.

An in vitro kinetic study has been designed that can verify whether the target action of 6- or 8-TG on Rac1 hinges on the action of Vav and its target specificity. Although this proposed in vitro experiment is not cell based, it will aid in explaining the role of the GEF in the 6- or 8-TG-mediated inactivation of Rac1 or RhoA.

Effects of a Redox Agent on the Formation of 6-TGNP-RhoA Adduct in A7r5 Cells.

An endogenously released cellular redox agent (e.g., $.NO_2$ or $O_2.^-$) could be involved in the formation of 6-TGNP-Rho protein adduct in cells. This possibility arises because a thiol (or thiolate) does not react with another thiol except in the presence of a radical redox agent (e.g., $.NO_2$ or $O_2.^-$) (Heo et al. *Biochemistry* 45, 14481-44489 (2006)). Additional treatment of cells with an NO releasing agent (e.g., diethylenetriamine/nitric oxide (DETA/NO); 10 µM for every 8 h), in addition to 6-TG, synergistically increases the fraction of inactive RhoA and the dephosphorylated form of the MLC (FIG. 20B). Because NO released from DETA/NO can be converted into $.NO_2$ in the presence of $O_2$, which enhances disulfide bond formation (Heo et al. *Biochemistry* 45, 14481-14489 (2006)), the rate at which an NO donor enhances formation of the bound 6-TGNP-RhoA disulfide bond (FIG. 7) is hypothesized. MS analysis also showed that the MS peak at 1476.6 Da, which represents the 6-TGNP-RhoA adduct, increased when cells were treated with both 6-TG and NO. However, under experimental conditions, the intensity of the MS peak was not truly quantitative. Thus, the intense MS peak for the 6-TGNP-RhoA adduct does not necessarily indicate that NO enhances formation of the 6-TGNP-RhoA adduct. Nonetheless, this enhanced formation of the 6-TGNP-RhoA adduct may further facilitate dephosphorylation of the MLC. However, because NO can down-regulate the MLCK via the sGC signaling pathway that populates the dephosphorylated form of the MLC (FIG. 23, Path B), the synergistic action of a redox agent may be partly because of the NO-mediated downregulation of the MLCK. This postulation of the MLCK downregulation is consistent with the result that when cells were treated with only an NO donor (DETA/NO ≅10 µM), a minimal fraction of RhoA was inactivated, but a sizable fraction of the MLC was dephosphorylated (FIG. 20B). Intriguingly, RhoA also can be inactivated by an NO donor alone, but this inactivation requires a relatively higher concentration of the NO donor (i.e., DETA/NO >~50 µM) (not shown). This redox agent concentration-dependent RhoA inactivation is likely because DETA/NO facilitates formation of a disulfide between RhoA $Cys^{20}$ and Cys16 that leads to inactivation of RhoA (Heo et al. *Biochemistry* 45, 14481-14489 (2006)).

Effects of 8-TG on RhoA.

Figure 4:
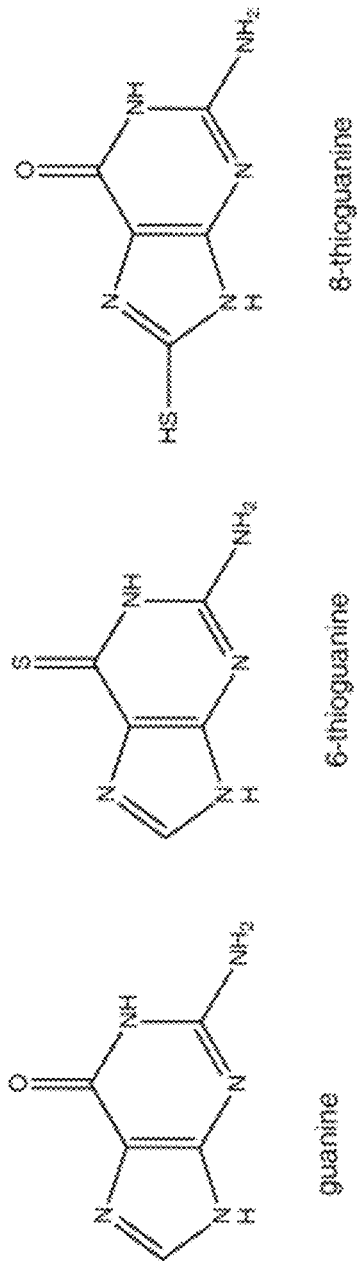
FIG. 4. Structures of guanine base and its analogs.
Figure 22:
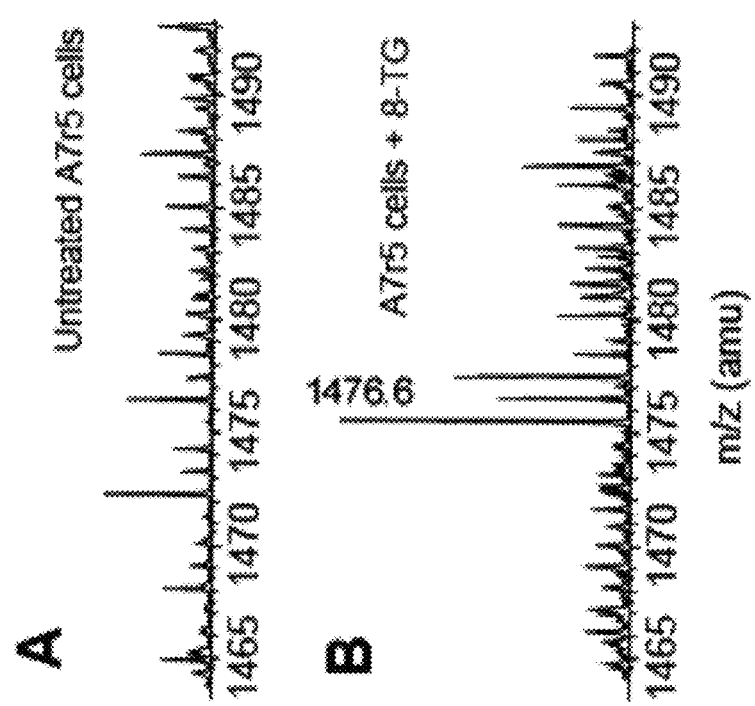
FIG. 22. Detection of 8-TGNP adduct from A7r5 cells. Experimental procedures using A7r5 cells were identical to those of the experiments described in FIG. 19, except that 8-TG instead of 6-TG was used. The indicated MS peak at 1476.6 Da represents peptide-8-TGDP adduct; TC[20]LLIVFSK-8-TGDP (SEQ ID NO:4). The molecular weight of the peptide-8-TGDP adduct is exactly the same as that of the peptide-6-TGDP adduct. A and B, respectively, represent any of samples taken from a cell culture with and without treatment with 8-TG.

A rapid accumulation of 6-TG in the DNA of fast-growing cells (i.e., tumors) triggers the action of MMR, inducing apoptosis (Heo et al. *Biochemistry* 49, 3965-3976 (2010)). However, because of the gradual rate of accumulation of DNA 6-TG in slow-growing cells, such as A7r5 cells, the observed cell apoptosis is relatively minimal compared with what occurs in fast-growing tumor cells. Nevertheless, this minimal 6-TG-mediated apoptosis may still cause a certain degree of cytotoxicity (i.e., an increase in cell viability up to ~5%). To develop a better agent to minimize potential cytotoxicity, the effects of various 6-TP isomers on A7r5 cells have been screened, such as 8-TG (2-amino-8-mercapto-1H-purin-6(9H)-one, see FIG. 4) and 7-thioguanine (2-amino-7-mercapto-8,9-dihydro-1H-purin-6(H)-one). Of the several isomers screened, 8-TG most effectively inhibits RhoA activity and dephosphorylates the MLC (not shown). As with 6-TGNP (FIG. 21), co-IP-based ESIMS analysis indicates that the thiol moiety of 8-TGNP (cellularly converted from the treated 8-TG) reacts with the thiolate side chain Cys[20] of the RhoA GXXXXGK(S/T)C (SEQ ID NO:1) motif to produce a biologically inactive 8-TGNPRhoA disulfide adduct (FIG. 22).

The structural feature of the nucleotide-binding pocket of RhoA explains the effective inhibitive action of 8-TG on cells when the distance between the sulfur atom of the RhoA Cys[20] side chain and the sulfur atom at the C8 position of base (~3.6 Å) is shorter than that of the sulfur atom of the RhoA Cys[20] side chain and the sulfur atom at the C6 position of base (~6.9 Å) (FIG. 12) Ohara et al. *J. Biol. Chem.* 273, 9656-9666 (1998)). Hence, the superior action of 8-TGNP is likely because structural cellular conditions may favor formation of a disulfide bond between the RhoA Cys[20] side chain and 8-TGNP over a similar bond with 6-TGNP.

Figure 24:
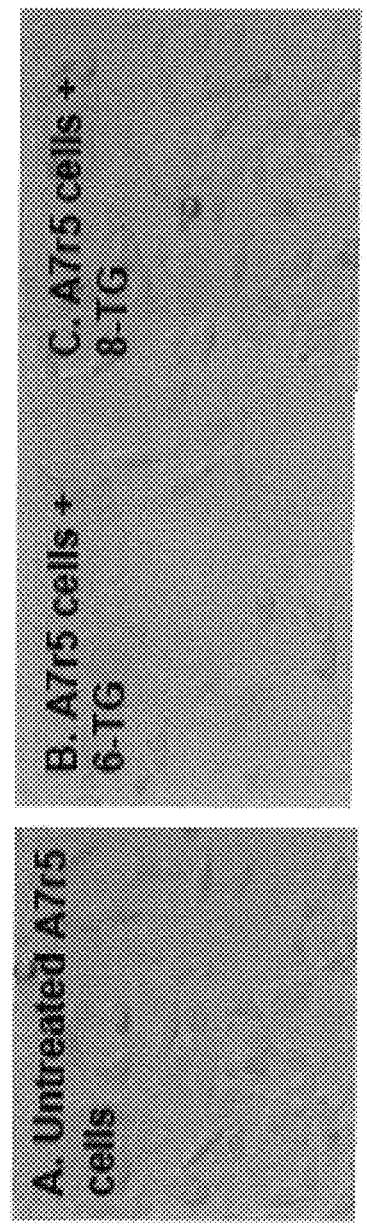
FIG. 24. Effects of 6- and 8-TG on A7r5 cells. Treatment of cells with 6- or 8-TG is described in FIGS. 19 and 21. The image associated with the effect of 6- or 8-TG was taken after 5 days of treatment.

Intriguingly, although 6-TG can induce minimal cytotoxicity in A7r5 cells, 8-TG did not alter the viability of A7r5 cells under experimental conditions (FIG. 24). While the aim is not to characterize the cellular/mechanical reason for the minimal cytotoxicity of 8-TG compared to that of 6-TG, the No. 6 position of the sulfur atom of 6-TG, but not the No. 8 position of the sulfur atom of 6-TG, in DNA likely triggers MMR to induce apoptosis. Evading the DNA MMR can be of benefit for a potential drug (e.g., 8-TG) that targets a protein such as RhoA. This would be because, compared with 6-TPs, it consequently could not have the cytotoxicity associated with MMR-induced apoptosis. However, evading the DNA MMR could be a disadvantage for a drug aimed at inducing apoptosis. In fact, a therapeutic effect of 6-TPs is rooted in stimulation of the DNA MMR (Lage et al. *J. Cancer Res. Clin. Oncol.* 125, 156-165 (1999); Yan et al. *Clin. Cancer Res.* 9, 2327-2334 (2003); Karran et al. *Nat. Rev. Cancer* 8, 24-36 (2008)). More 6-TP can be incorporated into the DNA of fast-growing tumors (e.g., acute lymphoblastic leukemia) than into the DNA of normal cells. Hence, more DNA MMR-induced apoptosis can occur in tumor cells (e.g., acute lymphoblastic leukemia) than in normal cells. Nonetheless, 8-TG and its isomers may have been ignored as possible therapeutic agents (i.e., as antitumor agents) because 8-TG does not effectively induce MMR-mediated apoptosis.

Example 5

Immunosuppressive Effects of Thiopurine Drugs

The primary objective of this example is to examine the chemistry-based molecular mechanism by which commercially available thiopurine (TP) drugs may block T-cell activation via inhibition of Rac1, thereby suppressing the immune response. The results of these studies form a basis for the development of TP-based chemotherapeutic agent(s) for autoimmune disorders.

Figure 26:
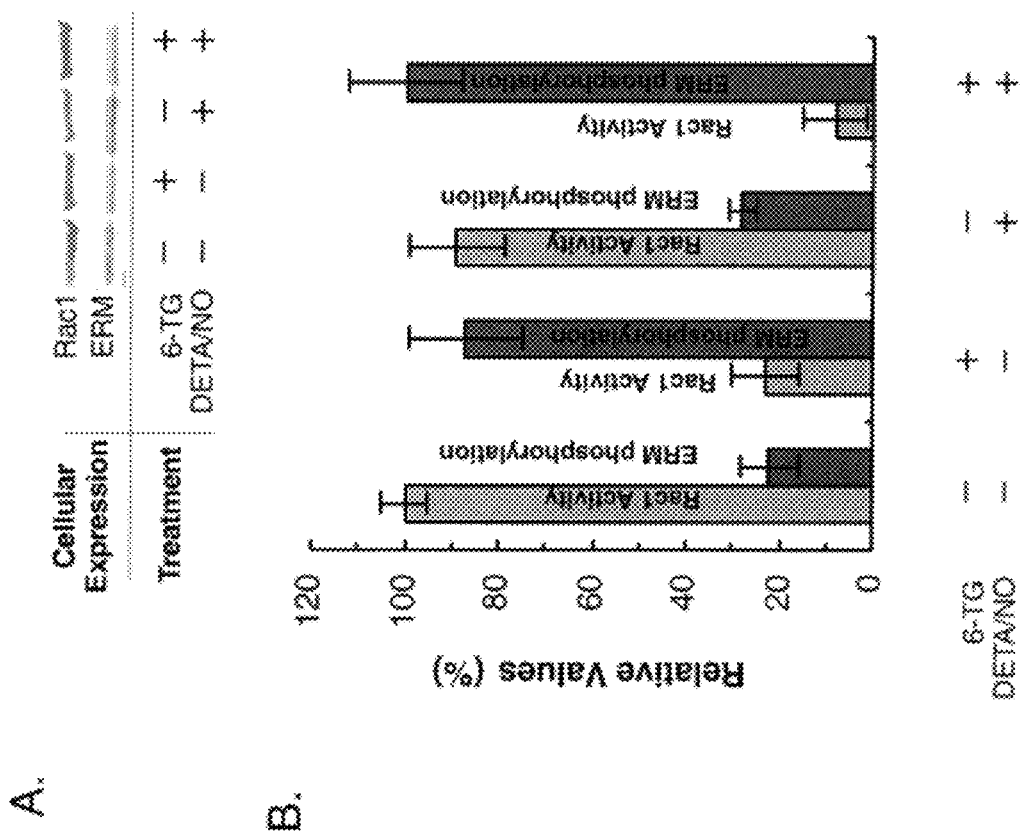
FIG. 26. Determination of Rac1 activity and ERM phosphorylation. Activated T cells treated with 6-TG (1 µM) and/or DETA/NO (10 µM) for 3 days. Cell lysates in a buffer containing 1% NP-40, 10 mM EDTA, and 20 mM TrisHCl (pH 7.4) were centrifuged (50,000×g, 20 min) to remove solid matter. (A) The soluble cell extract was then used to perform Western blot analyses for Rac1 and the ERM. This cell extract also was used for the co-IP-based ESI-MS analysis (FIG. 8). (B) A Rac1 activity assay was colorimetrically determined using cell extract; the assay was performed with the Rac1 G-LISA Activation Assay Kit (Cat. No. BK125) (Denver, Colo.). To examine the level of phosphorylation of the ERM, cells were cultured in complete RPMI 1640 medium with ~50 µCi of $^{32}$P/mL before initiating stimulation of T cells. The collected cell extract was nutated with resin coupled with a human ERM (231C2a) antibody (Santa Cruz Biotechnology, CA) at 4° C. for 5 h. Resin was collected by centrifugation, and proteins bound to the resin were washed and eluted with a buffer (80° C.) containing 25% SDS, 5 mM DTT, and 10 mM TrisHCl (pH 6.8). The immunoprecipitates were then analyzed by SDS-PAGE and autoradiographed. The value of Rac1 activity determined from untreated cells was set at 100%. The value of the ERM phosphorylation determined from cells treated with both 6-TG and DETA/NO was set at 100%. All data obtained from cells treated with 6-TG and/or DETA/NO were then expressed as normalized values against the standards initially established. The data represented in the figure represent the mean values of triplicate measurements, and the vertical error bar indicates standard errors.
Figure 29:
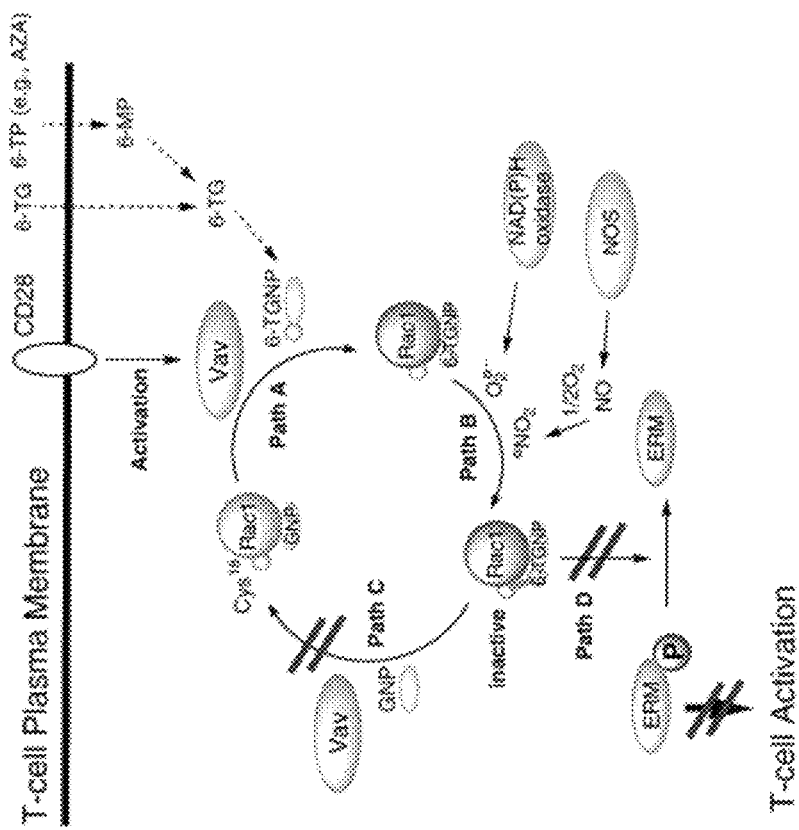
FIG. 29. Model mechanism of 6-TP-mediated immunosuppression. CD28 co-stimulation activates the Rac1 GEF Vav, which in turn enhances replacement of the Rac1-bound GNP with 6-TGNP (Path A). A redox agent, either .NO$_2$ or O$_2$.$^-$ from NOS and NAD(P)H oxidase, respectively, triggers a disulfide bond formation between the Cys[18] sulfur atom of Rac1 and the sulfur atom of 6-TGNP to produce a Rac1-6-TGNP disulfide adduct (Path B). Due to the disulfide bond, the Vav-mediated Rac1 GNE is blocked (Path C), resulting in accumulation of an inactive Rac1-6-TGNP disulfide adduct. Accumulation of inactive Rac1 GTPases leads to blockage of ERM dephosphorylation (Path D) that suppresses T cell activation. Dotted arrows show the pathway for the accumulation of 6-TGNP in cells. Abbreviations: CD28, Cluster of Differentiation 28; 6-TP, 6-thiopurine; 6-TG, 6-thioguanine; 6-MP, 6-mercaptopurine; 6-TGNP, 6-thioguanine nucleotide; GNP, guanine nucleotide; NOS, Nitric Oxide Synthase; and ERM, Ezrin-Radixin-Moesin.

The cellular and biochemical effect of 6-TG in combination with or without a redox agent on Rac1 was examined. The cellular expression level of Rac1 and ERM in T cells in the presence or absence of 6-TG was not changed (FIG. 26A). However, a significant portion of Rac1 was inactivated within 3 days when T cells were treated with 6-TG (FIG. 26B). A large portion of ERM in T cells was observed to have been phosphorylated after three days following treatment with 6-TG (FIG. 26B). Analyses using co-immunoprecipitation-based electrospray ionization mass spectrometry (co-IP-based ESI-MS) (See FIG. 21) suggest that this result occurs because the thiol moiety of 6-TGNP (cellularly converted from the treated 6-TG) reacts with the thiolate side chain Cys[20] of the Rac1 GXXXXGK(S/T)C (SEQ ID NO:1) motif. This reaction produces a biologically inactive 6-TGNP-Rac 1 disulfide adduct. Taking into consideration these results along with previous study results (Tiede et al. *J. Clin. Invest.* 111, 1133-1145 (2003); Poppe et al. *J. Immunol.* 176, 640-651 (2006)), without being bound by theory, it is believed that 6-TPs target and inactivate Rac1 via formation of the 6-TGNP-Rac1 disulfide adduct (FIG. 29, Path B). In turn, this results in blockage of the dephosphorylation of ERM (FIG. 29, Path D) and thus inactivates T cells.

Effects of a Redox Agent on the Formation of 6-TGNP-Rac1 Adduct in Cells.

An endogenously released cellular redox agent could be involved in the formation of 6-TGNP-Rac1 adduct in cells (FIG. 29, Path B). This possibility arises because a thiol (or thiolate) does not react with another thiol unless a radical redox agent (e.g., $.NO_2$ or $O_2.^-$) is present (Heo et al. *Biochemistry* 45, 14481-14489 (2006)).

Additional treatment of cells with an NO releasing agent (e.g., diethylenetriamine/nitric oxide (DETA/NO); 10 µM for every 8 h), in addition to 6-TG, synergistically increases the fraction of inactive Rac1 and also increases the blockage of the dephosphorylated form of ERM (FIG. 29B). Because NO released from DETA/NO can be converted into $.NO_2$ in the presence of $O_2$, which enhances formation of the disulfide bond (Heo et al. Biochemistry 45, 14481-14489 (2006)), it is believed the rate at which an NO donor enhances formation of the bound 6-TGNP-Rac1 disulfide bond (see FIG. 7). MS analysis also showed that the MS peak at 1476.6 Da, which represents the 6-TGNP-Rac1 adduct, increased when cells were treated with both 6-TG and NO. However, under experimental conditions, the intensity of the MS peak was not truly quantitative; consequently, the intensity of the MS peak for the 6-TGNP-Rac1 adduct does not necessarily indicate that NO enhances formation of the 6-TGNP-Rac1 adduct. Nonetheless, this enhanced formation of the 6-TGNP-Rac1 adduct may further facilitate blockage of the dephosphorylation of ERM.

Figure 27:
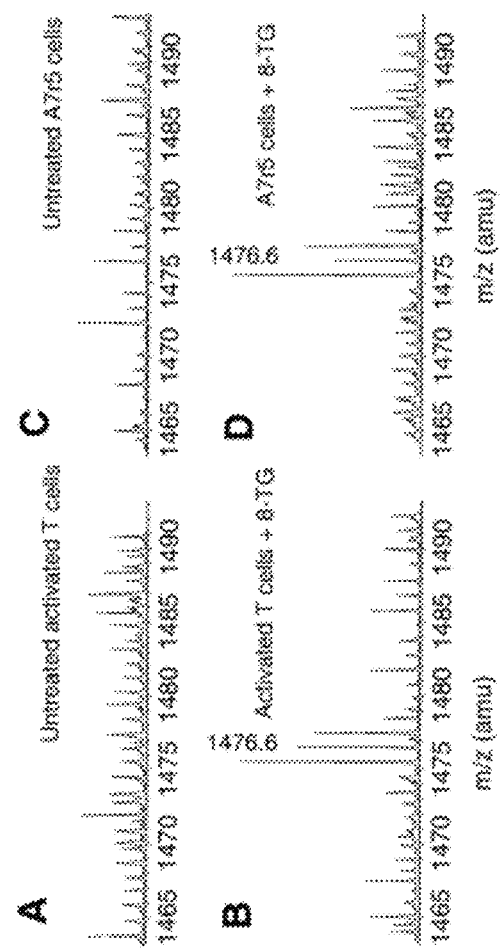
FIG. 27. Detection of 8-TGNP adduct from T and A7r5 cells. Experimental procedures using T (A and B) and A7r5 (C and D) cells were identical to those of the experiments described in FIG. 8, except that 8-TG instead of 6-TG was used. The indicated MS peak at 1476.6 Da represents peptide-8-TGDP adduct; TC[20]LLIVFSK-8-TGDP (SEQ ID NO:4). The molecular weight of the peptide-8-TGDP adduct is exactly the same as that of the peptide-6-TGDP adduct.

Effects of 8-TG on Rac1:

A rapid accumulation of 6-TG in the DNA of fast growing cells (i.e., tumors) triggers the action of MMR, inducing apoptosis (Heo et al. Biochemistry 49, 3965-3976 (2010)). However, because of the gradual rate of accumulation of DNA 6-TG in slow growing cells, such as T cells and primary epithelial cells, the observed cell apoptosis is relatively minor compared with what occurs in fast growing tumor cells. However, this minimal 6-TG-mediated apoptosis may still cause a degree of cytotoxicity. To develop a better agent to minimize this potential cytotoxicity, the effects of various 6-TP isomers on T cells have been screened, such as 8-TG (2-amino-8-mercapto-1H-purin-6(9H)-one) and 7-thioguanine (2-amino-7-mercapto-8,9-dihydro-1H-purin-6(H)-one). Of the several isomers screened, 8-TG most effectively inhibits Rac1 activity and blocks the dephosphorylation of ERM (not shown). As with 6-TGNP (FIG. 21), co-IP-based ESI-MS analysis indicates that the thiol moiety of 8-TGNP (cellularly converted from the treated 8-TG) reacts with the thiolate side chain Cys[18] of the Rac1 GXXXXGK(S/T)C (SEQ ID NO:1) motif to produce a biologically inactive 8-TGNP-Rac1 disulfide adduct (FIG. 27).

Figure 28:
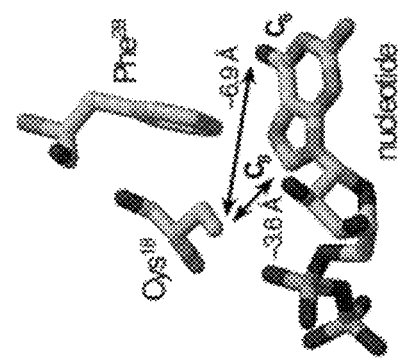
FIG. 28. Spatial architecture of Rac1 with the bound nucleotide. The distance and spatial orientation of the Phe28 side chain, nucleotide ligand, and the redox-sensitive thiolate group in the GXXXXGK(S/T)C (SEQ ID NO:1) motif of Rac1 are shown. The distance between the sulfur atom of the Cys[18] side chain and the C8 carbon of GDP is estimated to be ~3.6 Å. The distance between the sulfur atom of the Cys[18] side chain and the sulfur atom of the 8-TG base is shown to be ~6.9 Å. Finally, the distance between the sulfur atom of the Cys[18] side chain and the sulfur atom of the 8-TG base is calculated to be ~2.1 Å. The figure was generated by using RASMOL with PDB 1MH1.

The structural feature of the nucleotide-binding pocket of Rac1 (PDB 1 MH1) explains the effective inhibitory action of 8-TG on cells when the distance between the sulfur atom of the Rac1 Cys[18] side chain and the sulfur atom at the C8 position of base (~3.6 Å) is less than the distance of the sulfur atom of the Rac1 Cys[18] side chain from the sulfur atom at the C6 position of base (~6.9 Å) (FIG. 28) (Hirshberg et al. *Nat. Struct. Biol.* 4, 147-152 (1997)). Hence, the closer proximity of the Rac1 Cys[18] side chain and 8-TGNP is why they are the more likely pair to form a disulfide bond.

These studies show that 6-TP drugs (as a form of 6-TGNP) target and inhibit Rac1 via formation of a Rac1-6-TGNP adduct in T cells. These studies also show that 8-TP (i.e., 8-TG), an analog of 6-TP drugs, can be converted into 8-thioguanosine phosphate (8-TGNP) that targets and inhibits Rac1 in T cells. Without being bound by theory, it is believed that the formed disulfide adduct blocks the Rho guanine nucleotide exchange factor (GEF)-mediated guanine nucleotide exchange (GNE) of Rho protein, resulting in accumulation of an inactive Rho protein. Intriguingly, a redox agent, nitric oxide (NO), enhances the TP-mediated blocking of Rho GTPase GNE. This enhancement may occur via facilitation of the formation of the Rho protein-6 or 8-TGNP adduct. Without being bound by theory, a model mechanism of 6-TP-mediated immunosuppression is shown in FIG. 29. This proposed mechanism explains the previous observation in which the observed blockage of the Vav-mediated GNE of the 6-TGNP-bound Rac1 (Tiede et al. *J. Clin. Invest.* 111, 1133-1145 (2003); Poppe et al. *J. Immunol.* 176, 640-651 (2006)) (FIG. 29, path C) is because of the reactivity of 6-TGNP with the Rac1 Cys[18] to produce a 6-TGNP-Rac1 adduct that in turn blocks the action of Vav for Rac1 GNE.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual patent and publication was specifically and individually indicated as having been incorporated by reference in its entirety.

---

I claim:

1. A pharmaceutical composition for inhibiting a redox-sensitive GTPase protein comprising an effective amount of a redox-sensitive purine compound, an effective amount of a redox agent and an acceptable carrier, wherein the redox-sensitive purine compound is selected from the group consisting of a 6-thiopurine compound and an 8-thiopurine compound, wherein the GTPase protein comprises a GXXXXGK(S/T)C motif and the GTPase protein is selected from the group consisting of a Rho family GTPase and a Rab family GTPase.

2. The composition of claim 1, wherein the 6-thiopurine compound is 6-thioguanine and the 8-thiopurine compound is 8-thioguanine.

3. The composition of claim 1, wherein the redox-sensitive purine compound is selected from the group consisting of 8-thioguanine (2-amino-8-mercapto-1H-purin-6(9H)-one), 8-methylthioguanine (2-amino-8-(mercaptomethyl)-1H-purin-6(9H)-one), 7-methylthioguanine (2-amino-7-(mercaptomethyl)-8,9-dihydro-1H-purin-6(H)-one), 7-thioguanine (2-amino-7-mercapto-8,9-dihydro-1H-purin-6(H)-one), aza-thioprine (AZA), 6-mercaptopurine (6-MP); and 6-thioguanine (6-TG).

4. The composition of claim 1, wherein the redox-sensitive purine compound is selected from the group of compounds of formula I, wherein:

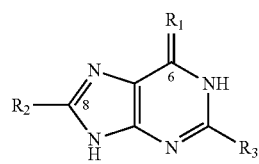

I $R_1$ is selected from the group consisting of C6-thioxo (C6=S; in combination with C6 of the purine base); C6-thiol (C6-SH; in combination with C6 of the purine base); C6-selenal (C6=Se; in combination with C6 of the purine base); C6-selenol (C6-SeH; in combination with C6 of the purine base); C1-4 straight chain or branched chain alkyl, alkenyl, or alkynyl, wherein C1-4 are unsubstituted, singly substituted or multiply substituted, wherein the substituents are selected from the group consisting of thiol, thioxo, selenal, selenol, hydroxyl, halogen, amino, ketone, alkoxy, aldehyde and carboxylic acid; OH; and O;

wherein $R_2$ is selected from the group consisting of H; thiol (SH); selenol (SeH); C1-4 straight chain or branched chain alkyl, alkenyl, or alkynyl, wherein C1-4 are unsubstituted, singly substituted or multiply substituted, wherein the substituents are selected from the group consisting of thiol, thioxo, selenal, selenol, hydroxyl, halogen, amino, ketone, alkoxy, aldehyde and carboxylic acid; $NH_2$; and OH;

wherein $R_3$ is selected from the group consisting of H, $NH_2$ and OH;

with the proviso that at least one of $R_1$ or $R_2$ is a moiety that comprises a redox-sensitive functional group selected from the group consisting of thioxo, thiol, selenal and selenol.

5. The composition of claim 1, wherein the redox agent is selected from the group consisting of nitric oxide, nitrogen dioxide, dinitrogen trioxide, superoxide anion radical, hydrogen peroxide, carbonate radical, and an agent which stimulates the production of a redox agent.

* * * * *